(12) United States Patent
Cortright et al.

(10) Patent No.: US 7,977,517 B2
(45) Date of Patent: *Jul. 12, 2011

(54) SYNTHESIS OF LIQUID FUELS AND CHEMICALS FROM OXYGENATED HYDROCARBONS

(75) Inventors: Randy D. Cortright, Madison, WI (US); Paul G. Blommel, Oregon, WI (US)

(73) Assignee: Virent Energy Systems, Inc., Madison, WI (US)

( * ) Notice: Subject to any disclaimer, the term of this patent is extended or adjusted under 35 U.S.C. 154(b) by 471 days.

This patent is subject to a terminal disclaimer.

(21) Appl. No.: 12/044,908

(22) Filed: Mar. 7, 2008

(65) Prior Publication Data

US 2008/0300435 A1    Dec. 4, 2008

Related U.S. Application Data

(60) Provisional application No. 60/985,475, filed on Nov. 5, 2007, provisional application No. 60/985,500, filed on Nov. 5, 2007, provisional application No. 60/905,703, filed on Mar. 8, 2007.

(51) Int. Cl.
*C07C 4/00* (2006.01)
*C07C 29/60* (2006.01)

(52) U.S. Cl. ........ 585/240; 585/242; 568/801; 568/861; 423/437.1

(58) Field of Classification Search .................. 585/241, 585/242; 568/861, 801; 44/605; 423/437.1
See application file for complete search history.

(56) References Cited

U.S. PATENT DOCUMENTS

| | | | |
|---|---|---|---|
| 2,965,679 A | 12/1960 | Conradin et al. |
| 3,894,107 A | 7/1975 | Butter et al. |
| 4,013,734 A | 3/1977 | Kim |
| 4,223,001 A | 9/1980 | Novotny et al. |
| 4,380,679 A | 4/1983 | Arena |
| 4,380,680 A | 4/1983 | Arena |
| 4,382,150 A | 5/1983 | Arena |
| 4,401,823 A | 8/1983 | Arena |
| 4,456,779 A | 6/1984 | Owen et al. |
| 4,476,331 A | 10/1984 | Dubeck et al. |
| 4,487,980 A | 12/1984 | Arena |
| 4,496,780 A | 1/1985 | Arena |
| 4,503,274 A | 3/1985 | Arena |

(Continued)

FOREIGN PATENT DOCUMENTS

CA    1201080 A1    2/1986

(Continued)

OTHER PUBLICATIONS

Gayubo et al., "Transformation of Oxygenate Components of Biomass Pyrolsis Oil on a HZSM-5 Zeolite. II. Aldehydes, Ketones, and Acids," Ind. Eng. Chem Res. 2004, 43:2619-2626.

(Continued)

*Primary Examiner* — N. Bhat
(74) *Attorney, Agent, or Firm* — Quarles & Brady LLP

(57) ABSTRACT

Processes and reactor systems are provided for the conversion of oxygenated hydrocarbons to hydrocarbons, ketones and alcohols useful as liquid fuels, such as gasoline, jet fuel or diesel fuel, and industrial chemicals. The process involves the conversion of mono-oxygenated hydrocarbons, such as alcohols, ketones, aldehydes, furans, carboxylic acids, diols, triols, and/or other polyols, to $C_{4+}$ hydrocarbons, alcohols and/or ketones, by condensation. The oxygenated hydrocarbons may originate from any source, but are preferably derived from biomass.

144 Claims, 19 Drawing Sheets

U.S. PATENT DOCUMENTS

| | | | |
|---|---|---|---|
| 4,541,836 A | 9/1985 | Derderian | |
| 4,543,435 A | 9/1985 | Gould et al. | |
| 4,554,260 A | 11/1985 | Pieters et al. | |
| 4,642,394 A | 2/1987 | Che | |
| 4,717,465 A | 1/1988 | Chen et al. | |
| 4,828,812 A | 5/1989 | McCullen et al. | |
| 4,885,421 A | 12/1989 | Harandi et al. | |
| 4,919,896 A | 4/1990 | Harandi et al. | |
| 4,935,568 A * | 6/1990 | Harandi et al. | 585/300 |
| 5,001,292 A | 3/1991 | Harandi et al. | |
| 5,006,131 A | 4/1991 | Karafian et al. | |
| 5,019,135 A | 5/1991 | Sealock, Jr. et al. | |
| 5,026,927 A | 6/1991 | Andrews et al. | |
| 5,095,159 A | 3/1992 | Harandi et al. | |
| 5,105,044 A | 4/1992 | Han et al. | |
| 5,130,101 A | 7/1992 | Harandi et al. | |
| 5,139,002 A | 8/1992 | Lynch et al. | |
| 5,149,884 A | 9/1992 | Brenner et al. | |
| 5,177,279 A | 1/1993 | Harandi | |
| 5,214,219 A | 5/1993 | Casale et al. | |
| 5,238,898 A | 8/1993 | Han et al. | |
| 5,306,847 A | 4/1994 | Gehrer et al. | |
| 5,326,912 A | 7/1994 | Gubitosa et al. | |
| 5,344,849 A | 9/1994 | Ayasse | |
| 5,354,914 A | 10/1994 | Gubitosa et al. | |
| 5,496,786 A | 3/1996 | Gubitosa et al. | |
| 5,504,259 A * | 4/1996 | Diebold et al. | 568/697 |
| 5,543,379 A | 8/1996 | Gubitosa et al. | |
| 5,578,647 A | 11/1996 | Li et al. | |
| 5,600,028 A | 2/1997 | Gubitosa et al. | |
| 5,616,154 A | 4/1997 | Elliott et al. | |
| 5,616,817 A | 4/1997 | Schuster et al. | |
| 5,635,145 A | 6/1997 | Den Hartog et al. | |
| 5,651,953 A | 7/1997 | Yokoyama et al. | |
| 5,660,602 A | 8/1997 | Collier, Jr. et al. | |
| 5,666,923 A | 9/1997 | Collier, Jr. et al. | |
| 5,787,864 A | 8/1998 | Collier, Jr. et al. | |
| 5,861,137 A | 1/1999 | Edlund | |
| 5,959,167 A | 9/1999 | Shabtai et al. | |
| 6,054,041 A | 4/2000 | Ellis et al. | |
| 6,059,995 A | 5/2000 | Topsoe et al. | |
| 6,152,975 A | 11/2000 | Elliott et al. | |
| 6,171,992 B1 | 1/2001 | Autenrieth et al. | |
| 6,172,272 B1 | 1/2001 | Shabtai et al. | |
| 6,207,132 B1 | 3/2001 | Lin et al. | |
| 6,235,797 B1 | 5/2001 | Elliot et al. | |
| RE37,329 E | 8/2001 | Gubitosa et al. | |
| 6,280,701 B1 | 8/2001 | Autenrieth et al. | |
| 6,291,725 B1 * | 9/2001 | Chopade et al. | 568/861 |
| 6,323,383 B1 | 11/2001 | Tsuchida et al. | |
| 6,361,757 B1 | 3/2002 | Shikada et al. | |
| 6,372,680 B1 * | 4/2002 | Wu et al. | 502/64 |
| 6,373,680 B1 | 4/2002 | Riskin | |
| 6,387,554 B1 | 5/2002 | Verykios | |
| 6,397,790 B1 | 6/2002 | Collier, Jr. | |
| 6,413,449 B1 | 7/2002 | Wieland et al. | |
| 6,429,167 B1 | 8/2002 | Maeno et al. | |
| 6,440,895 B1 | 8/2002 | Tonkovich et al. | |
| 6,479,428 B1 | 11/2002 | Tonkovich et al. | |
| 6,479,713 B1 | 11/2002 | Werpy et al. | |
| 6,486,366 B1 | 11/2002 | Ostgard et al. | |
| 6,508,209 B1 | 1/2003 | Collier, Jr. | |
| 6,570,043 B2 | 5/2003 | Elliott et al. | |
| 6,582,667 B1 | 6/2003 | Ogata et al. | |
| 6,607,707 B2 | 8/2003 | Reichman et al. | |
| 6,670,300 B2 | 12/2003 | Werpy et al. | |
| 6,677,385 B2 | 1/2004 | Werpy et al. | |
| 6,699,457 B2 | 3/2004 | Cortright et al. | |
| 6,739,125 B1 | 5/2004 | Mulligan | |
| 6,749,828 B1 | 6/2004 | Fukunaga | |
| 6,762,149 B2 | 7/2004 | Tonkovich et al. | |
| 6,765,101 B1 | 7/2004 | Bhasin et al. | |
| 6,841,085 B2 | 1/2005 | Werpy et al. | |
| 6,953,873 B2 * | 10/2005 | Cortright et al. | 585/733 |
| 6,964,757 B2 * | 11/2005 | Cortright et al. | 423/648.1 |
| 6,964,758 B2 | 11/2005 | Cortright et al. | |
| 6,969,506 B2 | 11/2005 | Tonkovich et al. | |
| 6,982,328 B2 | 1/2006 | Werpy et al. | |
| 7,022,824 B2 | 4/2006 | Vanoppen et al. | |
| 7,038,094 B2 | 5/2006 | Werpy et al. | |
| 7,070,745 B2 | 7/2006 | Van Der Moor et al. | |
| 7,112,312 B2 | 9/2006 | Chou | |
| 7,186,668 B2 | 3/2007 | Werpy et al. | |
| 7,199,250 B2 | 4/2007 | Werpy et al. | |
| 7,232,935 B2 | 6/2007 | Jakkula et al. | |
| 7,273,957 B2 | 9/2007 | Bakshi et al. | |
| 7,288,685 B2 | 10/2007 | Marker | |
| 7,297,814 B2 | 11/2007 | Yada et al. | |
| 7,355,083 B2 | 4/2008 | Tuck et al. | |
| 7,578,927 B2 * | 8/2009 | Marker et al. | 208/67 |
| 7,663,004 B2 | 2/2010 | Suppes et al. | |
| 7,692,001 B2 | 4/2010 | Holcomb | |
| 7,767,867 B2 * | 8/2010 | Cortright | 568/861 |
| 2003/0099593 A1 | 5/2003 | Cortright et al. | |
| 2003/0100807 A1 | 5/2003 | Shabtai et al. | |
| 2003/0115792 A1 | 6/2003 | Shabtai et al. | |
| 2003/0175561 A1 | 9/2003 | Lightner | |
| 2005/0064560 A1 | 3/2005 | Werpy et al. | |
| 2005/0065337 A1 | 3/2005 | Werpy et al. | |
| 2005/0203195 A1 | 9/2005 | Wang et al. | |
| 2005/0207971 A1 | 9/2005 | Cortright et al. | |
| 2005/0244329 A1 | 11/2005 | Casanave et al. | |
| 2005/0271579 A1 | 12/2005 | Rogers | |
| 2006/0013759 A1 | 1/2006 | Jiang et al. | |
| 2006/0024539 A1 | 2/2006 | Dumesic et al. | |
| 2007/0123739 A1 | 5/2007 | Crabtree et al. | |
| 2007/0135301 A1 | 6/2007 | Holcomb, Jr. | |
| 2007/0173643 A1 | 7/2007 | Werpy et al. | |
| 2007/0173651 A1 | 7/2007 | Holladay et al. | |
| 2007/0173652 A1 | 7/2007 | Holladay et al. | |
| 2008/0216391 A1 | 9/2008 | Cortright et al. | |
| 2008/0300434 A1 | 12/2008 | Cortright et al. | |
| 2008/0300435 A1 | 12/2008 | Cortright et al. | |
| 2009/0211942 A1 | 8/2009 | Cortright et al. | |
| 2010/0076233 A1 | 3/2010 | Cortright et al. | |

FOREIGN PATENT DOCUMENTS

| | | |
|---|---|---|
| EP | 0204354 A | 12/1986 |
| EP | 0323663 B2 | 9/1994 |
| EP | 1454671 A | 9/2004 |
| EP | 1724325 A | 11/2006 |
| FR | 2857003 | 1/2005 |
| GB | 2097390 A | 11/1982 |
| JP | 2004344721 A | 12/2004 |
| WO | 9910450 A | 3/1999 |
| WO | 9961369 A | 12/1999 |
| WO | WO 03/045841 | 6/2003 |
| WO | 2005037423 A | 4/2005 |
| WO | 2006100584 A | 9/2006 |
| WO | WO 2006/119357 | 11/2006 |
| WO | 2007027832 | 3/2007 |
| WO | 2007053705 | 5/2007 |
| WO | WO 2007/075476 | 7/2007 |
| WO | 2007099161 | 9/2007 |
| WO | 2008109877 | 12/2008 |

OTHER PUBLICATIONS

Agar Prof. David, "Abstract 2254—Influence of the Liquid Phase Physical Properties on Unsteady-State Hydrodynamics in Periodically Operated Tricke-Bed Reactors," European Congress of Chemical Engineering—6, Copenhagen Sep. 2007.

Chaminand et al., 2004 Green Chemistry, 6(8) pp. 359-361 (abstract only).

Chiu et al., "Removal of Residual Catalyst from Simulated Biodiesel's Crude Glycerol for Glycerol Hydrogenolysis to Propylene Glycol" 2006 Ind. Eng. Chem. Res 45:791-795.

Crabtree, S.P., et. al., "Novel Catalysis for Glycol Manufacture" 2001.

Davda et al., "A review of catalytic issues and process conditions for renewable hydrogen and alkanes by aqueous-phase reforming of oxygenated hydrocarbons over supported metal catalysts" 2005 Appl. Catal. B:Environmental 56:171-186.

Davda et al., "Catalytic Reforming of Oxygenated Hydrocarbons for Hydrogen with Low Levels of Carbon Monoxide" 2003 Agnew. Chem. Int. Ed., 42:4068-4071.

Davda et al., "Renewable hydrogen by aqueous-phase reforming of glucose" 2004 Chem. Commun., 36-37.
Elliot et al., "Chemical Processing in High-Pressure Aqueous Environments. 7. Process Development for Catalytic Gasification of Wet Biomass Feedstocks" 2004 Ind. Eng. Chem. Res. 43:1999-2004.
Huber et al., "Production of Liquid Alkanes by Aqueous-Phase Processing of Biomass-Derived Carbohydrates" 2005 Science 308:1446-1450.
Huber et al., "Renewable Alkanes by Aqueoud-Phase Reforming of Biomass-Derived Oxygenates" 2004 Agnew. Chem. Int. Ed., 43:1549-1551.
Miyazawa et al., "Glycerol conversion in the aqueous solution under hydrogen over RuIC + an ion-exchange resin and its reaction mechanism" 2006 J. of Catalysis 240:213-221.
Shabaker et al., "Aqueous-phase reforming of ethylene glycol over supported platinum catalysts" Catal. Lett., May 2003, vol. 88, Nos. 1-2.
Shabaker et al., "Sn-modified catalysts for aqueous-phase reforming: Characterization and deactivation studies" 2005 J.Catal., 231:67-76.
Shabaker JW et al., "Kinetics of Aqueous-Phase Reforming of Oxygenated Hydrocarbons: PUAI2O3 and Sn-Modified Ni Catalysts" 2004 Ind. Eng, Chem. Res., 43:3105-3112.
United States Patent and Trademark Office, Office Action Summary and Detailed Action, U.S. Appl. No. 11/800,671, Dec. 26, 2008.
Applicant, Response to Restriction Requirement, U.S. Appl. No. 11/800,671, Jan. 26, 2009.
United States Patent and Trademark Office, Office Action Summary and Detailed Action, U.S. Appl. No. 11/800,671, Apr. 8, 2009.
Applicant, Response to Non-Final Office Action, U.S. Appl. No. 11/800,671, Aug. 10, 2009.
United States Patent and Trademark Office, Issue Notification, U.S. Appl. No. 11/800,671, Aug. 3, 2010.
United States Patent and Trademark Office, Office Action Summary and Detailed Action, U.S. Appl. No. 12/158,635, Jan. 4, 2011.
United States Patent and Trademark Office, Office Action Summary and Detailed Action, U.S. Appl. No. 12/044,837, Aug. 12, 2010.
United States Patent and Trademark Office, Interview Summary, U.S. Appl. No. 12/044,837, Oct. 28, 2010.
Applicant, Response to Non-Final Office Action, U.S. Appl. No. 12/044,837, Nov. 12, 2010.
Applicant, Supplemental Response to Non-Final Office Action, U.S. Appl. No. 12/044,837, Jan. 4, 2011.
United States Patent and Trademark Office, Office Action Summary and Detailed Action, U.S. Appl. No. 12/044,876, Aug. 16, 2010.
United States Patent and Trademark Office, Interview Summary, U.S. Appl. No. 12/044,876, Oct. 28, 2010.
Applicant, Response to Non-Final Office Action, U.S. Appl. No. 12/044,876, Nov. 12, 2010.
Applicant, Supplemental Response to Non-Final Office Action, U.S. Appl. No. 12/044,876, Jan. 5, 2011.
United States Patent and Trademark Office, Office Action Summary and Detailed Action, U.S. Appl. No. 12/834,306, Sep. 17, 2010.
Applicant, Response to Non-Final Office Action, U.S. Appl. No. 12/834,306, Dec. 15, 2010.
PCT International Search Report, Application No. PCT/US2007/011062, Sep. 16, 2008.
PCT International Preliminary Report on Patentability, Application No. PCT/US2007/011062, Nov. 11, 2008.
European Patent Office, Examination Report, Application No. 07870663.7, Oct. 22, 2010.
Ukraine Patent Office, Office Action, Application No. a 2008 12327, 2010.
Republic of South Africa, Letters Patent, Patent No. 2008/09194, Dec. 30, 2009.
Intellectual Property Office of New Zealand, Examination Report, Application No. 572113, Jun. 4, 2010.
PCT International Search Report, Application No. PCT/US2006/048040, May 10, 2007.
PCT International Preliminary Report on Patentability, Application No. PCT/US2006/048040, Jun. 24, 2008.
State Intellectual Property Office of the People's Republic of China, First Office Action (Translation), Application No. 200680048598.5, Jun. 11, 2010.

Applicant, Response to State Intellectual Property Office of the People's Republic of China First Office Action, Oct. 21, 2010 [includes AFD China Intellectual Property Law Office Oct. 22, 2010 letter; Quarles & Brady Oct. 13, 2010 letter; English version of Amended Claims].
State Intellectual Property Office of the People's Republic of China, Second Office Action (Translation), Application No. 200680048598. 5, Jan. 10, 2011.
Patent Office of the Russian Federation, Office Action (Inquiry) of the State Examination, Applicaiton No. 2008127066, Nov. 15, 2010.
Ukraine Patent Office, Office Action, Application No. a 2008 09306, 2010.
Applicant, Response to Ukraine Patent Office Office Action, Application No. a 2008 09306, Dec. 2010 [includes Papula-Nevinpat Dec. 8, 2010 letter].
Ukraine Patent Office, Office Action, Application No. a 2008 09306, Jan. 2011.
Intellectual Property Office of New Zealand, Examination Report, Application No. 569246, Mar. 2, 2010.
PCT International Search Report and Written Opinion, Application No. PCT/US2007/088417, Dec. 2, 2008.
PCT International Preliminary Report on Patentability, Application No. PCT/US2007/088417, Jun. 24, 2009.
Intellectual Property Office of New Zealand, Examination Report, Application No. 577547, Sep. 17, 2010.
Republic of South Africa, Letters Patent, Patent No. 2009/04056, Apr. 28, 2010.
Badger, P.C., "Ethanol From cellulose: A General Review," Ethanol From cellulose: A General Review p. 17-21 (2002).
Bardin, B.B., et al., "Acidity of Keggin-Type Heteropolycompounds Evaluated by Catalytic Probe Reactions, Sorption Microcalorimetry, and Density Functional quantum Chemical Calculations," J. Phys. Chem. B 102-10817-10825 (1998).
Barrett, C.J., et al., "Single-reactor process for sequential aldol-condensation and hydrogenation of biomass-derived compounds in water," Applied catalysis B: environmental 66:111-118 (2006).
Brown, N.F., et al., "Carbon-Halogen Bond Scission and Rearrangement of Beta-Halohydrins on the Rh(111) Surface," J. Phys. Chem. 98:12737-12745 (1994).
Chen, N.Y., et al., "Liquid fuel from carbohydrates," Chemtech Aug. 1985 p. 506-509.
Chiu, C-W, et al., "Distribution of Methanol and Catalysts between Biodiesel and Glycerin Phases," AIChE Journal 51:1274-1278 (2005).
Corma, A., et al., "Processing biomass-derived oxygenates in the oil refinery: Catalytic cracking (FCC) reaction pathways and role of catalyst," J. of Catalysis 247:307-327 (2007).
Cartright, R.D., et al., "Hydrogen from catalytic reforming of biomass-derived hydrocarbons in liquid water," Nature 418:964-967 (2002).
Dasari, M.A., et al., "Low-pressure hydrogenolysis of glycerol to propylene glycol," Applied Catalysis A: General 281:225-231 (2005).
Dass, D.V., et al., "A comparative study of the conversion of ethanol and of ethylene over the "Mobil" zeolite catalyst, H-ZSM-5. An application of the Benzene Sequestration Test," Can. J. Chem. 67:1732-1734 (1989).
Davda, R.R., et al., "Aqueous-phase reforming of ethylene glycol on silica-supported metal catalysts," Applied Catalysis B: Environment 43:13-26 (2003).
dos Santos, S.M., et al., "Performance of RuSn catalysts supported on different oxides in the selective hydrogenation of dimethyl adipate," Catalysis Today 107-108:250-257 (2005).
Elliott, D.C., et al., "Liquid Fuels by Low-Severity Hydrotreating of Biocrude," Developments in Thermochemical Biomass Conversion 1:611-621 (1996).
Elliott, D.C., et al., "Chemical Processing in High-Pressure Aqueous Environments. 6. Demonstration of Catalytic Gasification for Chemical Manufacturing Wastewater Cleanup in Industrial Plants," Ind. Eng. chem. Res. 38:879-883 (1999).
Fraser, J., "Roadmap for Cellulosic Ethanol Production", http://energy.sekingalpha.com/article/13457, Aug. 1, 2006.

Fukuoka, A., et al., "Catalytic Conversion of cellulose into Sugar Alcohols," Angew. Chem. Int. Ed. 5:5161-5163 (2006).

Gayubo, A.G., et al., "Transformation of Oxygenate Components of Biomass Pyrolysis Oil on a HZSM-5 Zeolite. I. Alcohols and Phenols," Ind. Eng. Chem. Res. 43:2610-2618 (2004).

Greer, D., "Creating Cellulosic Ethanol: Spinning Straw into Fuel," May 2005 eNews Bulletin.

Huber, G.W., et al., "Raney Ni—Sn catalyst for H2 Production from Biomass-Derived Hydrocarbons," Science 300:2075-2077 (2003).

Huber, G.W., et al., "Synthesis of Transportation Fuels from Biomass: Chemistry, Catalysts, and Engineering," Chem. Rev. 106:4044-4098 (2006).

Kawai, M., et al.,"Production of Hydrogen and Hydrocarbon From Cellulose and Water," Chemistry Letters p. 1185-1188 (1981).

Kluson, P., et al., "Selective Hydrogenation over Ruthenium Catalysts," Applied Catalysis A: General 128:13-31 (1995).

Makarova, M.A., et al., "Dehydration of n-Butanol on Zeolite H-ZSM-5 and Amorphous Aluminosilicate: Detailed Mechanistic Study and the Effect of Pore Confinement," Journal of Catalysis 149:36-51 (1994).

Minowa, T., et al., "Hydrogen Production from Wet Cellulose by Low Temperature Gasification Using a Reduced Nickel Catalyst," Chemistry Letters p. 937-938 (1995).

Minowa, T., et al., "Hydrogen Production from Cellulose in Hot Compressed Water Using Reduced Nickel Catalyst: Product Distribution at Different Reaction Temperature," J. of Chem. Eng. of Japan 31:488-491 (1998).

Nelson, D.A., et al., Application of Direct Thermal liquefaction for the Conversion of Cellulosic Biomass, Ind. Eng. Chem. Prod. Res. Dev. 23:471-475 (1984).

Oregon Cellulose-Ethanol Study, "Appendix B—Overview of Cellulose-Ethanol Production Technology," p. 57-60.

Roman-Leshkov, Y., et al., "Production of dimethylfuran for liquid fuels from biomass-derived carbohydrates," Nature 447:982-986 (2007).

Rostrup-Nielsen, J.R., "Conversion of hydrocarbons and alcohols for fuel cells," Phys. Chem. Chem. Phys. 3:283-288 (2001).

Shabaker, J.W., et al., "Aqueous-phase reforming of methanol and ethylene glycol over alumina-supported platinum catalysts," Journal of Catalysis 215:344-352 (2003).

Shabaker, J.W., et al., "Aqueous-phase reforming of oxygenated hydrocarbons over Sn-modified Ni catalysts," Journal of Catalysis 222:180-191 (2004).

Silva, A.M., et al., "Role of catalyst preparation on determining selective sites for hydrogenation of dimethyl adipate over RuSn/Al2O3," J. of Molecular Catalysis A: Chemical 253:62-69 (2006).

Tsuchida, t., et al., "Direct Synthesis of n-Butanol from Ethanol over Nonstoichiometric Hydroxyapatite," Ind. Eng. Chem. Res. 45:8634-9642 (2006).

Wang, D., et al., "Catalytic steam reforming of biomass-derived oxygenates: acetic acid and hydroxyacetaldehyde," Applied Catalysis A: General 143:245-270 (1996).

Werpy, T., et al., "Top Value Added Chemicals from Biomass vol. 1—Results of Screening for Potential Candidates from Sugars and Synthesis Gas," 2004.

Yoshida, T., et al., "Gasification of Cellulose, Xylan, and Lignin Mixtures in Supercritical Water," Ind. Eng. Chem. Res. 40:5469-5474 (2001).

PCT International Search Report, Application No. PCT/US2008/056330, Jul. 10, 2008.

PCT International Preliminary Report on Patentability, PCT/US2008/056330, Sep. 8, 2009.

European Patent Office, Communication, Application No. 08731758.2, Apr. 2, 2009.

Applicant, Response to European Patent Office Apr. 2, 2009 Communication, Application No. 08731758.2, May 1, 2009.

European Patent Office, Communication, Application No. 08731758.2, Mar. 25, 2010.

Applicant, Response to European Patent Office Mar. 25, 2010, Communication, Application No. 08731758.2, Oct. 1, 2010.

Intellectual Property Office of New Zealand, Examination Report, Application No. 579525, Sep. 29, 2010.

Republic of South Africa, Letters Patent, Patent No. 2009/05916, Apr. 28, 2010.

PCT International Search Report and Written Opinion, Application No. PCT/US2010/040644, Feb. 4, 2011.

* cited by examiner

SYNTHESIS OF LIQUID FUELS AND CHEMICALS FROM OXYGENATED HYDROCARBONS

CROSS REFERENCE TO RELATED APPLICATIONS

This application claims benefit of U.S. Provisional Application Nos. 60/985,475 filed on Nov. 5, 2007, 60/985,500 filed on Nov. 5, 2007, and, 60/905,703 filed on Mar. 8, 2007.

Commonly owned U.S. Nonprovisional application Ser. No. 11/961,280 filed on Dec. 20, 2007, discloses related subject matter.

Commonly owned U.S. Nonprovisional application Ser. No. 11/800,671 filed on May 7, 2007, now U.S. Pat. No. 7,767,867 discloses related subject matter.

Commonly owned PCT Application No. PCT/US06/048030 filed on Dec. 18, 2006, discloses related subject matter.

BACKGROUND

Significant amount of attention has been placed on developing new technologies for providing energy from resources other than fossil fuels. Biomass is a resource that shows promise as a fossil fuel alternative. As opposed to fossil fuel, biomass is also renewable.

One type of biomass is plant biomass. Plant biomass is the most abundant source of carbohydrate in the world due to the lignocellulosic materials composing the cell walls in higher plants. Plant cell walls are divided into two sections, primary cell walls and secondary cell walls. The primary cell wall provides structure for expanding cells and is composed of three major polysaccharides (cellulose, pectin, and hemicellulose) and one group of glycoproteins. The secondary cell wall, which is produced after the cell has finished growing, also contains polysaccharides and is strengthened through polymeric lignin covalently cross-linked to hemicellulose. Hemicellulose and pectin are typically found in abundance, but cellulose is the predominant polysaccharide and the most abundant source of carbohydrates.

Most transportation vehicles, whether boats, trains, planes and automobiles, require high power density provided by internal combustion and/or propulsion engines. These engines require clean burning fuels which are generally in liquid form or, to a lesser extent, compressed gases. Liquid fuels are more portable due to their high energy density and their ability to be pumped, which makes handling easier. This is why most fuels are liquids.

Currently, biomass provides the only renewable alternative for liquid transportation fuel. Unlike nuclear and wind applications, and for the most part solar resources, biomass is capable of being converted into a liquid form. Unfortunately, the progress in developing new technologies for producing liquid biofuels has been slow in developing, especially for liquid fuel products that fit within the current infrastructure. Although a variety of fuels can be produced from biomass resources, such as ethanol, methanol, biodiesel, Fischer-Tropsch diesel, and gaseous fuels, such as hydrogen and methane, these fuels require either new distribution technologies and/or combustion technologies appropriate for their characteristics. The production of these fuels also tend to be expensive and raise questions with respect to their net carbon savings.

Ethanol, for example, is made by converting the carbohydrate from biomass into sugar, which is then converted into ethanol in a fermentation process similar to brewing beer. Ethanol is the most widely used biofuel today with current capacity of 4.3 billion gallons per year based on starch crops, such as corn. Ethanol, however, has very substantial disadvantages with respect its energy value as a fuel relative to the amount of energy needed to produce it. Ethanol produced by fermentation contains large amounts of water, typically comprising only about 5 percent of ethanol by volume in the water/alcohol fermentation product. The removal of this water is highly energy-consuming, and often requires the use of natural gas as a heat source. Ethanol also has less energy content than gasoline, which means that it takes more fuel to go the same distance. Ethanol is very corrosive to fuel systems and cannot be transported in petroleum pipelines. As a result, ethanol is transported over-the-road in tank trucks, which increases its overall cost and energy consumption. When considering the total energy consumed by farm equipment, cultivation, planting, fertilizers, pesticides, herbicides, petroleum-based fungicides, irrigation systems, harvesting, transportation to processing plants, fermentation, distillation, drying, transport to fuel terminals and retail pumps, and lower ethanol fuel energy content, the net energy content value added and delivered to consumers is very small.

Biodiesel is another potential energy source. Biodiesel can be made from vegetable oil, animal fats, waste vegetable oils, microalgae oils or recycled restaurant greases, and is produced through a process in which organically derived oils are combined with alcohol (ethanol or methanol) in the presence of a catalyst to form ethyl or methyl ester. The biomass-derived ethyl or methyl esters can then be blended with conventional diesel fuel or used as a neat fuel (100% biodiesel). Biodiesel is also expensive to manufacture, and poses various issues in its use and combustion. For example, biodiesel is not suitable for use in lower temperatures and requires special handling to avoid gelling in cold temperatures. Biodiesel also tends to provide higher nitrogen oxide emissions, and cannot be transported in petroleum pipelines.

Biomass can also be gasified to produce a synthesis gas composed primarily of hydrogen and carbon monoxide, also called syngas or biosyngas. Syngas produced today is used directly to generate heat and power, but several types of biofuels may be derived from syngas. Hydrogen can be recovered from syngas, or it can be catalytically converted to methanol. The gas can also be run through a biological reactor to produce ethanol or converted using Fischer-Tropsch catalyst into a liquid stream with properties similar to diesel fuel, called Fischer-Tropsch diesel. These processes are expensive and generate fuels that are not easily assimilated in current transportation technology. Processes capable of converting biomass using catalytic techniques would be especially advantageous due to its familiarity within the current fuel industry.

SUMMARY OF THE INVENTION

The invention provides methods, reactor systems and catalysts for producing $C_{4+}$ compounds (e.g., $C_{4+}$ alcohols, $C_{4+}$ ketones, $C_{4+}$ alkanes, $C_{4+}$ alkenes, $C_{5+}$ cycloalkanes, $C_{5+}$ cycloalkenes, aryls, fused aryls, and mixtures thereof) from oxygenated hydrocarbons. In one embodiment, the method involves (1) catalytically reacting, in an aqueous liquid phase and/or a vapor phase, $H_2$ and water soluble oxygenated hydrocarbons comprising a $C_{1+}O_{1+}$ hydrocarbon in the presence of a deoxygenation catalyst at a deoxygenation temperature and deoxygenation pressure to produce an oxygenate comprising a $C_{1+}O_{1-3}$ hydrocarbon; and (2) catalytically reacting in the liquid and/or vapor phase the oxygenate in the presence of a condensation catalyst at a condensation temperature and condensation pressure to produce the $C_{4+}$ compound. The hydrogen may be in situ generated $H_2$, external $H_2$, supplemental $H_2$, or a combination thereof.

One aspect of the invention is a method of making a $C_{4+}$ compound comprising the steps or acts of providing water and a water soluble oxygenated hydrocarbon comprising a $C_{1+}O_{1+}$ hydrocarbon in an aqueous liquid phase and/or a vapor phase, providing $H_2$, catalytically reacting in the liquid and/or vapor phase the oxygenated hydrocarbon with the $H_2$ in the presence of a deoxygenation catalyst at a deoxygenation temperature and deoxygenation pressure to produce an oxygenate comprising a $C_{1+}O_{1-3}$ hydrocarbon in a reaction stream, and catalytically reacting in the liquid and/or vapor phase the oxygenate in the presence of a base catalyst at a condensation temperature and condensation pressure to produce the $C_{4+}$ compound, wherein the $C_{4+}$ compound comprises a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and a mixture thereof.

In one exemplary embodiment, the $H_2$ comprises in situ generated $H_2$, external $H_2$, recycled $H_2$, or a combination thereof. In another exemplary embodiment, the $H_2$ comprises in situ generated $H_2$ produced by catalytically reacting in a liquid phase and/or vapor phase a portion of the water and oxygenated hydrocarbon in the presence of an aqueous phase reforming catalyst at a reforming temperature and reforming pressure to produce in situ generated $H_2$. In another exemplary embodiment, the step of catalytically reacting the oxygenated hydrocarbon with $H_2$ in the presence of the deoxygenation catalyst is conducted in the presence of an insignificantly effective amount of external $H_2$. In another exemplary embodiment, the molar ratio of the total oxygen atoms in the oxygenated hydrocarbons to the total hydrogen atoms in the external $H_2$ is less than 1:1.

The oxygenated hydrocarbons may be any water-soluble oxygenated hydrocarbon having one or more carbon atoms and at least one oxygen atom ($C_{1+}O_{1+}$ hydrocarbons). In one exemplary embodiment, the oxygenated hydrocarbon comprises polysaccharides, disaccharides, monosaccharides, cellulose derivatives, lignin derivatives, hemicellulose, sugars, sugar alcohols or a mixture thereof. In another exemplary embodiment, the oxygenated hydrocarbon comprises a $C_{1-12}O_{1-11}$ hydrocarbon, or a $C_{1-6}O_{1-6}$ hydrocarbon. In yet another exemplary embodiment, the $C_{1-12}O_{1-11}$ hydrocarbon comprises a sugar alcohol, sugar, monosaccharide, disaccharide, alditol, cellulosic derivative, lignocellulosic derivative, glucose, fructose, sucrose, maltose, lactose, mannose, xylose, arabitol, erythritol, glycerol, isomalt, lactitol, malitol, mannitol, sorbitol, xylitol, or a mixture thereof. In another exemplary embodiment, the oxygenated hydrocarbon further comprises recycled $C_{1+}O_{1+}$ hydrocarbon.

The oxygenates may be any hydrocarbon having 1 or more carbon atoms and between 1 and 3 oxygen atoms (referred to herein as $C_{1+}O_{1-3}$ hydrocarbons). In one exemplary embodiment, the oxygenate comprises an alcohol, ketone, aldehyde, furan, diol, triol, hydroxy carboxylic acid, carboxylic acid, or a mixture thereof. In another exemplary embodiment, the oxygenate comprises methanol, ethanol, n-propyl alcohol, isopropyl alcohol, butyl alcohol, pentanol, hexanol, cyclopentanol, cyclohexanol, 2-methylcyclopentanol, hydroxyketones, cyclic ketones, acetone, propanone, butanone, pentanone, hexanone, 2-methyl-cyclopentanone, ethylene glycol, 1,3-propanediol, propylene glycol, butanediol, pentanediol, hexanediol, methylglyoxal, butanedione, pentanedione, diketohexane, hydroxyaldehydes, acetaldehyde, propionaldehyde, butyraldehyde, pentanal, hexanal, formic acid, acetic acid, propionic acid, butanoic acid, pentanoic acid, hexanoic acid, lactic acid, glycerol, furan, tetrahydrofuran, dihydrofuran, 2-furan methanol, 2-methyl-tetrahydrofuran, 2,5-dimethyl-tetrahydrofuran, 2-ethyl-tetrahydrofuran, 2-methyl furan, 2,5-dimethyl furan, 2-ethyl furan, hydroxylmethylfurfural, 3-hydroxytetrahydrofuran, tetrahydro-3-furanol, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, and hydroxymethyltetrahydrofurfural, isomers thereof, or combinations thereof. In yet another exemplary embodiment, the oxygenate further comprises recycled $C_{1+}O_{1-3}$ hydrocarbon.

The $C_{4+}$ compound comprises a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and a mixture thereof. In one exemplary embodiment, the $C_{4+}$ alkane comprises a branched or straight chain $C_{4-30}$ alkane, or a branched or straight chain $C_{4-9}$, $C_{7-14}$, $C_{12-24}$ alkane, or a mixture thereof. In another exemplary embodiment, the $C_{4+}$ alkene comprises a branched or straight chain $C_{4-30}$ alkene, or a branched or straight chain $C_{4-9}$, $C_{7-14}$, $C_{12-24}$ alkene, or a mixture thereof. In another exemplary embodiment, the $C_{5+}$ cycloalkane comprises a mono-substituted or multi-substituted $C_{5+}$ cycloalkane, and at least one substituted group is a branched $C_{3+}$ alkyl, a straight chain $C_{1+}$ alkyl, a branched $C_{3+}$ alkylene, a straight chain $C_{1+}$ alkylene, a phenyl, or a combination thereof, or a branched $C_{3-12}$ alkyl, a straight chain $C_{1-12}$ alkyl, a branched $C_{3-12}$ alkylene, a straight chain $C_{1-12}$ alkylene, a phenyl, or a combination thereof, or a branched $C_{3-4}$ alkyl, a straight chain $C_{1-4}$ alkyl, a branched $C_{3-4}$ alkylene, straight chain $C_{1-4}$ alkylene, a phenyl, or a combination thereof. In another exemplary embodiment, the $C_{5+}$ cycloalkene comprises a mono-substituted or multi-substituted $C_{5+}$ cycloalkene, and at least one substituted group is a branched $C_{3+}$ alkyl, a straight chain $C_{1+}$ alkyl, a branched $C_{3+}$ alkylene, a straight chain $C_{2+}$ alkylene, a phenyl, or a combination thereof, or a branched $C_{3-12}$ alkyl, a straight chain $C_{1-12}$ alkyl, a branched $C_{3-12}$ alkylene, a straight chain $C_{2-12}$ alkylene, a phenyl, or a combination thereof, or a branched $C_{3-4}$ alkyl, a straight chain $C_{1-4}$ alkyl, a branched $C_{3-4}$ alkylene, straight chain $C_{2-4}$ alkylene, a phenyl, or a combination thereof. In another exemplary embodiment, the aryl comprises an unsubstituted aryl, or a mono-substituted or multi-substituted aryl, and at least one substituted group is a branched $C_{3+}$ alkyl, a straight chain $C_{1+}$ alkyl, a branched $C_{3+}$ alkylene, a straight chain $C_{2+}$ alkylene, a phenyl, or a combination thereof, or a branched $C_{3-12}$ alkyl, a straight chain $C_{1-12}$ alkyl, a branched $C_{3-12}$ alkylene, a straight chain $C_{2-12}$ alkylene, a phenyl, or a combination thereof, or a branched $C_{3-4}$ alkyl, a straight chain $C_{1-4}$ alkyl, a branched $C_{3-4}$ alkylene, a straight chain $C_{2-4}$ alkylene, a phenyl, or a combination thereof. In another exemplary embodiment, the fused aryl comprises an unsubstituted fused aryl, or a mono-substituted or multi-substituted fused aryl, and at least one substituted group is a branched $C_{3+}$ alkyl, a straight chain $C_{1+}$ alkyl, a branched $C_{3+}$ alkylene, a straight chain $C_{2+}$ alkylene, a phenyl, or a combination thereof, or a branched $C_{3-4}$ alkyl, a straight chain $C_{1-4}$ alkyl, a branched $C_{3-4}$ alkylene, a straight chain $C_{2-4}$ alkylene, a phenyl, or a combination thereof. In another exemplary embodiment, the $C_{4+}$ alcohol comprises a compound according to the formula $R^1$—OH, wherein $R^1$ is a branched $C_{4+}$ alkyl, straight chain $C_{4+}$ alkyl, a branched $C_{4+}$ alkylene, a straight chain $C_{4+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl, or a combination thereof.

In another exemplary embodiment of method of making the $C_{4+}$ compound, the $C_{4+}$ ketone comprises a compound according to the formula

wherein $R^3$ and $R^4$ are independently a branched $C_{3+}$ alkyl, a straight chain $C_{1+}$ alkyl, a branched $C_{3+}$ alkylene, a straight chain $C_{2+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl, or a combination thereof.

The base catalyst will generally be a basic catalyst capable of forming longer chain compounds by linking two oxygen containing species through a new carbon-carbon bond, and converting the resulting compound to a hydrocarbon, alcohol or ketone. In one exemplary embodiment, the base catalyst comprises hydrotalcite, zinc-aluminate, phosphate, Li, Na, K, Cs, B, Rb, Mg, Ca, Sr, Si, Ba, Al, Ce, La, Sc, Y, Zr, Ti, Zn, an alloy thereof, or a combination thereof. In another exemplary embodiment, the base catalyst further comprises an oxide of Ti, Zr, V, Nb, Ta, Mo, Cr, W, Mn, Re, Al, Ga, In, Fe, Co, Mg, Ni, Si, Cu, Zn, Sn, Cd, P, or a combination thereof. In another exemplary embodiment, the base catalyst further comprises a metal being Cu, Ag, Au, Pt, Ni, Fe, Co, Ru, Zn, Cd, Ga, In, Rh, Pd, Ir, Re, Mn, Cr, Mo, W, Sn, Os, an alloy thereof, or a combination thereof. In another exemplary embodiment, the base catalyst comprises a metal oxide of Cu, Ni, Zn, V, Zr, and a combination thereof. In another exemplary embodiment, the base catalyst comprises zinc aluminate and a metal being Pd, Pt, Ni, Cu, or a combination thereof.

The deoxygenation catalyst is preferably a heterogeneous catalyst having one or more materials capable of catalyzing a reaction between hydrogen and the oxygenated hydrocarbon to remove one or more of the oxygen atoms from the oxygenated hydrocarbon to produce alcohols, ketones, aldehydes, furans, carboxylic acids, hydroxy carboxylic acids, diols and triols. In one exemplary embodiment, the deoxygenation catalyst comprises a support and Re, Cu, Fe, Ru, Ir, Co, Rh, Pt, Pd, Ni, W, Os, Mo, Ag, Au, an alloy thereof, or a combination thereof. In another exemplary embodiment, the deoxygenation catalyst further comprises Mn, Cr, Mo, W, V, Nb, Ta, Ti, Zr, Y, La, Sc, Zn, Cd, Ag, Au, Sn, Ge, P, Al, Ga, In, Tl, or a combination thereof. In one exemplary embodiment, the support comprises a nitride, carbon, silica, alumina, zirconia, titania, vanadia, ceria, boron nitride, heteropolyacid, kieselguhr, hydroxyapatite, zinc oxide, chromia, or a mixture thereof. In another exemplary embodiment, the support is a hydrogen peroxide treated carbon. In another exemplary embodiment, the support is modified by treating the support with a modifier being silanes, alkali compounds, alkali earth compounds, or lanthanides. In another exemplary embodiment, the support comprises carbon nanotubes, carbon fullerenes, and zeolites. In another exemplary embodiment, the deoxygenation catalyst and the condensation catalyst are atomically identical.

The APR catalyst is preferably a heterogeneous catalyst capable of catalyzing the reaction of water and oxygenated hydrocarbons to form $H_2$. In one exemplary embodiment, the aqueous phase reforming catalyst comprises a support and Fe, Ru, Os, Ir, Co, Rh, Pt, Pd, Ni, an alloy thereof, or a combination thereof. In another exemplary embodiment, the aqueous phase reforming catalyst further comprises Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, an alloy thereof, or a combination thereof. In another exemplary embodiment, the support comprises any one of the above supports described for the deoxygenation catalyst. In another exemplary embodiment, one or more of the aqueous phase reforming catalyst, deoxygenation catalyst, and condensation catalyst are atomically identical. In yet another exemplary embodiment, the aqueous phase reforming catalyst and deoxygenation catalyst comprise Pt alloyed or admixed with Ni, Ru, Cu, Fe, Rh, Re, alloys thereof, or a combination thereof. In another exemplary embodiment, the aqueous phase reforming catalyst and deoxygenation catalyst comprise Ru alloyed or admixed with Ge, Bi, B, Ni, Sn, Cu, Fe, Rh, Pt, alloys thereof, or a combination thereof. In another exemplary embodiment, the aqueous phase reforming catalyst comprises Ni alloyed or admixed with Sn, Ge, Bi, B, Cu, Re, Ru, Fe, alloys thereof, or a combination thereof.

In general, the APR reaction should be conducted at a temperature where the thermodynamics are favorable. In one exemplary embodiment, the reforming temperature is in the range of about 100° C. to about 450° C., and the reforming pressure is a pressure where the water and the oxygenated hydrocarbon are gaseous. In another exemplary embodiment, the reforming temperature is in the range of about 100° C. to about 300° C., and the reforming pressure is a pressure where the water and the oxygenated hydrocarbon are gaseous. In yet another exemplary embodiment, the reforming temperature is in the range of about 80° C. to 400° C., and the reforming pressure is a pressure where the water and the oxygenated hydrocarbon are liquid.

In general, the deoxygenation reaction should be conducted at a temperature where the thermodynamics are favorable. In one exemplary embodiment, the deoxygenation temperature is in the range of about 100° C. to 600° C., and the deoxygenation pressure is at least 0.1 atmosphere. In another exemplary embodiment, the deoxygenation temperature is in the range of about 80° C. to about 300° C., and the deoxygenation pressure is a pressure where the water and the oxygenated hydrocarbon are liquid. In yet another exemplary embodiment, the deoxygenation temperature is in the range of about 200° C. to about 280° C., and the deoxygenation pressure is a pressure where the water and the oxygenated hydrocarbon are liquid. In another exemplary embodiment, the deoxygenation temperature is in the range of about 100° C. to 600° C., and the deoxygenation pressure is a pressure where the water and the oxygenated hydrocarbon are gaseous. In another exemplary embodiment, the deoxygenation temperature is in the range of about 200° C. to 280° C., and the deoxygenation pressure is a pressure where the water and the oxygenated hydrocarbon are gaseous. In another exemplary embodiment, the reforming temperature and deoxygenation temperature is in the range of about 100° C. to 450° C., and the reforming pressure and deoxygenation pressure is in the range of about 72 psig to 1300 psig. In another exemplary embodiment, the reforming temperature and deoxygenation temperature is in the range of about 120° C. to 300° C., and the reforming pressure and deoxygenation pressure is in the range of about 72 psig to 1200 psig. In another exemplary embodiment, the reforming temperature and deoxygenation temperature is in the range of about 200° C. to 280° C., and the reforming pressure and deoxygenation pressure is in the range of about 200 psig to 725 psig.

In general, the condensation reaction should be conducted at a temperature where the thermodynamics are favorable. In one exemplary embodiment, the condensation temperature is in the range of about 80° C. to 500° C., and the condensation pressure is in the range of about 0 psig to 1200 psig. In another exemplary embodiment, the condensation temperature is in the range of about 125° C. to 450° C., and the condensation pressure is at least 0.1 atm. In another exemplary embodiment, the condensation temperature is in the range of about 125° C. to 250° C., and the condensation pressure is in the range of about 0 psig to 700 psig. In another exemplary embodiment, the condensation temperature is in the range of about 250° C. to 425° C.

In an exemplary embodiment, the reaction stream further comprises water, and the method further comprises the step or act of dewatering the reaction stream prior to reacting the oxygenate in the presence of the condensation catalyst.

In an exemplary embodiment, the method further comprises the step or act of catalytically reacting in the liquid and/or vapor phase a sugar, sugar alcohol or polyhydric alcohol with $H_2$ in the presence of a hydrogenolysis catalyst at a hydrogenolysis temperature and hydrogenolysis pressure to produce the oxygenated hydrocarbon. In another embodiment, the hydrogenolysis temperature is at least 110° C. and the hydrogenolysis pressure is in the range of about 10 psig to 2400 psig. In another exemplary embodiment, the hydrogenolysis temperature is in the range of about 110° C. to 300° C. The hydrogenolysis catalyst generally comprises phosphate, Cr, Mo, W, Re, Mn, Cu, Cd, Fe, Ru, Os, Ir, Co, Rh, Pt, Pd, Ni, alloys thereof, or a combination thereof. In another exemplary embodiment, the hydrogenolysis catalyst further comprises Au, Ag, Zn, Sn, Bi, B, Cr, Mn, O, alloys thereof, or a combination thereof. In another exemplary embodiment, the hydrogenolysis catalyst further comprises an alkaline earth metal oxide. In another exemplary embodiment, the hydrogenolysis catalyst further comprises any one of the above supports. In another exemplary embodiment, the $H_2$ comprises in situ generated $H_2$, external $H_2$, recycled $H_2$, or a combination thereof.

In another exemplary embodiment, the method further comprises the step or act of catalytically reacting in the liquid and/or vapor phase a sugar, furfural, carboxylic acid, ketone, or furan with $H_2$ in the presence of a hydrogenation catalyst at a hydrogenation temperature and hydrogenation pressure to produce the oxygenated hydrocarbon. In another embodiment, the hydrogenation temperature is in the range of about 80° C. to 250° C., and the hydrogenation pressure is in the range of about 100 psig to 2000 psig. The hydrogenation catalyst generally comprises a support and Fe, Ru, Os, Ir, Co, Rh, Pt, Pd, Ni, Re, Cu, alloys thereof, or a combination thereof. In another exemplary embodiment, the hydrogenation catalyst further comprises Ag, Au, Cr, Zn, Mn, Sn, Bi, Mo, W, B, P, alloys thereof, or a combination thereof. In another exemplary embodiment, the support comprises any one of the above supports. In another exemplary embodiment, the $H_2$ comprises in situ generated $H_2$, external $H_2$, recycled $H_2$, or a combination thereof.

In another exemplary embodiment, the method further comprises the step or act of catalytically reacting the $C_{4+}$ compound in the liquid phase and/or vapor phase in the presence of a finishing catalyst at a finishing temperature and a finishing pressure. The finishing catalyst generally comprises a support and Cu, Ni, Fe, Co, Ru, Pd, Rh, Pt, Ir, Os, an alloy thereof, or a combination thereof. In another exemplary embodiment, the finishing catalyst further comprises a modifier being Au, Ag, Cr, Zn, Mn, Sn, Cu, Cr, Bi, alloys thereof, or a combination thereof. In another exemplary embodiment, the support is any one of the above described supports.

Another aspect of the invention is a method of making a $C_{4+}$ compound comprising the steps or acts of providing water and a water soluble oxygenated hydrocarbon comprising a $C_{1+}O_{1+}$ hydrocarbon in an aqueous liquid phase and/or a vapor phase, catalytically reacting a portion of the water and oxygenated hydrocarbon in the liquid phase and/or vapor phase in the presence of an aqueous phase reforming catalyst at a reforming temperature and a reforming pressure to produce in situ generated $H_2$, catalytically reacting in the liquid and/or vapor phase the oxygenated hydrocarbon with the in situ generated $H_2$ in the presence of a deoxygenation catalyst at a deoxygenation temperature and deoxygenation pressure to produce an oxygenate comprising a $C_{1+}O_{1-3}$ hydrocarbon in a reaction stream, and, catalytically reacting in the liquid and/or vapor phase the oxygenate in the presence of a condensation catalyst comprising a base catalyst at a condensation temperature and condensation pressure to produce the $C_{4+}$ compound, wherein the $C_{4+}$ compound comprises a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and a mixture thereof.

In another exemplary embodiment, the method further comprises the steps or acts of providing supplemental $H_2$, and, catalytically reacting a portion of the oxygenated hydrocarbon with supplemental $H_2$ in the presence of the deoxygenation catalyst to produce the oxygenate.

In another exemplary embodiment, the method further comprises the step or act of catalytically reacting in the liquid and/or vapor phase sugar, furfural, carboxylic acid, ketone, or furan with in situ generated $H_2$ and/or supplemental $H_2$ in the presence of a hydrogenation catalyst at a hydrogenation temperature and hydrogenation pressure to produce the oxygenated hydrocarbon. In another exemplary embodiment, the hydrogenation temperature is in the range of about 80° C. to 250° C., and the hydrogenation pressure is in the range of about 100 psig to 2000 psig. In another exemplary embodiment, the supplemental $H_2$ comprises external $H_2$, recycled $H_2$ or a combination thereof.

In another exemplary embodiment, the method further comprises the step or act of catalytically reacting in the liquid and/or vapor phase a sugar, sugar alcohol or polyhydric alcohol with in situ generated $H_2$ and/or supplemental $H_2$ in the presence of a hydrogenolysis catalyst at a hydrogenolysis temperature and hydrogenolysis pressure to produce the oxygenated hydrocarbon. In another exemplary embodiment, the hydrogenolysis temperature is in the range of about 110° C. to 300° C. In another exemplary embodiment, the supplemental $H_2$ comprises external $H_2$, recycled $H_2$ or a combination thereof.

In another exemplary embodiment, the method includes any of the above described water soluble oxygenated hydrocarbons, oxygenates, $C_{4+}$ compounds, base catalysts, deoxygenation catalysts, aqueous phase reforming catalysts. In another exemplary embodiment, one or more of the deoxygenation catalyst, aqueous phase reforming catalyst, and condensation catalyst are atomically identical. In another exemplary embodiment, the aqueous phase reforming catalyst and deoxygenation catalyst comprise Pt alloyed or admixed with Ni, Ru, Cu, Fe, Rh, Re, alloys thereof, or a combination thereof. In another exemplary embodiment, the aqueous phase reforming catalyst and deoxygenation catalyst comprise Ru alloyed or admixed with Ni, Sn, Cu, Fe, Rh, Pt, alloys thereof, or a combination thereof. In another exemplary embodiment, the aqueous phase reforming catalyst comprises Ni alloyed or admixed with Cu, Re, Ru, Fe, alloys thereof, or a combination thereof. In another exemplary embodiment, the hydrogenation catalyst comprises any one of the above hydrogenation catalysts. In another exemplary embodiment, the hydrogenolysis catalyst comprises any of the above hydrogenolysis catalysts.

In general, the reactions should be conducted at temperatures and pressures where the thermodynamics are favorable. In one exemplary embodiment, the reforming temperature is in the range of about 100° C. to about 450° C., and the reforming pressure is a pressure where the water and the oxygenated hydrocarbon are gaseous. In another exemplary embodiment, the reforming temperature is in the range of about 80° C. to 400° C., and the reforming pressure is a pressure where the water and the oxygenated hydrocarbon are liquid. In another exemplary embodiment, the deoxygenation temperature is in the range of about 100° C. to 600° C., and the deoxygenation pressure is at least 0.1 atmosphere. In another exemplary embodiment, the reforming temperature and deoxygenation temperature is in the range of about 100° C. to 450° C., and the reforming pressure and deoxygenation pressure is in the range of about 72 psig to 1300 psig. In another exemplary embodiment, the condensation temperature is in the range of about 80° C. to 500° C., and the condensation pressure is at least 0.1 atm.

In another exemplary embodiment, the reaction stream further comprises water, and, the method further comprises the step or act of dewatering the reaction stream prior to reacting the oxygenate in the presence of the condensation catalyst.

In another exemplary embodiment, the step of catalytically reacting the oxygenated hydrocarbon with in situ generated $H_2$ in the presence of the deoxygenation catalyst is conducted in the presence of an insignificantly effective amount of external $H_2$. In another exemplary embodiment, the molar ratio of the total oxygen atoms in the oxygenated hydrocarbons to the total hydrogen atoms in the external $H_2$ is less than 1:1.

In another exemplary embodiment, the method further comprises the step or act of catalytically reacting the $C_{4+}$ compound in the liquid phase and/or vapor phase in the presence of a finishing catalyst at a finishing temperature and a finishing pressure, wherein the finishing catalyst comprises a support and Cu, Ni, Fe, Co, Ru, Pd, Rh, Pt, Ir, Os, an alloy thereof, or a combination thereof. In another exemplary embodiment, the finishing catalyst further comprises a modifier being Au, Ag, Cr, Zn, Mn, Sn, Cu, Cr, Bi, alloys thereof, or a combination thereof. In another exemplary embodiment, the support comprises any one of the above supports.

In another exemplary embodiment, the method is performed in a reactor system comprising one or more reactor vessels, wherein the reactor system is adapted to be configured as continuous flow, batch, semi-batch, multi-system or a combination thereof. In another exemplary embodiment, the reactor system further comprises one or more of a fluidized catalytic bed, a swing bed, fixed bed, moving bed or a combination thereof, wherein each bed is adapted to be housed within a reactor vessel. In another exemplary embodiment, the method is performed in the continuous flow reactor system at steady-state equilibrium. In another exemplary embodiment, the reactor system further comprises a reforming bed adapted to contain the aqueous phase reforming catalyst, a deoxygenation bed adapted to contain the deoxygenation catalyst, and, a condensation bed adapted to contain the condensation catalyst. In another exemplary embodiment, the reforming bed and deoxygenation bed are oriented in a stacked, side-by-side or parallel configuration, and the reforming and deoxygenation beds are housed within a single reactor vessel. In another exemplary embodiment, the reforming bed is housed within a reforming reactor vessel, and the deoxygenation bed is housed within a deoxygenation reactor vessel. In another exemplary embodiment, the condensation bed is housed within a condensation reactor vessel. In another exemplary embodiment, the single reactor vessel is further adapted to house the condensation bed. In another exemplary embodiment, the reforming bed, deoxygenation bed, and condensation bed are oriented in a stacked, side-by-side or parallel configuration within the single reactor vessel. In another exemplary embodiment, the continuous flow reactor system is oriented to provide horizontal, vertical or diagonal flow. In another exemplary embodiment, the deoxygenation bed is housed within a deoxygenation reactor vessel providing up-flow, and wherein the condensation bed is housed within a condensation reactor vessel providing down-flow. In another exemplary embodiment, each catalytic reaction occurs at steady-state equilibrium.

Another aspect of the invention is a method of making a $C_{4+}$ compound comprising the steps or acts of providing an aqueous solution comprising water and a member selected from the group consisting of a sugar, furfural, carboxylic acid, ketone, furan, and a combination thereof; catalytically reacting in a liquid and/or vapor phase the sugar, furfural, carboxylic acid, ketone, furan, or combination thereof, with $H_2$ in the presence of a hydrogenation catalyst at a hydrogenation temperature and hydrogenation pressure to produce an oxygenated hydrocarbon comprising a $C_{1+}O_{1-3}$ hydrocarbon, catalytically reacting a portion of the water and oxygenated hydrocarbon in the liquid phase and/or vapor phase in the presence of an aqueous phase reforming catalyst at a reforming temperature and a reforming pressure to produce in situ generated $H_2$, catalytically reacting in the liquid and/or vapor phase the oxygenated hydrocarbon with the in situ generated $H_2$ in the presence of a deoxygenation catalyst at a deoxygenation temperature and deoxygenation pressure to produce an oxygenate comprising a $C_{1+}O_{1-3}$ hydrocarbon, and, catalytically reacting in the liquid and/or vapor phase the oxygenate in the presence of a condensation catalyst comprising a base catalyst at a condensation temperature and condensation pressure to produce the $C_{4+}$ compound, wherein the $C_{4+}$ compound comprises a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and, a mixture thereof.

In another exemplary embodiment, the method further comprises providing supplemental $H_2$ comprising external $H_2$, recycled $H_2$ or a combination thereof, and reacting the supplemental $H_2$ with the sugar, furfural, carboxylic acid, ketone, furan, or combination thereof and/or with the $C_{1+}O_{1+}$ oxygenated hydrocarbon.

In another exemplary embodiment, the oxygenated hydrocarbon comprises any of the above oxygenated hydrocarbons; the oxygenate comprises any of the above oxygenates; the $C_{4+}$ compound comprises any of the above $C_{4+}$ compounds; the hydrogenation catalyst comprises any of the above hydrogenation catalysts; the aqueous phase reforming catalyst comprises any of the above aqueous phase reforming catalysts; the condensation catalyst comprises any of the above base condensation catalysts; and, the deoxygenation catalyst comprises any of the above deoxygenation catalysts.

In another exemplary embodiment, one or more of the hydrogenation catalyst, aqueous phase reforming catalyst, deoxygenation catalyst, and condensation catalyst are atomically identical.

Another aspect of the invention is a method of making a $C_{4+}$ compound comprising providing an aqueous solution comprising water and a polysaccharide, disaccharide, monosaccharide, polyhydric alcohol, sugar, sugar alcohol, or a combination thereof, catalytically reacting in a liquid and/or vapor phase the sugar, sugar alcohol, polysaccharide, disaccharide, monosaccharide, polyhydric alcohol, or combination, with $H_2$ in the presence of a hydrogenolysis catalyst at a hydrogenolysis temperature and hydrogenolysis pressure to produce an oxygenated hydrocarbon comprising a $C_{1+}O_{1+}$ hydrocarbon, catalytically reacting a portion of the water and oxygenated hydrocarbon in the liquid phase and/or vapor phase in the presence of an aqueous phase reforming catalyst at a reforming temperature and a reforming pressure to produce in situ generated $H_2$, catalytically reacting in the liquid and/or vapor phase the oxygenated hydrocarbon with the in situ generated $H_2$ in the presence of a deoxygenation catalyst at a deoxygenation temperature and deoxygenation pressure to produce an oxygenate comprising a $C_{1+}O_{1-3}$ hydrocarbon, and, catalytically reacting in the liquid and/or vapor phase the oxygenate in the presence of a condensation catalyst comprising a base catalyst at a condensation temperature and condensation pressure to produce the $C_{4+}$ compound, wherein the $C_{4+}$ compound comprises a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and a mixture thereof.

In another exemplary embodiment, the method further comprises the steps or acts of providing supplemental $H_2$ comprising external $H_2$, recycled $H_2$ or a combination thereof, and, reacting the supplemental $H_2$ with the polysaccharide, disaccharide, monosaccharide, polyhydric alcohol, sugar, sugar alcohol, or combination thereof and/or with the $C_{1+}O_{1-3}$ oxygenated hydrocarbon.

In another exemplary embodiment, the oxygenated hydrocarbon comprises any of the above oxygenated hydrocarbons; the oxygenate comprises any of the above oxygenates; the $C_{4+}$ compound comprises any of the above $C_{4+}$ compounds; the hydrogenolysis catalyst comprises any of the above hydrogenolysis catalysts; the aqueous phase reforming catalyst comprises any of the above aqueous phase reforming catalysts; the condensation catalyst comprises any of the above base condensation catalysts; and, the deoxygenation catalyst comprises any of the above deoxygenation catalysts.

In another exemplary embodiment, one or more of the hydrogenolysis catalyst, aqueous phase reforming catalyst, deoxygenation catalyst, and condensation catalyst are atomically identical.

Another aspect of the invention is a method of making a $C_{4+}$ compound comprising the steps or acts of providing an oxygenate comprising a $C_{1+}O_{1-3}$ hydrocarbon in an aqueous liquid phase and/or a vapor phase, and, catalytically reacting in the liquid and/or vapor phase the oxygenate in the presence of a condensation catalyst at a condensation temperature and condensation pressure to produce the $C_{4+}$ compound, wherein the $C_{4+}$ compound comprises a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and a mixture thereof.

In another exemplary embodiment, the oxygenate comprises any of the above oxygenates; the $C_{4+}$ compound comprises any of the above $C_{4+}$ compounds; the condensation catalyst comprises any of the above base condensation catalysts; and, the deoxygenation catalyst comprises any of the above deoxygenation catalysts.

Another aspect of the invention is a composition comprising one or more $C_{4+}$ compounds made by any one of the above methods. In an exemplary embodiment of the composition, the composition comprises benzene, toluene, xylene, ethyl benzene, para xylene, meta xylene, ortho xylene, $C_9$ aromatics, an isomer thereof or a mixture thereof.

In an exemplary embodiment of the method of making hydrocarbons, ketones or alcohols, the method further includes the reactions steps each proceeding at steady-state equilibrium. In an exemplary embodiment of the reactor system for making hydrocarbons, the system is adapted to produce hydrocarbons at steady-state equilibrium.

BRIEF DESCRIPTION OF THE DRAWINGS OF THE EXEMPLARY EMBODIMENTS

Figure 5:
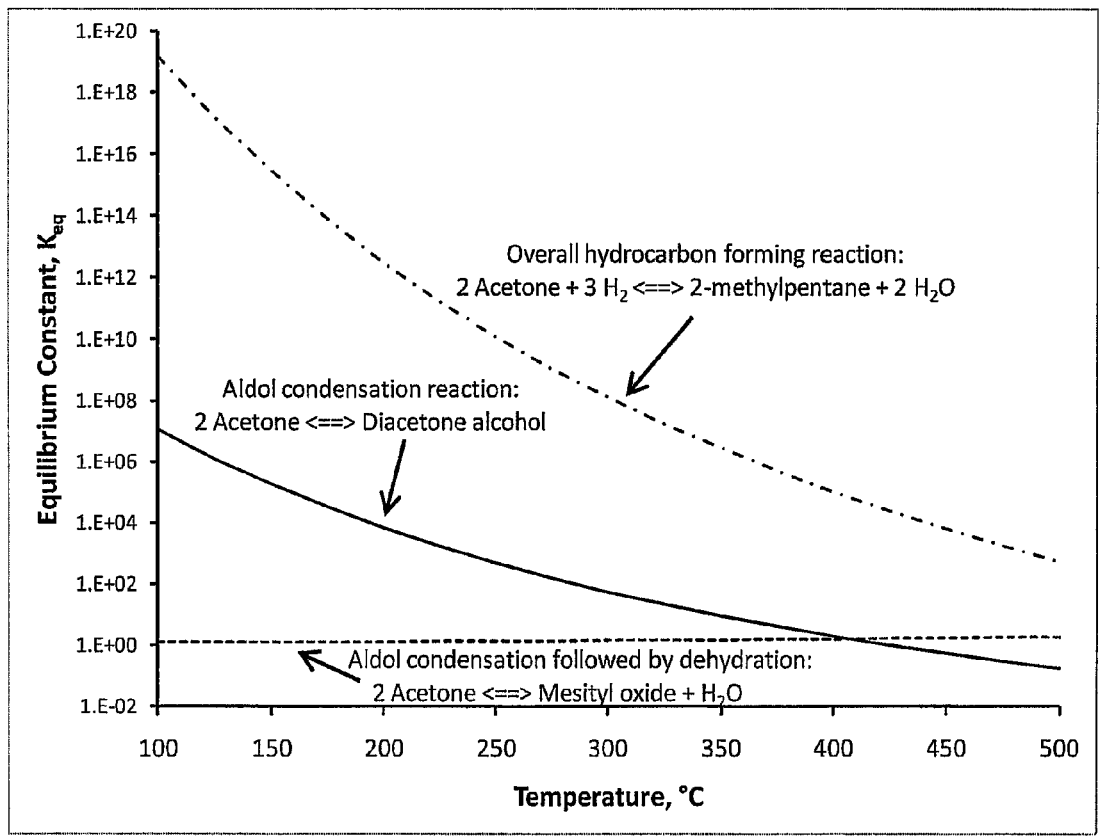

FIG. 5 is a graph illustrating the equilibrium constants associated with the intermediate reaction products and the overall conversion for the reaction of 2 moles of acetone with 3 moles of hydrogen to form 1 mole of 2-methylpentane and 2 moles of water.

Figure 6:
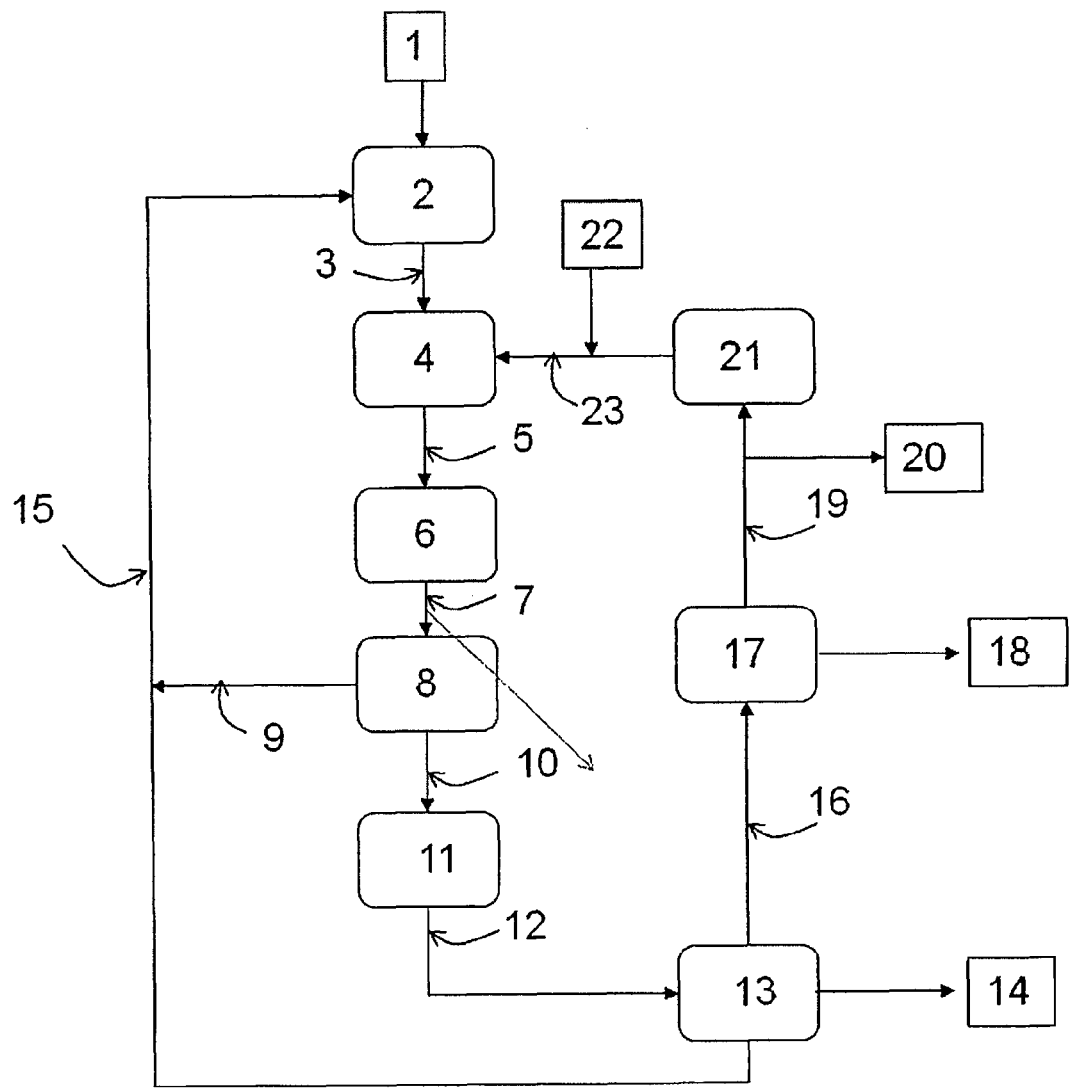

FIG. 6 is a flow diagram illustrating a reactor system configured to allow for the recycle of hydrogen, oxygenates and oxygenated hydrocarbons.

Figure 7:
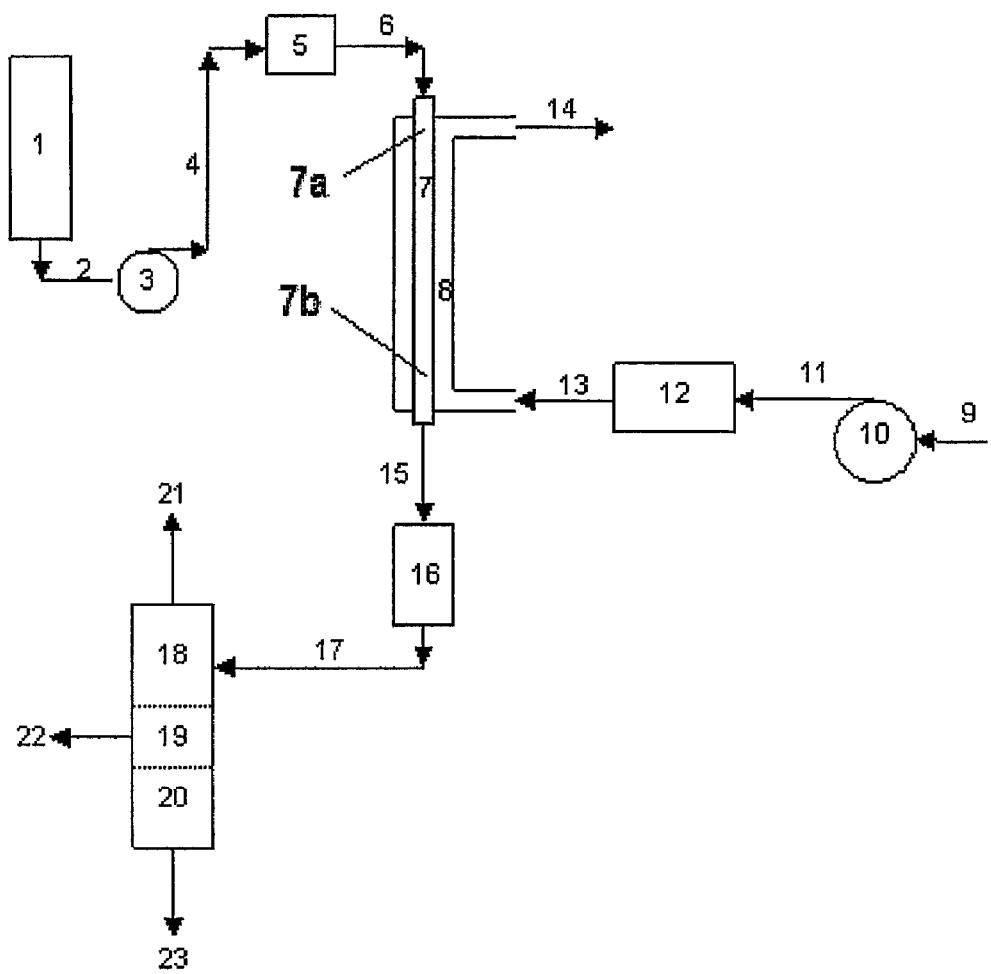

FIG. 7 is a flow diagram illustrating a reactor system configured to allow for the use of air or an oil as a temperature control element.

Figure 8:
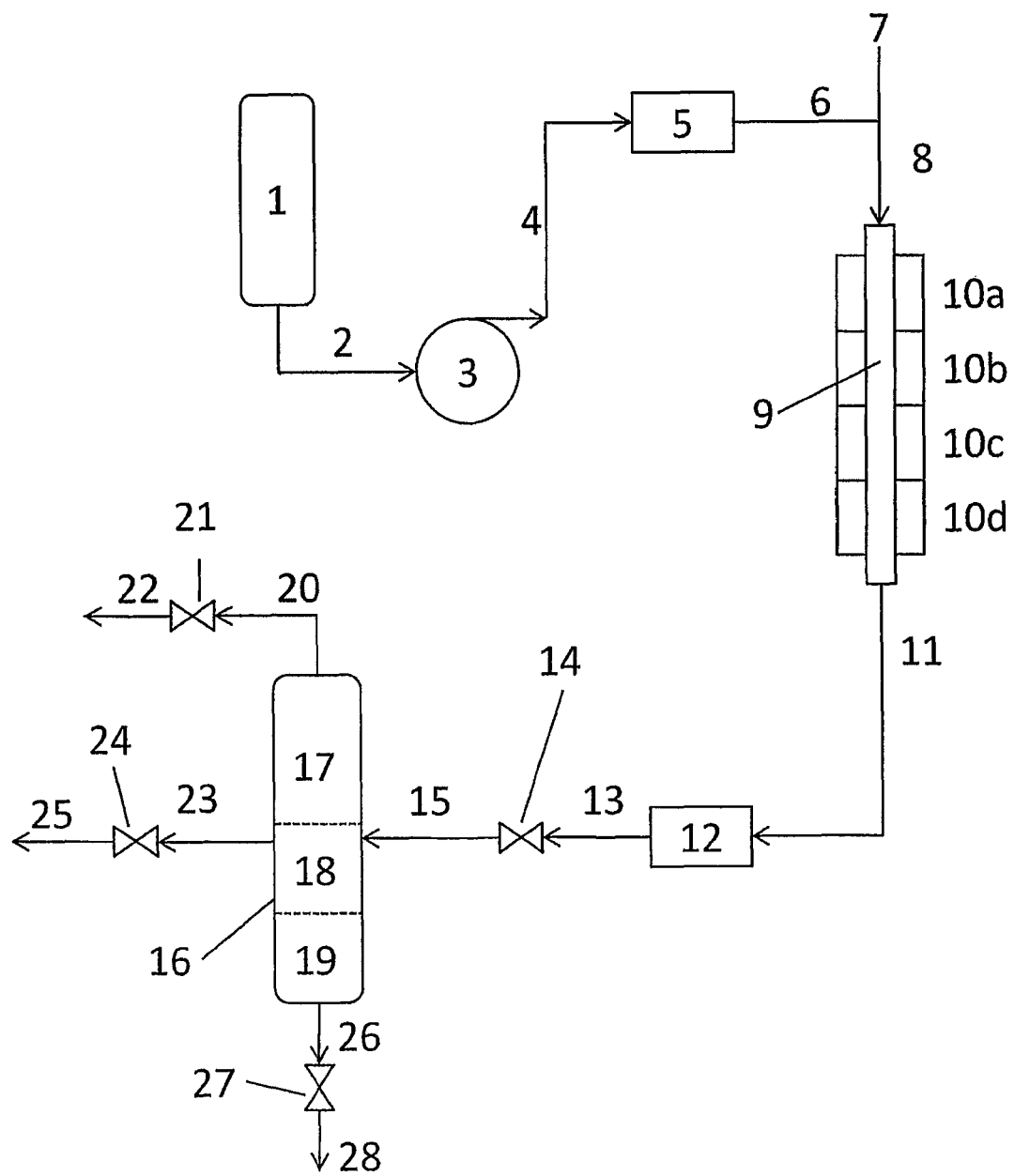

FIG. 8 a flow diagram illustrating a reactor system for the present invention.

Figure 9:
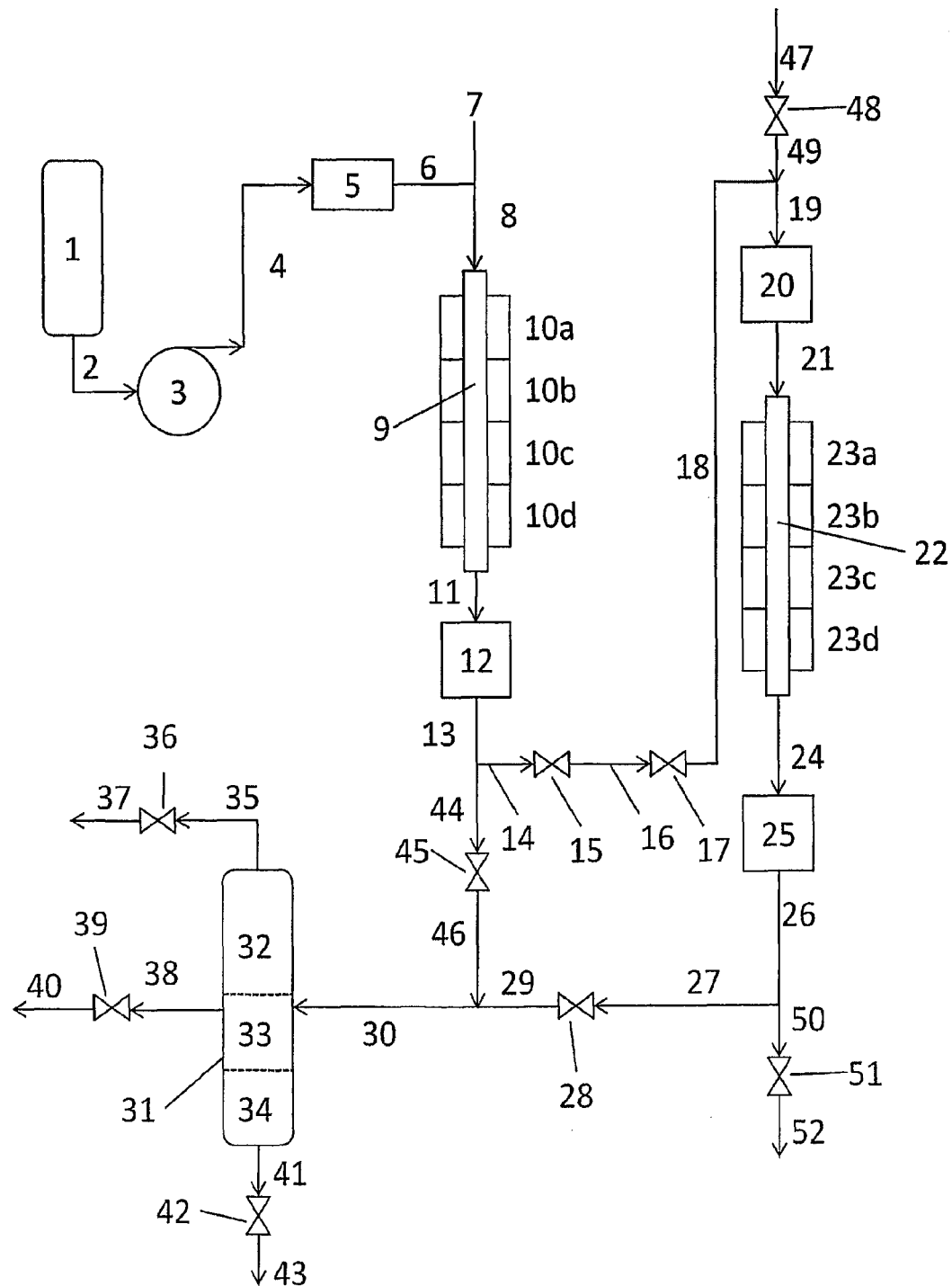

FIG. 9 is a flow diagram illustrating a reactor system utilizing two reactors.

Figure 10:
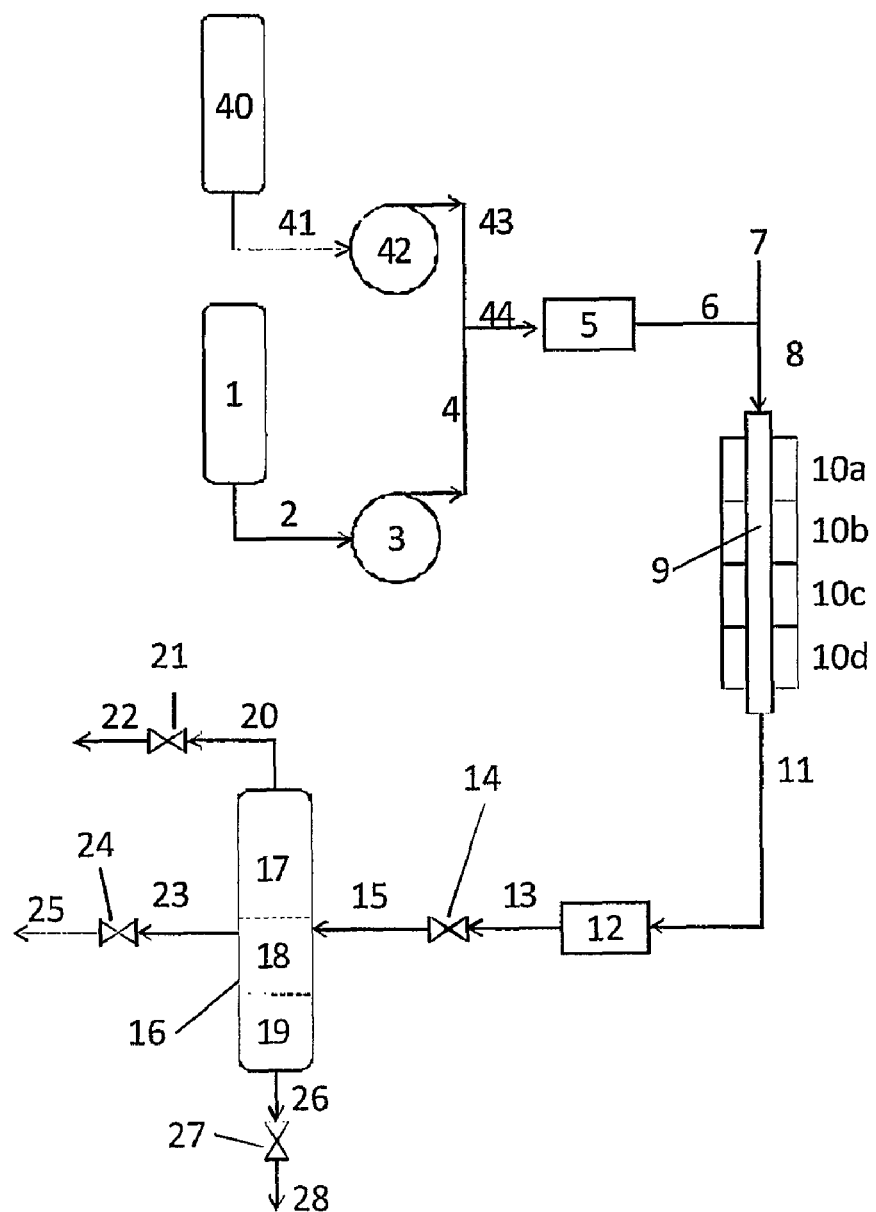

FIG. 10 is a flow diagram illustrating a reactor system utilizing two feedstock lines.

Figure 11:
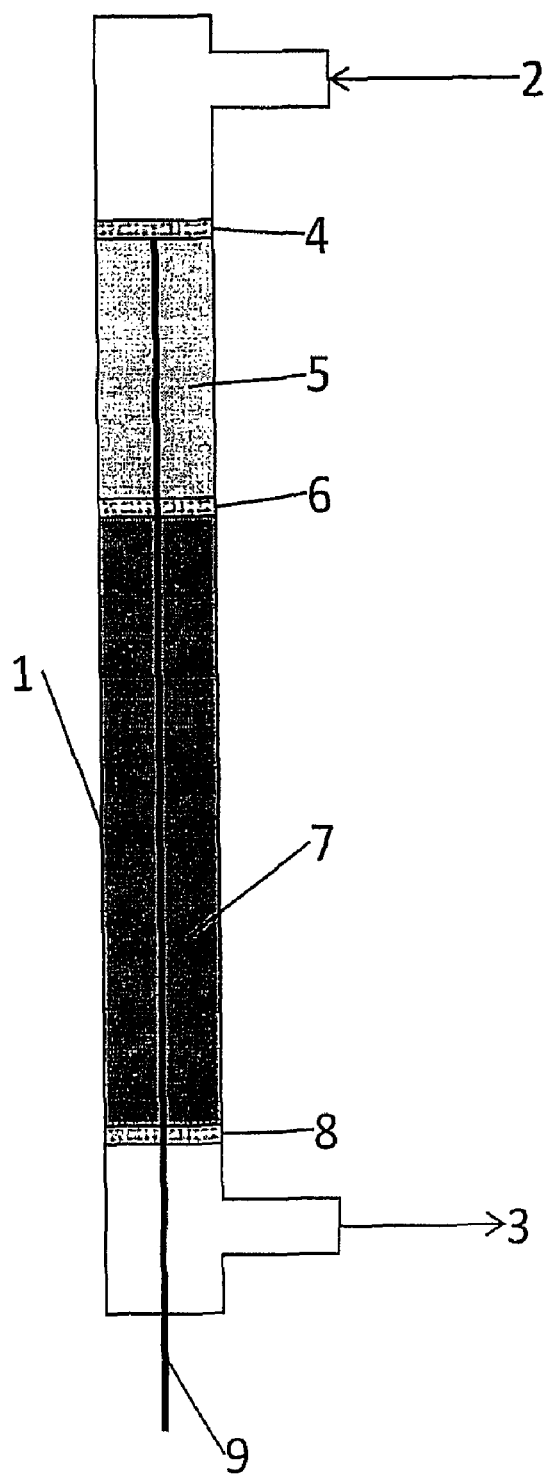

FIG. 11 is an illustration of a reactor useful in practicing the present invention.

Figure 12:
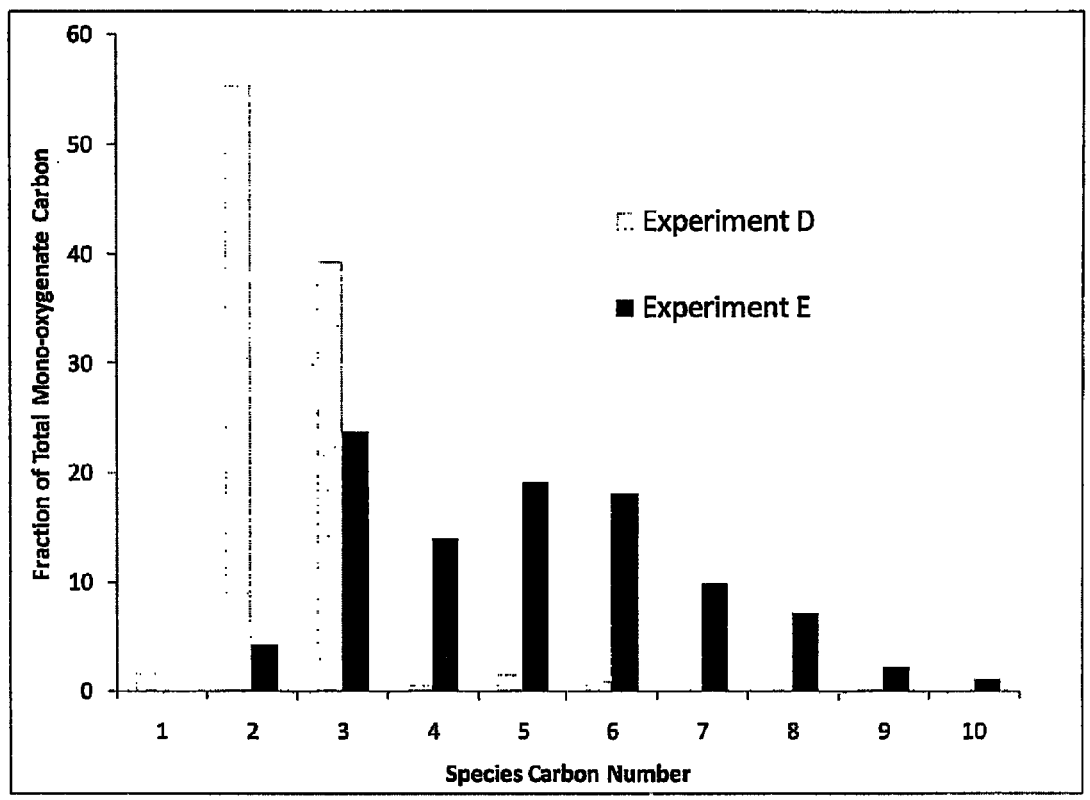

FIG. 12 is a graph illustrating the carbon distribution of mono-oxygenates produced from glycerol.

Figure 13:
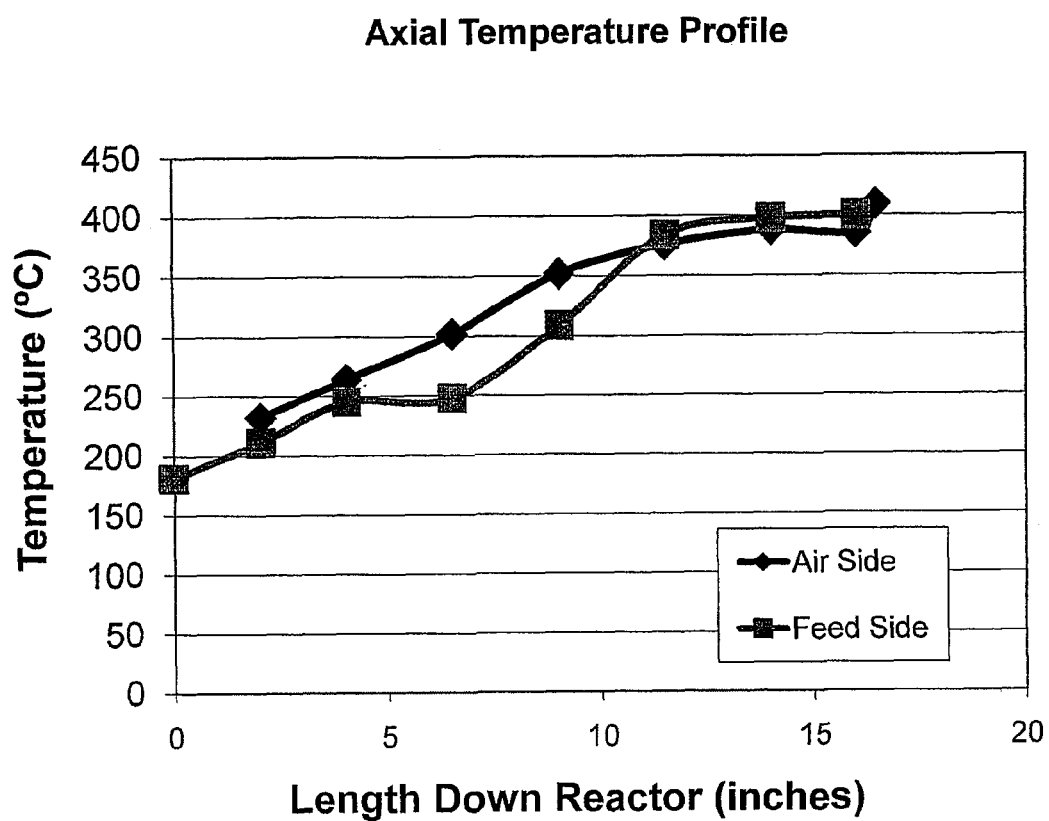

FIG. 13 is a graph illustrating the axial temperature profile for a reactor when used to produce compounds from a feedstock of oxygenated hydrocarbons.

Figure 14:
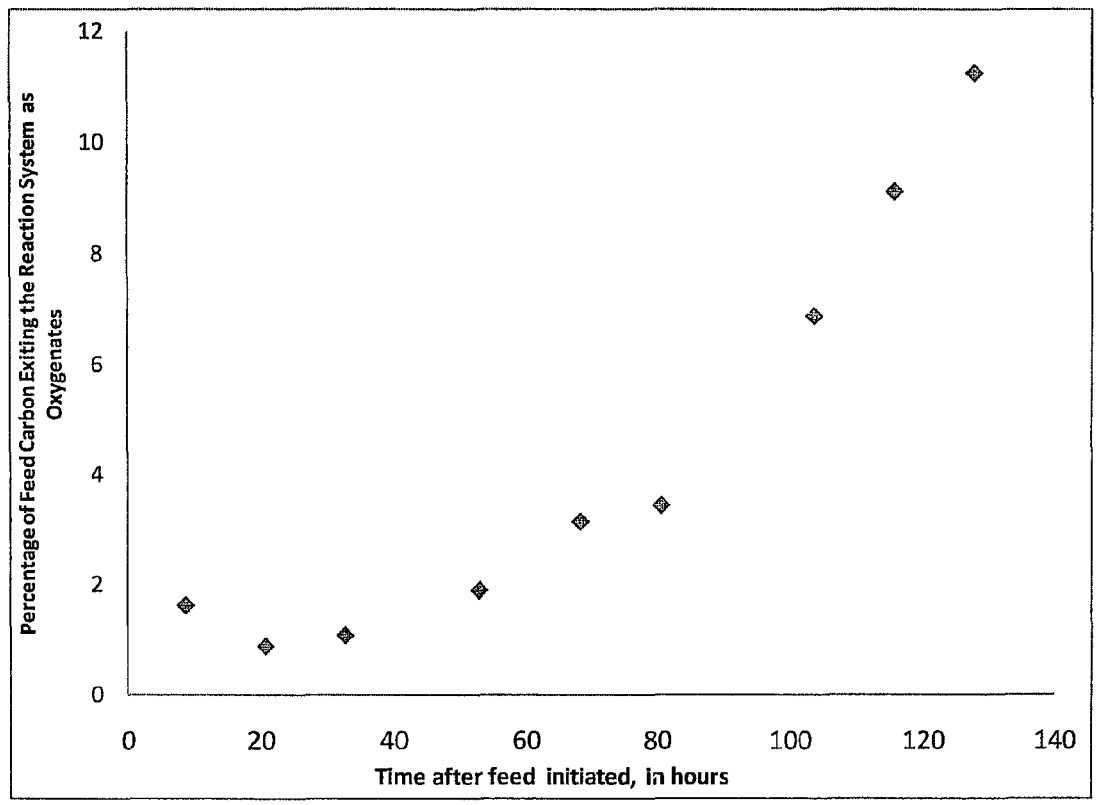

FIG. 14 is a graph illustrating the percentage of feed carbon exiting as oxygenates from the conversion of an oxygenate feed stream to $C_{5+}$ compounds as a function of time.

Figure 15:
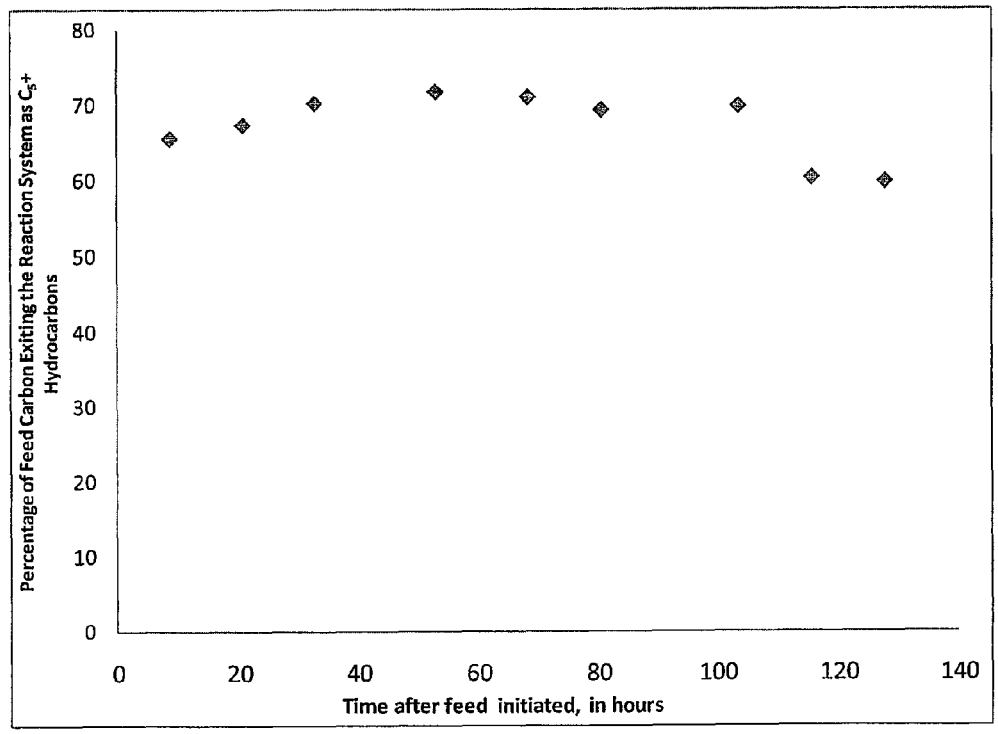

FIG. 15 is a graph illustrating the percentage of feed carbon exiting as $C_{5+}$ hydrocarbons from the conversion of an oxygenate feed stream as a function of time.

Figure 16:
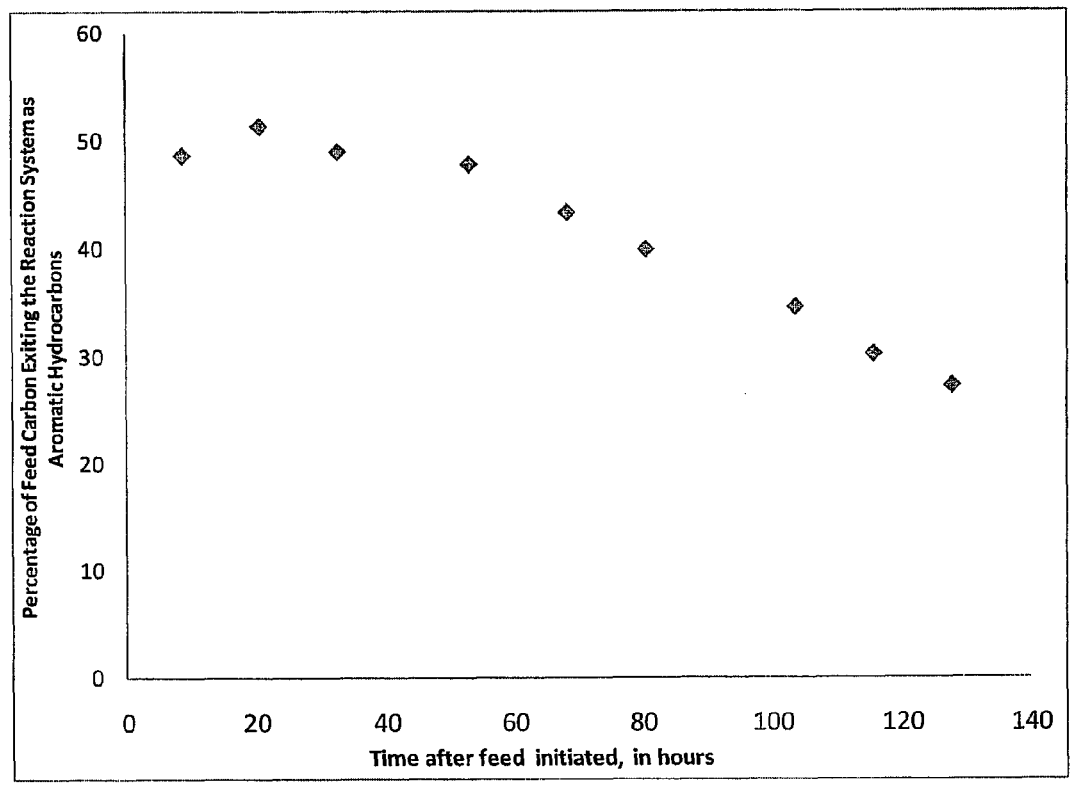

FIG. 16 is a graph illustrating the percentage of feed carbon exiting as $C_{5+}$ aromatic hydrocarbons from the conversion of an oxygenate feed stream as a function of time.

Figure 17:
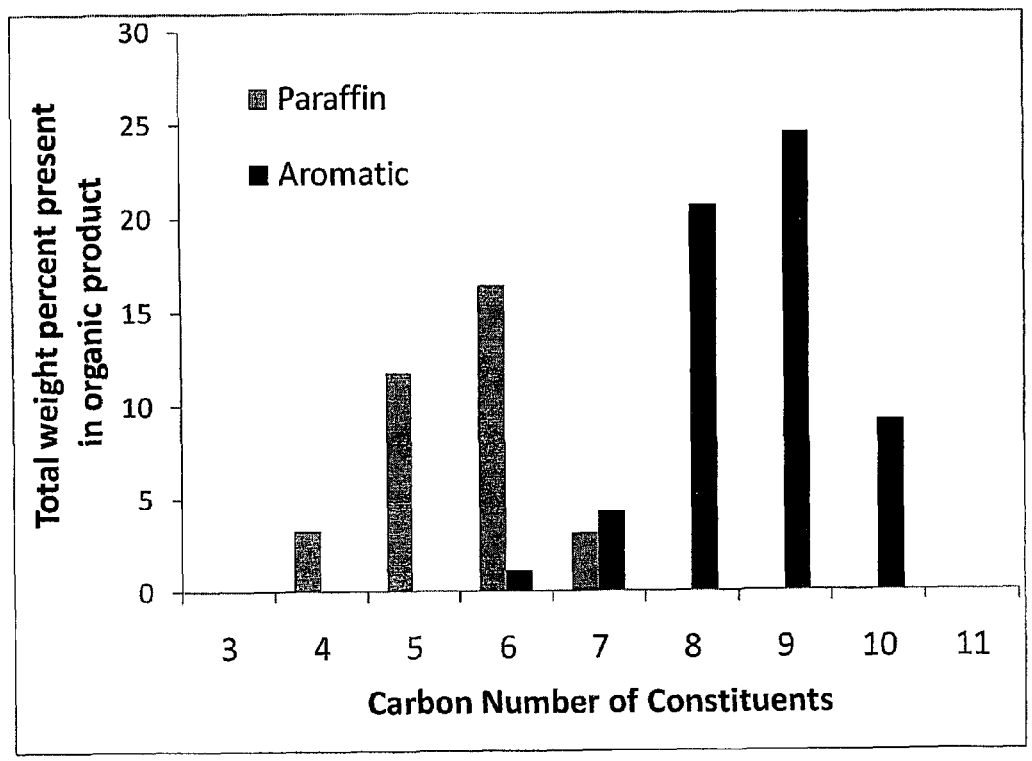

FIG. 17 is a graph showing the total weight percentage of paraffin and aromatic compounds derived from the conversion of a feed stream of sucrose and xylose.

Figure 18:
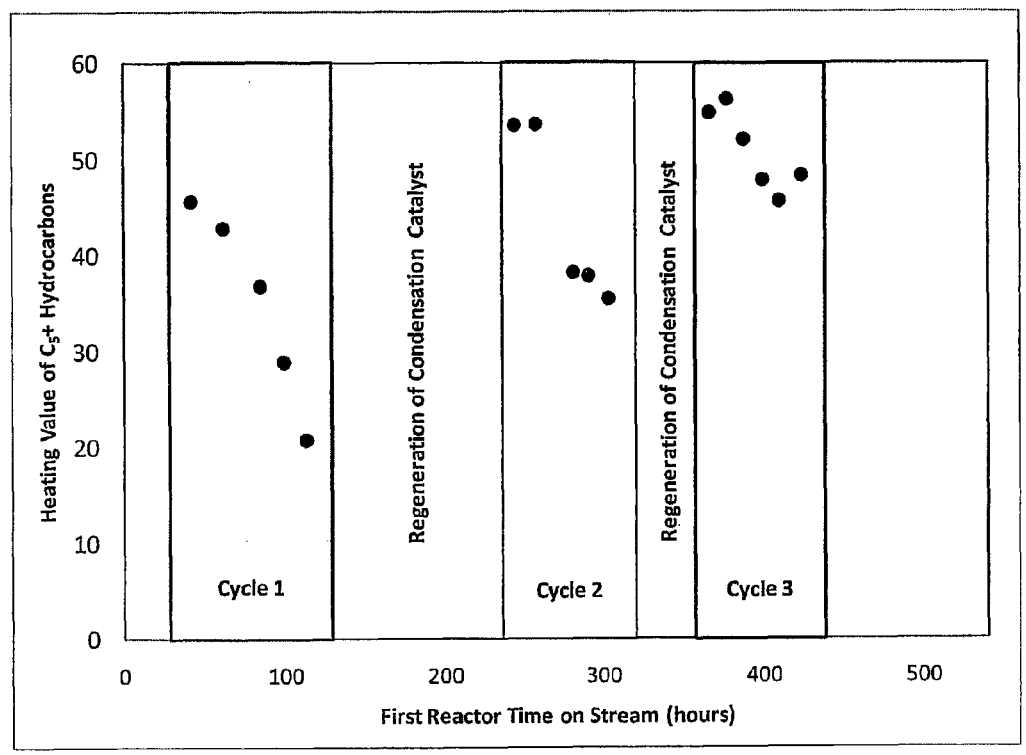

FIG. 18 is a graph illustrating the heating value of $C_{5+}$ hydrocarbons derived from the production of gasoline from sorbitol, as a percentage of the heating value of the feed.

Figure 19:
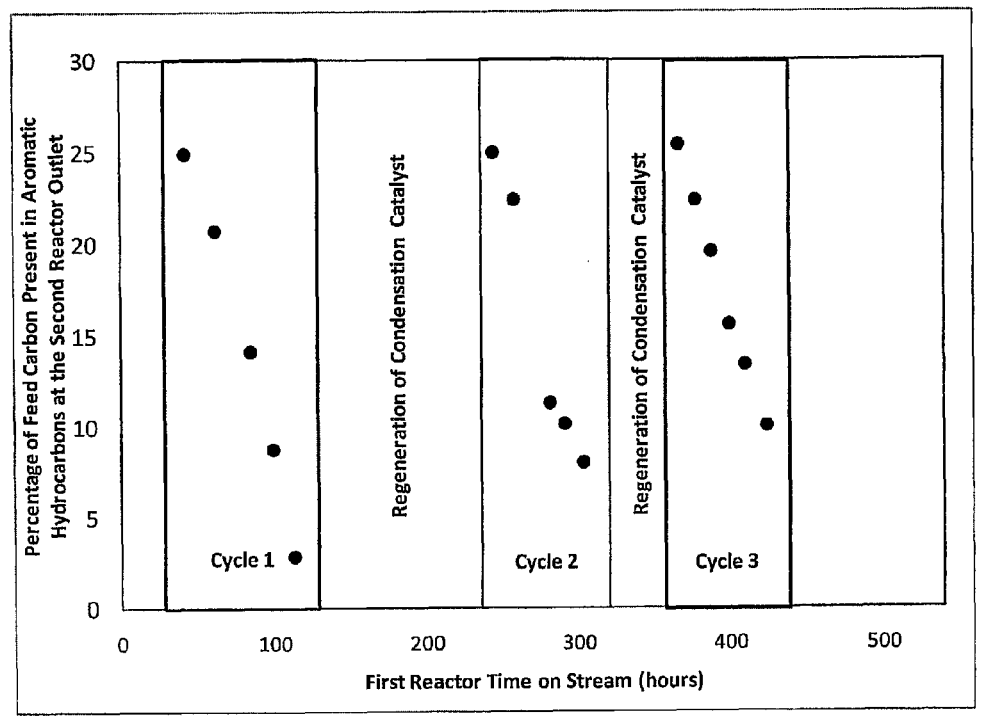

FIG. 19 is a graph illustrating the percentage of carbon recovered as aromatic hydrocarbons from the production of gasoline from sorbitol, shown as a percentage of the carbon present in the feed.

DETAILED DESCRIPTION OF THE EXEMPLARY EMBODIMENTS

There exists a need for new biofuels, and especially biofuels capable of use in the current infrastructure, namely the same distribution system and the same engines without the need for special modifications. There also exists a need for new biofuels that do not depend on microorganisms, enzymes or other expensive and delicate manufacturing processes. There is also a need for processes for converting biomass to hydrocarbon fuels having a greater amount of energy content than ethanol, and with lower energy consumption as part of the manufacturing process. Processes capable of converting biomass using catalytic techniques would be especially advantageous due to its familiarity within the current fuel industry.

The present invention relates to methods, reactor systems and catalysts for producing hydrocarbons, ketones and alcohols from biomass-derived oxygenated hydrocarbons, such as sugars, sugar alcohols, cellulosics, lignocelluloses, hemicelluloses, saccharides and the like. The hydrocarbons and mono-oxygenated hydrocarbons produced are useful in fuel products, such as synthetic gasoline, diesel fuel and/or jet fuels, and as industrial chemicals.

The present invention is directed to methods, reactor systems and catalysts for producing $C_{4+}$ alkanes, $C_{4+}$ alkenes, $C_{5+}$ cycloalkanes, $C_{5+}$ cycloalkenes, aryls, fused aryls, $C_{4+}$ alcohols, $C_{4+}$ ketones, and mixtures thereof (collectively referred to herein as "$C_{4+}$ compounds"), from oxygenated hydrocarbons. The $C_{4+}$ hydrocarbons have from 4 to 30 carbon atoms and may be branched or straight chained alkanes or alkenes, or unsubstituted, mono-substituted or multi-substituted aromatics (aryls) or cycloalkanes. The $C_{4+}$ alcohols and $C_{4+}$ ketones may be cyclic, branched or straight chained, and have from 4 to 30 carbon atoms. Lighter fractions, primarily $C_4$-$C_9$, may be separated for gasoline use. Moderate fractions, such as $C_7$-$C_{14}$, may be separated for jet fuel, while heavier fractions, i.e., $C_{12}$-$C_{24}$, may be separated for diesel use. The heaviest fractions may be used as lubricants or cracked to produce additional gasoline and/or diesel fractions. The $C_{4+}$ compounds may also find use as industrial chemicals, such as xylene, whether as an intermediate or an end product.

Figure 1:
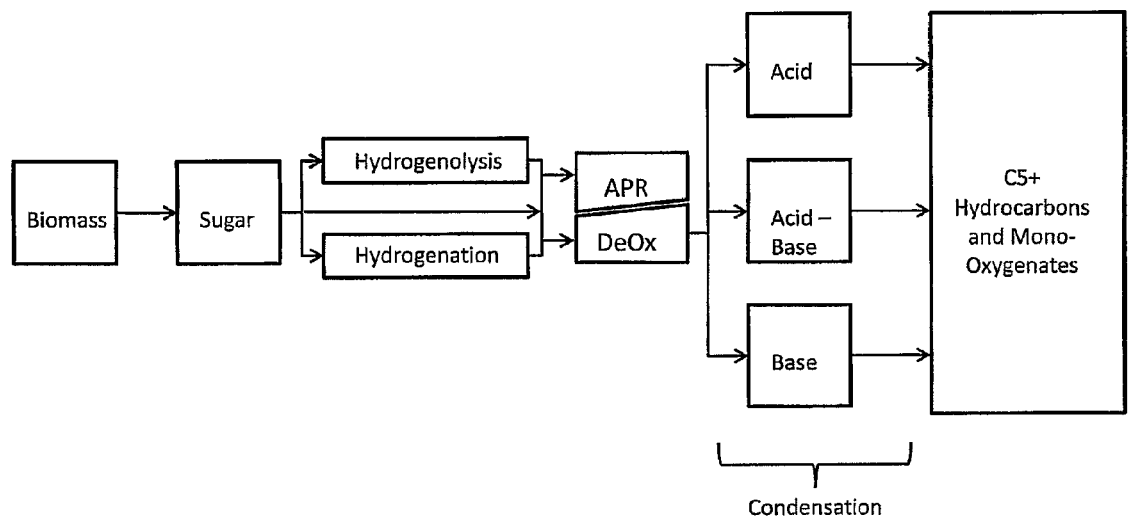
FIG. 1 is a flow diagram illustrating various production pathways associated with the present invention.

The general process is illustrated in FIG. 1. A feedstock solution containing a water-soluble oxygenated hydrocarbon having one or more carbon atoms is reacted with hydrogen over a deoxygenation catalyst to produce oxygenates, and then the oxygenates are reacted over a condensation catalyst under conditions of temperature and pressure effective to cause a condensation reaction that produces the $C_{4+}$ compounds. The hydrogen may originate from any source, but is preferably derived in situ or in parallel from biomass using aqueous phase reforming. The hydrogen and oxygenated hydrocarbons may also be supplemented with recycled hydrogen and oxygenated hydrocarbons derived from the process. The oxygenated hydrocarbon may be a monosaccharide, disaccharide, polysaccharide, cellulose, hemicellulose, lignin, sugar, sugar alcohol or other polyhydric alcohols, or may be derived from the hydrogenation of a sugar, furfural, carboxylic acid, ketone, or furan, or the hydrogenolysis of a sugar, sugar alcohol, polysaccharide, monosaccharide, disaccharide or polyhydric alcohol.

One unique aspect about the present invention is that the $C_{4+}$ compounds are derived from biomass components using catalytic processes instead of microorganisms, enzymes, high temperature gasification or transesterification methods. The present invention can also generate hydrogen in situ to avoid reliance on external hydrogen sources, such as hydrogen generated from the steam reforming of natural gas or by the electrolysis or thermolysis of water. The present invention also generates water, which may be recycled and used in upstream processes or returned to the environment. The present invention is also able to generate non-condensable fuel gases for purposes of providing a heat source within the reactor system or for external processes.

Carbohydrates are the most widely distributed, naturally occurring organic compounds on Earth. Carbohydrates are produced during photosynthesis, a process in which the energy from the sun is converted into chemical energy by combining carbon dioxide with water to form carbohydrates and oxygen:

$$6CO_2 + 6H_2O \xrightarrow{\text{Sunlight}} C_6H_{12}O_6 + 6O_2$$

The energy from sunlight is stored through this process as chemical energy in the form of carbohydrates in plants. The carbohydrates, especially when in a sugar form, are highly reactive compounds that are readily oxidized by living material to generate energy, carbon dioxide and water. Plant materials store these carbohydrates either as sugars, starches, polymeric cellulose, and/or hemi-cellulose.

The presence of oxygen in the molecular structure of carbohydrates contributes to the reactivity of sugars in biological systems. Ethanol fermentation technology takes advantage of this highly reactive nature by forming ethanol at ambient temperatures. The fermentation technology essentially de-functionalizes the highly reactive sugar to generate a partially oxidized hydrocarbon, ethanol. Ethanol, however, has very substantial disadvantages with respect its energy value as highlighted above.

Figure 2:
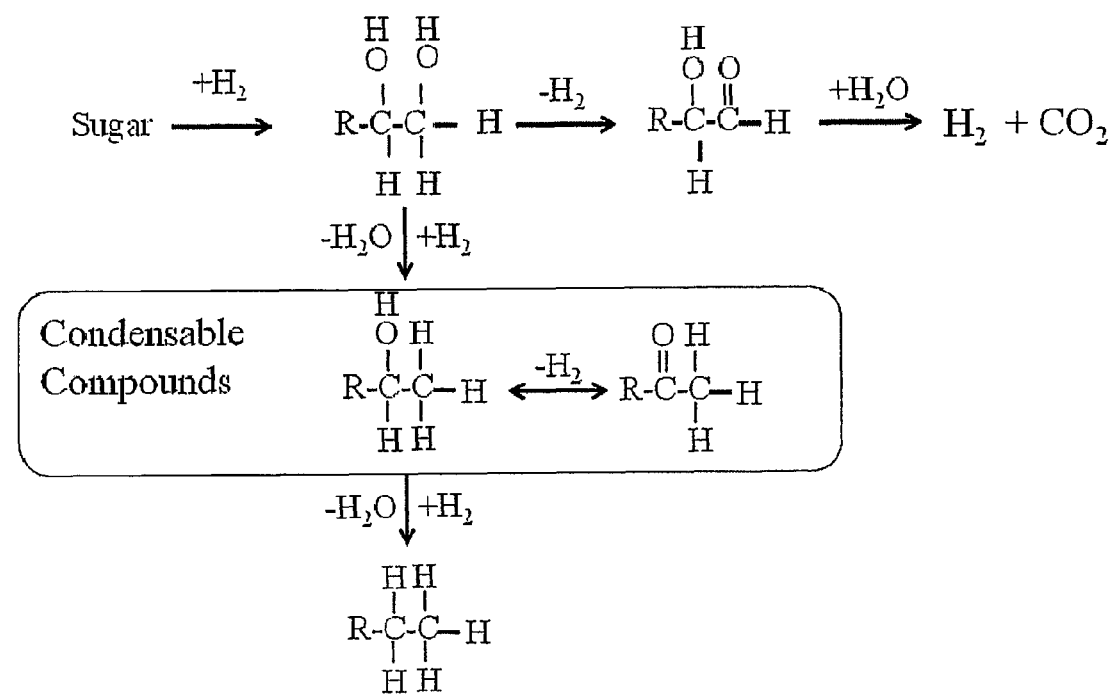
FIG. 2 illustrates potential chemical routes that allow carbohydrates, such as sugars, to be converted to non-oxygenated hydrocarbons.

FIG. 2 shows potential chemical routes that allow carbohydrates, such as sugars, to be converted to non-oxygenated hydrocarbons. Water soluble carbohydrates are known to react with hydrogen over catalyst(s) to generate polyhydric alcohols, either by hydrogenation or hydrogenolysis. The hydrogen has historically been generated externally, i.e., from natural gas or by other processes, but can now be generated in situ or in parallel according to the present invention through the aqueous-phase reforming of the polyhydric alcohol.

The aqueous-phase reforming (APR) of the polyhydric alcohol proceeds through the formation of an aldehyde (shown in FIG. 2) where the aldehyde reacts over a catalyst with water to form hydrogen, carbon dioxide, and a smaller polyhydric alcohol. The polyhdric alcohol can further react with hydrogen over a catalyst through a series of deoxygenation reactions to form either alcohol, ketone, or aldehydes species that can undergo condensation reactions to form either larger carbon number straight chain compounds, branched chain compounds, or cyclic compounds. The condensation reactions can be either acid catalyzed, base catalyzed, or both acid and base catalyzed. The resulting compounds may be hydrocarbons or hydrocarbons containing oxygen, the oxygen of which can be removed through the reaction with hydrogen over a catalyst. The resulting condensed products include $C_{4+}$ alcohols, $C_{4+}$ ketones, $C_{4+}$ alkanes, $C_{4+}$ alkenes, $C_{5+}$ cycloalkanes, $C_{5+}$ cycloalkenes, aryls, fused aryls, and mixtures thereof. The mixtures can be fractionated and blended to produce the appropriate mixtures of molecules typically used in gasoline, jet fuel, or diesel liquid fuels, or in industrial processes.

The de-functionalization begins by reacting the glucose with hydrogen in either a hydrogenation reaction or hydrogenolysis reaction to convert the cyclic sugar molecule to its corresponding linear alcohol, sorbitol, or lower polyhydric alcohols, such as glycerol, propylene glycol, ethylene glycol, xylitol, among others. As indicated above, the hydrogen may be from any source, but is preferably hydrogen generated in situ by aqueous phase reforming or excess hydrogen recycled from the reactor system.

During the aqueous phase reforming process, the carbohydrate first undergoes dehydrogenation to provide adsorbed intermediates, prior to cleavage of C—C or C—O bonds. Subsequent cleavage of C—C bonds leads to the formation of CO and $H_2$, with the CO then reacting with water to form $CO_2$ and $H_2$ by the water-gas shift reaction. Various APR methods and techniques are described in U.S. Pat. Nos. 6,699,457; 6,964,757 and 6,964,758; and U.S. patent application Ser. No. 11/234,727 (all to Cortright et al., and entitled "Low-Temperature Hydrogen Production from Oxygenated Hydrocarbons"); and U.S. Pat. No. 6,953,873 (to Cortright et al., and entitled "Low Temperature Hydrocarbon Production from Oxygenated Hydrocarbons"); and commonly owned co-pending International Patent Application No. PCT/US2006/048030 (to Cortright et al., and entitled "Catalyst and Methods for Reforming Oxygenated Compounds"), all of which are incorporated herein by reference. The term "aqueous phase reforming" and "APR" shall generically denote the reforming of oxygenated hydrocarbons and water to yield hydrogen and carbon dioxide, regardless of whether the reactions takes place in the gaseous phase or in the condensed liquid phase. "APR $H_2$" shall generically refer to the hydrogen produced by the APR process.

Figure 3:
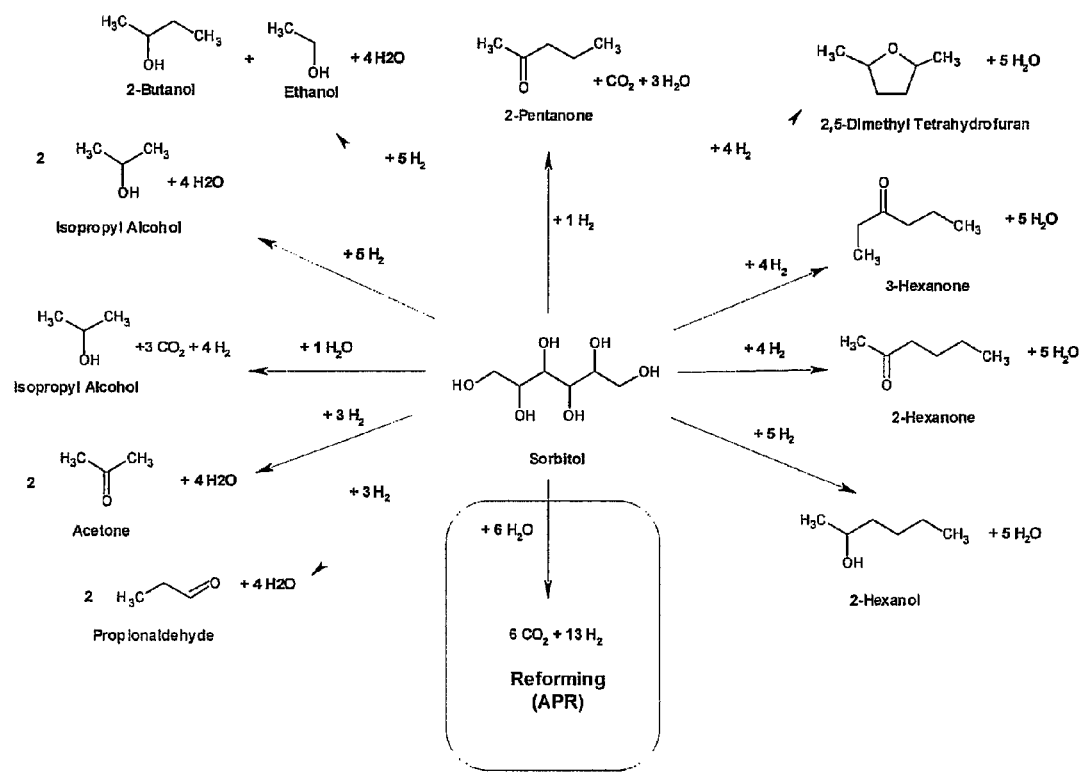
FIG. 3 is an illustration of various reaction pathways involved in the deoxygenation of sorbitol to oxygenates and APR hydrogen.

The resulting oxygenated hydrocarbon, namely the sorbitol or glycerol, propylene glycol, ethylene glycol, xylitol, etc., are further defunctionalized through deoxygenation reactions to form oxygenates, such as alcohols, ketones, aldehydes, furans, diols, triols, hydroxy carboxylic acids, and carboxylic acids for use in later condensation reactions. FIG. 3 illustrates various reaction pathways involved in the deoxygenation of sorbitol to oxygenates and APR hydrogen. In general, without being limited to any particular theory, it is believed that the deoxygenation reactions involves a combination of various different reaction pathways, including without limitation: hydrodeoxygenation, consecutive dehydration-hydrogenation, hydrogenolysis, hydrogenation and dehydration reactions, resulting in the removal of oxygen from the oxygenated hydrocarbon to arrive at a hydrocarbon molecule having the general formula $C_{1+}O_{1-3}$.

The oxygenates produced are then converted into $C_{4+}$ compounds by condensation. Without being limited to any specific theories, it is believed that the acid condensation reactions generally consist of a series of steps involving: (a) the dehydration of oxygenates to olefins; (b) oligomerization of the olefins; (c) cracking reactions; (d) cyclization of larger olefins to form aromatics; (e) paraffin isomerization; and (f) hydrogen-transfer reactions to form paraffins. Basic condensation reactions are believed to generally consist of a series of steps involving: (1) aldol condensation to form a β-hydroxyketone or β-hydroxyaldehyde; (2) dehydration of the β-hydroxyketone or β-hydroxyaldehyde to form a conjugated enone; (3) hydrogenation of the conjugated enone to form a ketone or aldehyde, which may participate in further condensation reactions or conversion to an alcohol or hydrocarbon; and (4) hydrogenation of carbonyls to alcohols, or vice-versa. Acid-base condensation reactions are believed to generally involve any of the previous acidic and/or basic reactions steps.

In certain embodiments, the condensation reactions occur at typical condensation temperatures and pressures. However, in various embodiments, it may also be more favorable to conduct the condensation reactions at temperature and/or pressure conditions that are elevated as compared to typical condensation processes. Generally, conducting condensation reactions under elevated conditions results in unfavorable thermodynamics that limit the extent of conversion to condensation products. The present invention has revealed that conducting the reaction with the condensation catalysts and at the temperatures and pressures described below overcomes these limitations and unexpectedly promotes an immediate conversion of the condensation products to hydrocarbons, ketones and alcohols. The conversion, in turn, removes the condensation products from the reaction, thereby overcoming the thermodynamic limitations of the system to allow additional condensation reactions to occur. Elevated temperature and/or pressure conditions also avoid excessive conversion of the oxygenates directly to their corresponding hydrocarbons. The process also has the added benefit of allowing for the condensation reactions, deoxygenation reactions and APR reactions to occur in a single reactor and under steady-state equilibrium.

Figure 4:
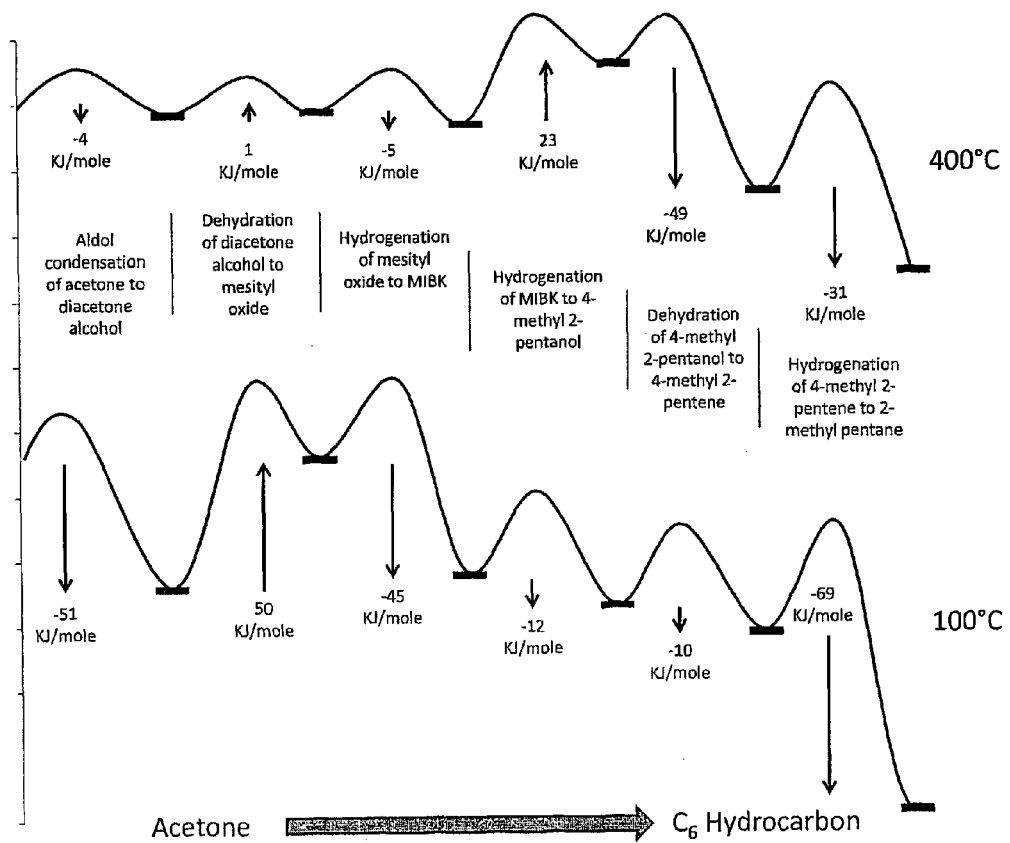
FIG. 4 is an illustration of the thermodynamic equilibriums along the reaction pathway for converting acetone to 2-methyl pentane at 100° C. and 400° C.

For any given reaction, the free energy change is indicative of the favorability of the forward reaction. The more negative the free energy change, the more favorable the reaction. As a result, reactions associated with a highly negative change in free energy are generally favorable and have the potential to exhibit high conversions to reaction products. Conversely, reactions associated with positive changes in free energy are not favorable and are inherently limited in the extent to which reactants are converted to products. As an illustration, FIG. 4 shows the free energy changes associated with steps along the reaction pathway for converting acetone and hydrogen to a $C_6$ hydrocarbon (2-methylpentane) and water at 100° C. and 400° C. The known free energy levels of the stable intermediates derived along this pathway are shown with a solid line. The first step in the reaction pathway is the aldol condensation of two molecules of acetone to form one molecule of diacetone alcohol. The reaction at the lower temperature (100° C.) has a free energy change of −53 KJ/mole and is thermodynamically favored, while the reaction at the higher temperature (400° C.) is less favorable due to a free energy change of −10 KJ/mole. The implication is that the maximum conversion of pure acetone to diacetone alcohol for this step decreases as the temperature is increased (greater than 99% theoretical maximal conversion at 100° C. at atmospheric pressure, to only 15% at 400° C. at atmospheric pressure). Accordingly, the thermodynamic equilibrium limitation imposes an absolute limit to the amount of diacetone alcohol that may be produced under given conditions and in the absence of other reactions. This is further illustrated in FIG. 5, which provides the equilibrium constants associated with the intermediate reaction products and the overall conversion for the reaction of 2 moles of acetone with 3 moles of hydrogen to form 1 mole of 2-methylpentane and 2 moles of water. It can be seen that the equilibrium constant for the conversion of acetone to diacetone alcohol decreases with increasing temperature.

The present invention obviates this issue by immediately converting the condensation product to a compound that provides a more favorable reaction environment. In the case above, by removing the diacetone alcohol from the reaction mixture through a dehydration reaction that forms mesityl oxide, additional diacetone alcohol can be formed. In particular, the combination of a condensation and dehydration step to provide mesityl oxide and water from acetone provides a slightly more favorable reaction environment. As illustrated in FIG. 5, the conversion of acetone to mesityl oxide and water is slightly more favorable at the higher temperatures.

The total reaction system pressure also has a beneficial effect on the maximal theoretical extent to which reactant may form a product. Considering the condensation reaction example above, the conversion of acetone to diacetone alcohol is limited to 15% at 400° C. at atmospheric pressure with pure acetone feed. By increasing the system pressure to 600 psi gauge pressure, the equilibrium conversion shifts so that up to 76% conversion may be achieved at the same temperature. For reactions exhibiting a net decrease in the number of moles of product as compared to the moles of reactant, an increase in system pressure (with all other conditions held constant) will act to increase the equilibrium product conversion. For the overall conversion of ketones to hydrocarbons, there is typically a net decrease in the moles of product compared to the moles of reactant, thus higher reaction pressures would lead to higher potential equilibrium conversions.

The present invention strikes a balance with the above thermodynamic limitations by operating with condensation catalysts and at temperature and pressure conditions that offset any reduction in the production of condensation products with an increase in the conversion to other downstream products. The kinetics of the entire system is also more favorable such that products may be produced continuously and at a more desirable rate. In terms of scaled-up production, after start-up, the reactor systems may be process controlled, and the reactions could proceed at steady-state equilibrium.

Oxygenates

The $C_{4+}$ compounds are derived from oxygenates. As used herein, "oxygenates" generically refers to hydrocarbon compounds having 1 or more carbon atoms and between 1 and 3 oxygen atoms (referred to herein as $C_{1+}O_{1-3}$ hydrocarbons), such as alcohols, ketones, aldehydes, furans, hydroxy carboxylic acids, carboxylic acids, diols and triols. Preferably, the oxygenates have from 1 to 6 carbon atoms, or 2 to 6 carbon atoms, or 3 to 6 carbon atoms. Alcohols may include, without limitation, primary, secondary, linear, branched or cyclic $C_{1+}$ alcohols, such as methanol, ethanol, n-propyl alcohol, isopropyl alcohol, butyl alcohol, isobutyl alcohol, butanol, pentanol, cyclopentanol, hexanol, cyclohexanol, 2-methyl-cyclopentanonol, heptanol, octanol, nonanol, decanol, undecanol, dodecanol, and isomers thereof. The ketones may include, without limitation, hydroxyketones, cyclic ketones, diketones, acetone, propanone, 2-oxopropanal, butanone, butane-2,3-dione, 3-hydroxybutan-2-one, pentanone, cyclopentanone, pentane-2,3-dione, pentane-2,4-dione, hexanone, cyclohexanone, 2-methyl-cyclopentanone, heptanone, octanone, nonanone, decanone, undecanone, dodecanone, methylglyoxal, butanedione, pentanedione, diketohexane, and isomers thereof. The aldehydes may include, without limitation, hydroxyaldehydes, acetaldehyde, propionaldehyde, butyraldehyde, pentanal, hexanal, heptanal, octanal, nonal, decanal, undecanal, dodecanal, and isomers thereof. The carboxylic acids may include, without limitation, formic acid, acetic acid, propionic acid, butanoic acid, pentanoic acid, hexanoic acid, heptanoic acid, isomers and derivatives thereof, including hydroxylated derivatives, such as 2-hydroxybutanoic acid and lactic acid. The diols may include, without limitation, ethylene glycol, propylene glycol, 1,3-propanediol, butanediol, pentanediol, hexanediol, heptanediol, octanediol, nonanediol, decanediol, undecanediol, dodecanediol, and isomers thereof. The triols may include, without limitation, glycerol, 1,1,1 tris(hydroxymethyl)-ethane (trimethylolethane), trimethylolpropane, hexanetriol, and isomers thereof. Furans and furfurals include, without limitation, furan, tetrahydrofuran, dihydrofuran, 2-furan methanol, 2-methyl-tetrahydrofuran, 2,5-dimethyl-tetrahydrofuran, 2-methyl furan, 2-ethyl-tetrahydrofuran, 2-ethyl furan, hydroxylmethylfurfural, 3-hydroxytetrahydrofuran, tetrahydro-3-furanol, 2,5-dimethyl furan, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl) ethanol, hydroxymethyltetrahydrofurfural, and isomers thereof.

The oxygenates may originate from any source, but are preferably derived from biomass. As used herein, the term "biomass" refers to, without limitation, organic materials produced by plants (such as leaves, roots, seeds and stalks), and microbial and animal metabolic wastes. Common sources of biomass include: (1) agricultural wastes, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; and (4) energy crops, such as poplars, willows, switch grass, alfalfa, prairie bluestream, corn, soybean, and the like. The term also refers to the primary building blocks of the above, namely, saccharides, lignin, cellulosics, hemicellulose and starches, among others.

Oxygenates from biomass may be produced by any known method. Such methods include fermentation technologies using enzymes or microorganisms, Fischer-Tropsch reactions to produce $C_{2-10}$ alpha alcohols, and pyrolysis technologies to produce alcohols from oil, among others. In one embodiment, the oxygenates are produced using catalytic reforming technologies, such as the BioForming™ technology developed by Virent Energy Systems, Inc. (Madison, Wis.).

Oxygenated Hydrocarbons

In one embodiment, the oxygenates are derived from the catalytic reforming of oxygenated hydrocarbons. The oxygenated hydrocarbons may be any water-soluble oxygenated hydrocarbon having one or more carbon atoms and at least one oxygen atom (referred to herein as $C_{1+}O_{1+}$ hydrocarbons). Preferably, the oxygenated hydrocarbon has 2 to 12 carbon atoms ($C_{1-12}O_{1-11}$ hydrocarbon), and more preferably 2 to 6 carbon atoms ($C_{1-6}O_{1-6}$ hydrocarbon). The oxygenated hydrocarbon may also have an oxygen-to-carbon ratio ranging from 0.5:1 to 1.5:1, including ratios of 0.75:1.0, 1.0:1.0, 1.25:1.0, 1.5:1.0, and other ratios between. In one example, the oxygenated hydrocarbon has an oxygen-to-carbon ratio of 1:1. Nonlimiting examples of preferred water-soluble oxygenated hydrocarbons include monosaccharides, disaccharides, polysaccharides, sugar, sugar alcohols, alditols, ethanediol, ethanedione, acetic acid, propanol, propanediol, propionic acid, glycerol, glyceraldehyde, dihydroxyacetone, lactic acid, pyruvic acid, malonic acid, butanediols, butanoic acid, aldotetroses, tautaric acid, aldopentoses, aldohexoses, ketotetroses, ketopentoses, ketohexoses, alditols, hemicelluloses, cellulosic derivatives, lignocellulosic derivatives, starches, polyols and the like. Preferably, the oxygenated hydrocarbon includes sugar, sugar alcohols, saccharides and other polyhydric alcohols. More preferably, the oxygenated hydrocarbon is a sugar, such as glucose, fructose, sucrose, maltose, lactose, mannose or xylose, or a sugar alcohol, such as arabitol, erythritol, glycerol, isomalt, lactitol, malitol, mannitol, sorbitol, xylitol, ribitol, or glycol.

Oxygenated hydrocarbons shall also refer to and include alcohols derived by hydrogenation or hydrogenolysis of any of the foregoing. In certain embodiments, it may be preferable to convert the starting oxygenated hydrocarbon to another oxygenated hydrocarbon form that can be more readily converted to the desired oxygenates (e.g., primary, secondary, tertiary or polyhydric alcohols). For instance, some sugars may not convert as efficiently to oxygenates as compared to their corresponding sugar alcohol derivatives. It may therefore be desirable to convert the starting material, such as a sugar, furfural, carboxylic acid, ketone, or furan, into its corresponding alcohol derivative, such as by hydrogenation, or to smaller alcohol molecules, such as by hydrogenolysis.

Various processes are known for hydrogenating sugars, furfurals, carboxylic acids, ketones, and furans to their corresponding alcohol form, including those disclosed by: B. S. Kwak et al. (WO2006/093364A1 and WO 2005/021475A1), involving the preparation of sugar alditols from monosaccharides by hydrogenation over a ruthenium catalyst; and Elliot et al. (U.S. Pat. Nos. 6,253,797 and 6,570,043), disclosing the use of a nickel and rhenium free ruthenium catalyst on a more than 75% rutile titania support to convert sugars to sugar alcohols, all incorporated herein by reference. Other suitable ruthenium catalysts are described by Arndt et al. in published U.S. patent application 2006/0009661 (filed Dec. 3, 2003), and Arena in U.S. Pat. Nos. 4,380,679 (filed Apr. 12, 1982), 4,380,680 (filed May 21, 1982), 4,503,274 (filed Aug. 8, 1983), 4,382,150 (filed Jan. 19, 1982), and 4,487,980 (filed Apr. 29, 1983), all incorporated herein by reference. The hydrogenation catalyst generally includes Cu, Re, Ni, Fe, Co, Ru, Pd, Rh, Pt, Os, Ir, and alloys or combinations thereof, either alone or with promoters such as W, Mo, Au, Ag, Cr, Zn, Mn, Sn, B, P, Bi, and alloys or combinations thereof. The hydrogenation catalyst may also include any one of the supports further described below, and depending on the desired functionality of the catalyst. Other effective hydrogenation catalyst materials include either supported nickel or ruthenium modified with rhenium. In general, the hydrogenation reaction is carried out at hydrogenation temperatures of between about 80° C. to 250° C., and hydrogenation pressures in the range of about 100 psig to 2000 psig. The hydrogen used in the reaction may include in situ generated $H_2$, external $H_2$, recycled $H_2$, or a combination thereof.

The hydrogenation catalyst may also include a supported Group VIII metal catalyst and a metal sponge material, such as a sponge nickel catalyst. Activated sponge nickel catalysts (e.g., Raney nickel) are a well-known class of materials effective for various hydrogenation reactions. One type of sponge nickel catalyst is the type A7063 catalyst available from Activated Metals and Chemicals, Inc., Sevierville, Tenn. The type A7063 catalyst is a molybdenum promoted catalyst, typically containing approximately 1.5% molybdenum and 85% nickel. The use of the sponge nickel catalyst with a feedstock comprising xylose and dextrose is described by M. L. Cunningham et al. in U.S. Pat. No. 6,498,248, filed Sep. 9, 1999, incorporated herein by reference. The use of a Raney nickel catalyst with hydrolyzed corn starch is also described in U.S. Pat. No. 4,694,113, filed Jun. 4, 1986, and incorporated herein by reference.

The preparation of suitable Raney nickel hydrogenation catalysts is described by A. Yoshino et al. in published U.S. patent application 2004/0143024, filed Nov. 7, 2003, incorporated herein by reference. The Raney nickel catalyst may be prepared by treating an alloy of approximately equal amounts by weight of nickel and aluminum with an aqueous alkali solution, e.g., containing about 25 wt. % of sodium hydroxide. The aluminum is selectively dissolved by the aqueous alkali solution leaving particles having a sponge construction and composed predominantly of nickel with a minor amount of aluminum. Promoter metals, such as molybdenum or chromium, may be also included in the initial alloy in an amount such that about 1-2 wt. % remains in the sponge nickel catalyst.

In another embodiment, the hydrogenation catalyst is prepared by impregnating a suitable support material with a solution of ruthenium (III) nitrosylnitrate, ruthenium (III) nitrosylnitrate, or ruthenium (III) chloride in water to form a solid that is then dried for 13 hours at 120° C. in a rotary ball oven (residual water content is less than 1% by weight). The solid is then reduced at atmospheric pressure in a hydrogen stream at 300° C. (uncalcined) or 400° C. (calcined) in the rotary ball furnace for 4 hours. After cooling and rendering inert with nitrogen, the catalyst may then be passivated by passing over 5% by volume of oxygen in nitrogen for a period of 120 minutes.

In yet another embodiment, the hydrogenation reaction is performed using a catalyst comprising a nickel-rhenium catalyst or a tungsten-modified nickel catalyst. One example of a suitable hydrogenation catalyst is the carbon-supported nickel-rhenium catalyst composition disclosed by Werpy et al. in U.S. Pat. No. 7,038,094, filed Sep. 30, 2003, and incorporated herein by reference.

In other embodiments, it may also be desirable to convert the starting oxygenated hydrocarbon, such as a sugar, sugar alcohol or other polyhydric alcohol, to a smaller molecule that can be more readily converted to the desired oxygenates, such as by hydrogenolysis. Such smaller molecules may include primary, secondary, tertiary or polyhydric alcohols having less carbon atoms than the originating oxygenated hydrocarbon. Various processes are known for such hydrogenolysis reactions, including those disclosed by: Werpy et al. in U.S. Pat. Nos. 6,479,713 (filed Oct. 23, 2001), 6,677,385 (filed Aug. 6, 2002), 6,6841,085 (filed Oct. 23, 2001) and 7,083,094 (filed Sep. 30, 2003), all incorporated herein by reference and describing the hydrogenolysis of 5 and 6 carbon sugars and sugar alcohols to propylene glycol, ethylene glycol and glycerol using a rhenium-containing multi-metallic catalyst. Other systems include those described by Arena in U.S. Pat. No. 4,401,823 (filed May 18, 1981) directed to the use of a carbonaceous pyropolymer catalyst containing transition metals (such as chromium, molybdenum, tungsten, rhenium, manganese, copper, cadmium) or Group VIII metals (such as iron, cobalt, nickel, platinum, palladium, rhodium, ruthenium, iridium and osmium) to produce alcohols, acids, ketones, and ethers from polyhydroxylated compounds, such as sugars and sugar alcohols, and U.S. Pat. No. 4,496,780 (filed Jun. 22, 1983) directed to the use of a catalyst system having a Group VIII noble metal on a solid support with an alkaline earth metal oxide to produce glycerol, ethylene glycol and 1,2-propanediol from carbohydrates, each incorporated herein by reference. Another system includes that described by Dubeck et al. in U.S. Pat. No. 4,476,331 (filed Sep. 6, 1983) directed to the use of a sulfide-modified ruthenium catalyst to produce ethylene glycol and propylene glycol from larger polyhydric alcohols, such as sorbitol, also incorporated herein by reference. Other systems include those described by Saxena et al., "Effect of Catalyst Constituents on (Ni, Mo and Cu)/Kieselguhr-Catalyzed Sucrose Hydrogenolysis," Ind. Eng. Chem. Res. 44, 1466-1473 (2005), describing the use of Ni, W, and Cu on a kieselguhr support, incorporated herein by reference.

In one embodiment, the hydrogenolysis catalyst includes Cr, Mo, W, Re, Mn, Cu, Cd, Fe, Co, Ni, Pt, Pd, Rh, Ru, Ir, or Os, and alloys or combinations thereof, either alone or with promoters such as Au, Ag, Cr, Zn, Mn, Sn, Bi, B, O and alloys or combinations thereof. Other effective hydrogenolysis catalyst materials may include the above metals combined with an alkaline earth metal oxide or adhered to catalytically active support, such as kieselguhr, or any one of the supports further described below.

The process conditions for carrying out the hydrogenolysis reaction will vary depending on the type of feedstock and desired products. In general, the hydrogenolysis reaction is conducted at temperatures of at least 110° C., or between 110° C. and 300° C., or between 170° C. and 240° C. The reaction should also be conducted under basic conditions, preferably at a pH of about 8 to about 13, or at a pH of about 10 to about 12. The reaction should also be conducted at pressures of between about 10 psig and 2400 psig, or between about 250 psig and 2000 psig, or between about 700 psig and 1600 psig. The hydrogen used in the reaction may include in situ generated $H_2$, external $H_2$, recycled $H_2$, or a combination thereof.

Production of Oxygenates

The oxygenates are prepared by reacting an aqueous feedstock solution containing water and the water soluble oxygenated hydrocarbons with hydrogen over a catalytic material to produce the desired oxygenates. Preferably, the hydrogen is generated in situ using aqueous phase reforming (in situ generated $H_2$ or APR $H_2$), or a combination of APR $H_2$, external $H_2$ or recycled $H_2$, or just simply external $H_2$ or recycled $H_2$. The term "external $H_2$" refers to hydrogen that does not originate from the feedstock solution, but is added to the reactor system from an external source. The term "recycled $H_2$" refers to unconsumed hydrogen that originates from the feedstock solution, and which is collected and then recycled back into the reactor system for further use. External $H_2$ and recycled $H_2$ may also be referred to collectively or individually as "supplemental $H_2$." In general, supplemental $H_2$ may be added for purposes of supplementing the APR hydrogen, or to substitute the inclusion of an APR hydrogen production step, or to increase the reaction pressure within the system, or to increase the molar ratio of hydrogen to carbon and/or oxygen in order to enhance the production yield of certain reaction product types, such as ketones and alcohols.

In processes utilizing APR $H_2$, the oxygenates are prepared by catalytically reacting a portion of the aqueous feedstock solution containing water and the water soluble oxygenated hydrocarbons in the presence of an APR catalyst at a reforming temperature and reforming pressure to produce the APR $H_2$, and catalytically reacting the APR $H_2$ (and recycled $H_2$ and/or external $H_2$) with a portion of the feedstock solution in the presence of a deoxygenation catalyst at a deoxygenation temperature and deoxygenation pressure to produce the desired oxygenates. In systems utilizing recycled $H_2$ or external $H_2$ as a hydrogen source, the oxygenates are simply prepared by catalytically reacting the recycled $H_2$ and/or external $H_2$ with the feedstock solution in the presence of the deoxygenation catalyst at the deoxygenation temperatures and pressures. In each of the above, the oxygenates may also include recycled oxygenates (recycled $C_{1+}O_{1-3}$ hydrocarbons). Unless otherwise indicated, any discussions of APR catalysts and deoxygenation catalysts are non-limiting examples of suitable catalytic materials.

The deoxygenation catalyst is preferably a heterogeneous catalyst having one or more materials capable of catalyzing a reaction between hydrogen and the oxygenated hydrocarbon to remove one or more of the oxygen atoms from the oxygenated hydrocarbon to produce alcohols, ketones, aldehydes, furans, carboxylic acids, hydroxy carboxylic acids, diols and triols. In general, the materials will be adhered to a support and may include, without limitation, Cu, Re, Fe, Ru, Ir, Co, Rh, Pt, Pd, Ni, W, Os, Mo, Ag, Au, alloys and combinations thereof. The deoxygenation catalyst may include these elements alone or in combination with one or more Mn, Cr, Mo, W, V, Nb, Ta, Ti, Zr, Y, La, Sc, Zn, Cd, Ag, Au, Sn, Ge, P, Al, Ga, In, Tl, and combinations thereof. In one embodiment, the deoxygenation catalyst includes Pt, Ru, Cu, Re, Co, Fe, Ni, W or Mo. In yet another embodiment, the deoxygenation catalyst includes Fe or Re and at least one transition metal selected from Ir, Ni, Pd, P, Rh, and Ru. In another embodiment, the catalyst includes Fe, Re and at least Cu or one Group VIIIB transition metal. The support may be any one of the supports further described below, including a nitride, carbon, silica, alumina, zirconia, titania, vanadia, ceria, zinc oxide, chromia, boron nitride, heteropolyacids, kieselguihr, hydroxyapatite, and mixtures thereof. The deoxygenation catalyst may also be atomically identical to the APR catalyst or the condensation catalyst.

The deoxygenation catalyst may also be a bi-functional catalyst. For example, acidic supports (e.g., supports having low isoelectric points) are able to catalyze dehydration reactions of oxygenated compounds, followed by hydrogenation reactions on metallic catalyst sites in the presence of $H_2$, again leading to carbon atoms that are not bonded to oxygen atoms. The bi-functional dehydration/hydrogenation pathway consumes $H_2$ and leads to the subsequent formation of various polyols, diols, ketones, aldehydes, alcohols and cyclic ethers, such as furans and pyrans. Catalyst examples include tungstated zirconia, titania zirconia, sulfated zirconia, acidic alumina, silica-alumina, zeolites and heteropolyacid supports. Heteropolyacids are a class of solid-phase acids exemplified by such species as $H_{3+x}PMo_{12-x}V_xO_{40}$, $H_4SiW_{12}O_{40}$, $H_3PW_{12}O_{40}$, and $H_6P2W_{18}O_{62}$. Heteropolyacids are solid-phase acids having a well-defined local structure, the most common of which is the tungsten-based Keggin structure.

Loading of the first element (i.e., Cu, Re, Fe, Ru, Ir, Co, Rh, Pt, Pd, Ni, W, Os, Mo, Ag, Au, alloys and combinations thereof) is in the range of 0.25 wt % to 25 wt % on carbon, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second element (i.e., Mn, Cr, Mo, W, V, Nb, Ta, Ti, Zr, Y, La, Sc, Zn, Cd, Ag, Au, Sn, Ge, P, Al, Ga, In, TI, and combinations thereof) is in the range of 0.25-to-1 to 10-to-1, including any ratios between, such as 0.50, 1.00, 2.50, 5.00, and 7.50-to-1. If the catalyst is adhered to a support, the combination of the catalyst and the support is from 0.25 wt % to 10 wt % of the primary element.

To produce oxygenates, the oxygenated hydrocarbon is combined with water to provide an aqueous feedstock solution having a concentration effective for causing the formation of the desired reaction products. The water-to-carbon ratio on a molar basis is preferably from about 0.5:1 to about 100:1, including ratios such as 1:1, 2:1, 3:1, 4:1, 5:1, 6:1, 7:1, 8:1, 9:1, 10:1, 15:1, 25:1, 50:1 75:1, 100:1, and any ratios there-between. The feedstock solution may also be characterized as a solution having at least 1.0 weight percent (wt %) of the total solution as an oxygenated hydrocarbon. For instance, the solution may include one or more oxygenated hydrocarbons, with the total concentration of the oxygenated hydrocarbons in the solution being at least about 1%, 5%, 10%, 20%, 30%, 40%, 50%, 60%, 70%, 80% or greater by weight, including any percentages between, and depending on the oxygenated hydrocarbons used. In one embodiment, the feedstock solution includes at least about 10%, 20%, 30%, 40%, 50%, or 60% of a sugar, such as glucose, fructose, sucrose or xylose, or a sugar alcohol, such as sorbitol, mannitol, glycerol or xylitol, by weight. Water-to-carbon ratios and percentages outside of the above stated ranges are also included. Preferably the balance of the feedstock solution is water. In some embodiments, the feedstock solution consists essentially of water, one or more oxygenated hydrocarbons and, optionally, one or more feedstock modifiers described herein, such as alkali or hydroxides of alkali or alkali earth salts or acids. The feedstock solution may also include recycled oxygenated hydrocarbons recycled from the reactor system. The feedstock solution may also contain negligible amounts of hydrogen, preferably less than about 1.5 mole of hydrogen per mole of feedstock. In the preferred embodiments, hydrogen is not added to the feedstock solution.

The feedstock solution is reacted with hydrogen in the presence of the deoxygenation catalyst at deoxygenation temperature and pressure conditions, and weight hourly space velocity, effective to produce the desired oxygenates. The specific oxygenates produced will depend on various factors, including the feedstock solution, reaction temperature, reaction pressure, water concentration, hydrogen concentration, the reactivity of the catalyst, and the flow rate of the feedstock solution as it affects the space velocity (the mass/volume of reactant per unit of catalyst per unit of time), gas hourly space velocity (GHSV), and weight hourly space velocity (WHSV). For example, an increase in flow rate, and thereby a reduction of feedstock exposure to the catalysts over time, will limit the extent of the reactions which may occur, thereby causing increased yield for higher level diols and triols, with a reduction in ketone and alcohol yields.

The deoxygenation temperature and pressure are preferably selected to maintain at least a portion of the feedstock in the liquid phase at the reactor inlet. It is recognized, however, that temperature and pressure conditions may also be selected to more favorably produce the desired products in the vapor-phase. In general, the reaction should be conducted at process conditions wherein the thermodynamics of the proposed reaction are favorable. For instance, the minimum pressure required to maintain a portion of the feedstock in the liquid phase will likely vary with the reaction temperature. As temperatures increase, higher pressures will generally be required to maintain the feedstock in the liquid phase, if desired. Pressures above that required to maintain the feedstock in the liquid phase (i.e., vapor-phase) are also suitable operating conditions.

In condensed phase liquid reactions, the pressure within the reactor must be sufficient to maintain the reactants in the condensed liquid phase at the reactor inlet. For liquid phase reactions, the reaction temperature may be from about 80° C. to 300° C., and the reaction pressure from about 72 psig to 1300 psig. In one embodiment, the reaction temperature is between about 120° C. and 300° C., or between about 200° C. and 280° C., or between about 220° C. and 260° C., and the reaction pressure is preferably between about 72 and 1200 psig, or between about 145 and 1200 psig, or between about 200 and 725 psig, or between about 365 and 700 psig, or between about 600 and 650 psig.

For vapor phase reactions, the reaction should be carried out at a temperature where the vapor pressure of the oxygenated hydrocarbon is at least about 0.1 atm (and preferably a good deal higher), and the thermodynamics of the reaction are favorable. This temperature will vary depending upon the specific oxygenated hydrocarbon compound used, but is generally in the range of from about 100° C. to 600° C. for vapor phase reactions. Preferably, the reaction temperature is between about 120° C. and about 300° C., or between about 200° C. and about 280° C., or between about 220° C. and about 260° C.

In another embodiment, the deoxygenation temperature is between about 100° C. and 400° C., or between about 120° C. and 300° C., or between about 200° C. and 280° C., and the reaction pressure is preferably between about 72 and 1300 psig, or between about 72 and 1200 psig, or between about 200 and 725 psig, or between about 365 and 700 psig.

A condensed liquid phase method may also be performed using a modifier that increases the activity and/or stability of the catalyst system. It is preferred that the water and the oxygenated hydrocarbon are reacted at a suitable pH of from about 1.0 to about 10.0, including pH values in increments of 0.1 and 0.05 between, and more preferably at a pH of from about 4.0 to about 10.0. Generally, the modifier is added to the feedstock solution in an amount ranging from about 0.1% to about 10% by weight as compared to the total weight of the catalyst system used, although amounts outside this range are included within the present invention.

In general, the reaction should be conducted under conditions where the residence time of the feedstock solution over the catalyst is appropriate to generate the desired products. For example, the WHSV for the reaction may be at least about 0.1 gram of oxygenated hydrocarbon per gram of catalyst per hour, and more preferably the WHSV is about 0.1 to 40.0 g/g hr, including a WHSV of about 0.25, 0.5, 0.75, 1.0, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 20, 25, 30, 35.40 g/g hr.

The hydrogen used in the deoxygenation reaction is preferably in-situ generated $H_2$, but may also be external or recycled $H_2$. When present, the amount of external $H_2$ is preferably provided sparingly. Most preferably, the amount of external $H_2$ is provided in amounts that provide less than one hydrogen atom per oxygen atom in all of the oxygenated hydrocarbons in the feedstock stream prior to contacting the deoxygenation catalyst. For example, the molar ratio between the external $H_2$ and the total water-soluble oxygenated hydrocarbons in the feedstock solution is preferably selected to provide no more than one hydrogen atom per oxygen atom in the oxygenated hydrocarbon. The molar ratio of the oxygenated hydrocarbons in the feedstock to the external $H_2$ introduced to the feedstock is also preferably not more than 1:1, or more preferably up to 2:1, 3:1, 5:1, 10:1, 20:1 or greater (including 4:1, 6:1, 7:1, 8:1, 9:1, 11:1, 12:1, 13:1, 14:1, 15:1, 16:1, 17:1, 18:1 and 19:1). The amount (moles) of external $H_2$ introduced to the feedstock is between 0-100%, 0-95%, 0-90%, 0-85%, 0-80%, 0-75%, 0-70%, 0-65%, 0-60%, 0-55%, 0-50%, 0-45%, 0-40%, 0-35%, 0-30%, 0-25%, 0-20%, 0-15%, 0-10%, 0-5%, 0-2%, or 0-1% of the total number of moles of the oxygenated hydrocarbon(s) in the feedstock, including all intervals between. When the feedstock solution, or any portion thereof, is reacted with APR hydrogen and external $H_2$, the molar ratio of APR hydrogen to external $H_2$ is at least 1:20; 1:15, 1:10, 1:5; 1:3, 1:2, 1:1, 2:1, 3:1, 5:1, 10:1, 15:1, 20:1, and ratios between (including 4:1, 6:1, 7:1, 8:1, 9:1, 11:1, 12:1, 13:1, 14:1, 15:1, 16:1, 17:1, 18:1 and 19:1, and vice-versa). Preferably, the oxygenated hydrocarbon is reacted with $H_2$ in the presence of an insignificantly effective amount of external $H_2$.

The amount of external $H_2$ (or supplemental $H_2$) added may be calculated by considering the concentration of the oxygenated hydrocarbons in the feedstock solution. Preferably, the amount of supplemental $H_2$ added should provide a molar ratio of oxygen atoms in the oxygenated hydrocarbons to moles of hydrogen atoms (i.e., 2 oxygen atoms per molecule of $H_2$ gas) of less than or equal to 1.0. For example, where the feedstock is an aqueous solution consisting of glycerol (3 oxygen atoms), the amount of supplemental $H_2$ added to the feedstock is preferably not more than about 1.5 moles of $H_2$ per mole of glycerol ($C_3H_8O_3$), and preferably not more than about 1.25, 1.0, 0.75, 0.50 or 0.25. In general, the amount of supplemental $H_2$ added is less than 0.75-times, and more preferably not more than 0.67, 0.50, 0.33, 0.30, 0.25, 0.20, 0.15, 0.10, 0.05, 0.01-times the amount of total $H_2$ (APR $H_2$ and supplemental $H_2$) that would provide a 1:1 atomic ratio of oxygen to hydrogen atoms.

The amount of APR $H_2$ within a reactor may be identified or detected by any suitable method. APR $H_2$ may be determined based on the composition of the product stream as a function of the composition of the feedstock stream, the catalyst composition(s) and the reaction conditions, independent of the actual reaction mechanism occurring within the feedstock stream. The amount of APR $H_2$ may be calculated based on the catalyst, reaction conditions (e.g., flow rate, temperature, pressure, etc.) and the contents of the feedstock and the reaction products. For example, the feedstock may be contacted with the APR catalyst (e.g., platinum) to generate APR $H_2$ in situ and a first reaction product stream in the absence of a deoxygenation catalyst. The feedstock may also be contacted with both the APR catalyst and the deoxygenation catalyst to produce a second reaction product stream. By comparing the composition of the first reaction product stream and the second reaction product stream at comparable reaction conditions, one may identify the presence of APR $H_2$ and calculate the amount of APR $H_2$ produced. For example, an increase in the amount of oxygenated compounds with greater degrees of hydrogenation in the reaction product compared to the feedstock components may indicate the presence of APR $H_2$.

In-Situ Hydrogen Production

One advantage of the present invention is that it allows for the production and use of in-situ generated $H_2$. The APR $H_2$ is produced from the feedstock under aqueous phase reforming conditions using an aqueous phase reforming catalyst (APR catalyst). The APR catalyst is preferably a heterogeneous catalyst capable of catalyzing the reaction of water and oxygenated hydrocarbons to form $H_2$ under the conditions described below. In one embodiment, the APR catalyst includes a support and at least one Group VIIIB metal, Fe, Ru, Os, Ir, Co, Rh, Pt, Pd, Ni, alloys and combinations thereof. The APR catalyst may also include at least one additional material from Group VIIIB, Group VIIB, Group VIB, Group VB, Group IVB, Group IIB, Group IB, Group IVA or Group VA metals, such as Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, alloys and combinations thereof. The preferred Group VIIB metal includes Re, Mn, or combinations thereof. The preferred Group VIB metal includes Cr, Mo, W, or a combination thereof. The preferred Group VIIIB metals include Pt, Rh, Ru, Pd, Ni, or combinations thereof. The supports may include any one of the catalyst supports described below, depending on the desired activity of the catalyst system.

The APR catalyst may also be atomically identical to the deoxygenation catalyst or the condensation catalyst. For instance, the APR and deoxygenation catalyst may include Pt alloyed or admixed with Ni, Ru, Cu, Fe, Rh, Re, alloys and combinations thereof. The APR catalyst and deoxygenation catalyst may also include Ru alloyed or admixed with Ge, Bi, B, Ni, Sn, Cu, Fe, Rh, Pt, alloys and combinations thereof. The APR catalyst may also include Ni alloyed or admixed with Sn, Ge, Bi, B, Cu, Re, Ru, Fe, alloys and combinations thereof.

Preferred loading of the primary Group VIIIB metal is in the range of 0.25 wt % to 25 wt % on carbon, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second material is in the range of 0.25-to-1 to 10-to-1, including ratios between, such as 0.50, 1.00, 2.50, 5.00, and 7.50-to-1.

A preferred catalyst composition is further achieved by the addition of oxides of Group IIIB, and associated rare earth oxides. In such event, the preferred components would be oxides of either lanthanum or cerium. The preferred atomic ratio of the Group IIIB compounds to the primary Group VIIIB metal is in the range of 0.25-to-1 to 10-to-1, including ratios between, such as 0.50, 1.00, 2.50, 5.00, and 7.50-to-1.

Another preferred catalyst composition is one containing platinum and rhenium. The preferred atomic ratio of Pt to Re is in the range of 0.25-to-1 to 10-to-1, including ratios therebetween, such as 0.50, 1.00, 2.50, 5.00, and 7.00-to-1. The preferred loading of the Pt is in the range of 0.25 wt % to 5.0 wt %, with weight percentages of 0.10% and 0.05% between, such as 0.35%, 0.45%, 0.75%, 1.10%, 1.15%, 2.00%, 2.50%, 3.0%, and 4.0%.

Preferably, the APR catalyst and the deoxygenation catalyst are of the same atomic formulation. The catalysts may also be of different formulations. In such event, the preferred atomic ratio of the APR catalyst to the deoxygenation catalyst is in the range of 5:1 to 1:5, such as, without limitation, 4.5:1, 4.0:1, 3.5:1, 3.0:1, 2.5:1, 2.0:1, 1.5:1, 1:1, 1:1.5, 1:2.0, 1:2.5, 1:3.0, 1:3.5, 1:4.0, 1:4.5, and any amounts between.

Similar to the deoxygenation reactions, the temperature and pressure conditions are preferably selected to maintain at least a portion of the feedstock in the liquid phase at the reactor inlet. The reforming temperature and pressure conditions may also be selected to more favorably produce the desired products in the vapor-phase. In general, the APR reaction should be conducted at a temperature where the thermodynamics are favorable. For instance, the minimum pressure required to maintain a portion of the feedstock in the liquid phase will vary with the reaction temperature. As temperatures increase, higher pressures will generally be required to maintain the feedstock in the liquid phase. Any pressure above that required to maintain the feedstock in the liquid phase (i.e., vapor-phase) is also a suitable operating pressure. For vapor phase reactions, the reaction should be conducted at a reforming temperature where the vapor pressure of the oxygenated hydrocarbon compound is at least about 0.1 atm (and preferably a good deal higher), and the thermodynamics of the reaction are favorable. The temperature will vary depending upon the specific oxygenated hydrocarbon compound used, but is generally in the range of from about 100° C. to 450° C., or from about 100° C. to 300° C., for reactions taking place in the vapor phase. For liquid phase reactions, the reaction temperature may be from about 80° C. to 400° C., and the reaction pressure from about 72 psig to 1300 psig.

In one embodiment, the reaction temperature is between about 100° C. and 400° C., or between about 120° C. and 300° C., or between about 200° C. and 280° C., or between about 150° C. and 270° C. The reaction pressure is preferably between about 72 and 1300 psig, or between about 72 and 1200 psig, or between about 145 and 1200 psig, or between about 200 and 725 psig, or between about 365 and 700 psig, or between about 600 and 650 psig.

A condensed liquid phase method may also be performed using a modifier that increases the activity and/or stability of the APR catalyst system. It is preferred that the water and the oxygenated hydrocarbon are reacted at a suitable pH of from about 1.0 to 10.0, or at a pH of from about 4.0 to 10.0, including pH value increments of 0.1 and 0.05 between. Generally, the modifier is added to the feedstock solution in an amount ranging from about 0.1% to about 10% by weight as compared to the total weight of the catalyst system used, although amounts outside this range are included within the present invention.

Alkali or alkali earth salts may also be added to the feedstock solution to optimize the proportion of hydrogen in the reaction products. Examples of suitable water-soluble salts include one or more selected from the group consisting of an alkali or an alkali earth metal hydroxide, carbonate, nitrate, or chloride salt. For example, adding alkali (basic) salts to provide a pH of about pH 4.0 to about pH 10.0 can improve hydrogen selectivity of reforming reactions.

The addition of acidic compounds may also provide increased selectivity to the desired reaction products in the hydrogenation reactions described below. It is preferred that the water-soluble acid is selected from the group consisting of nitrate, phosphate, sulfate, chloride salts, and mixtures thereof. If an acidic modifier is used, it is preferred that it be present in an amount sufficient to lower the pH of the aqueous feed stream to a value between about pH 1.0 and about pH 4.0. Lowering the pH of a feed stream in this manner may increase the proportion of oxygenates in the final reaction products.

In general, the reaction should be conducted under conditions where the residence time of the feedstock solution over the APR catalyst is appropriate to generate an amount of APR hydrogen sufficient to react with a second portion of the feedstock solution over the deoxygenation catalyst to provide the desired oxygenates. For example, the WHSV for the reaction may be at least about 0.1 gram of oxygenated hydrocarbon per gram of APR catalyst, and preferably between about 1.0 to 40.0 grams of oxygenated hydrocarbon per gram of APR catalyst, and more preferably between about 0.5 to 8.0 grams of oxygenated hydrocarbon per gram of APR catalyst. In terms of scaled-up production, after start-up, the APR reactor system should be process controlled so that the reactions proceed at steady-state equilibrium.

Condensation Step

The oxygenates produced are then converted into $C_{4+}$ compounds by condensation. Without being limited to any specific theories, it is believed that the acid condensation reactions generally consist of a series of steps involving: (a) the dehydration of oxygenates to olefins; (b) oligomerization of the olefins; (c) cracking reactions; (d) cyclization of larger olefins to form aromatics; (e) paraffin isomerization; and (f) hydrogen-transfer reactions to form paraffins. Basic condensation reactions are believed to generally consist of a series of steps involving: (1) aldol condensation to form a β-hydroxyketone or β-hydroxyaldehyde; (2) dehydration of the β-hydroxyketone or β-hydroxyaldehyde to form a conjugated enone; (3) hydrogenation of the conjugated enone to form a ketone or aldehyde, which may participate in further condensation reactions or conversion to an alcohol or hydrocarbon; and (4) hydrogenation of carbonyls to alcohols, or vice-versa. Acid-base condensation reactions are believed to generally involve any of the previous acidic and/or basic reactions steps.

Production of the $C_{4+}$ compounds occurs by condensation of the oxygenates in the presence of a condensation catalyst. The condensation catalyst will generally be a catalyst capable of forming longer chain compounds by linking two oxygen containing species through a new carbon-carbon bond, and converting the resulting compound to a hydrocarbon, alcohol or ketone, such as an acid catalyst, basic catalyst or a multifunctional catalyst having both acid and base functionality. The condensation catalyst may include, without limitation, carbides, nitrides, zirconia, alumina, silica, aluminosilicates, phosphates, zeolites, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and combinations thereof. The condensation catalyst may include the above alone or in combination with a modifier, such as Ce, La, Y, Sc, P, B, Bi, Li, Na, K, Rb, Cs, Mg, Ca, Sr, Ba, and combinations thereof. The condensation catalyst may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide a metal functionality. The condensation catalyst may also be atomically identical to the APR catalyst and/or the deoxygenation catalyst.

The condensation catalyst may be self-supporting (i.e., the catalyst does not need another material to serve as a support), or may require a separate support suitable for suspending the catalyst in the reactant stream. One particularly beneficial support is silica, especially silica having a high surface area (greater than 100 square meters per gram), obtained by sol-gel synthesis, precipitation or fuming. In other embodiments, particularly when the condensation catalyst is a powder, the catalyst system may include a binder to assist in forming the catalyst into a desirable catalyst shape. Applicable forming processes include extrusion, pelletization, oil dropping, or other known processes. Zinc oxide, alumina, and a peptizing agent may also be mixed together and extruded to produce a formed material. After drying, this material is calcined at a temperature appropriate for formation of the catalytically active phase, which usually requires temperatures in excess of 450° C. Other catalyst supports may include those described in further detail below.

Acid Catalysts

The acid condensation reaction is performed using acidic catalysts. The acid catalysts may include, without limitation, aluminosilicates (zeolites), silica-alumina phosphates (SAPO), aluminum phosphates (ALPO), amorphous silica alumina, zirconia, sulfated zirconia, tungstated zirconia, tungsten carbide, molybdenum carbide, titania, acidic alumina, phosphated alumina, phosphated silica, sulfated carbons, phosphated carbons, acidic resins, heteropolyacids, inorganic acids, and combinations thereof. In one embodiment, the catalyst may also include a modifier, such as Ce, Y, Sc, La, P, B, Bi, Li, Na, K, Rb, Cs, Mg, Ca, Sr, Ba, and combinations thereof. The catalyst may also be modified by the addition of a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide metal functionality, and/or sulfides and oxide of Ti, Zr, V, Nb, Ta, Mo, Cr, W, Mn, Re, Al, Ga, In, Fe, Co, Ir, Ni, Si, Cu, Zn, Sn, Cd, P, and combinations thereof. Gallium has also been found to be particularly useful as a promoter for the present process. The acid catalyst may be homogenous, self-supporting or adhered to any one of the supports further described below, including supports containing carbon, silica, alumina, zirconia, titania, vanadia, ceria, nitride, boron nitride, heteropolyacids, alloys and mixtures thereof.

Ga, In, Zn, Fe, Mo, Ag, Au, Ni, P, Sc, Y, Ta, and lanthanides may also be exchanged onto zeolites to provide a zeolite catalyst having activity. The term "zeolite" as used herein refers not only to microporous crystalline aluminosilicate but also for microporous crystalline metal-containing aluminosilicate structures, such as galloaluminosilicates and gallosilicates. Metal functionality may be provided by metals such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof.

Examples of suitable zeolite catalysts include ZSM-5, ZSM-11, ZSM-12, ZSM-22, ZSM-23, ZSM-35 and ZSM-48. Zeolite ZSM-5, and the conventional preparation thereof, is described in U.S. Pat. Nos. 3,702,886; Re. 29,948 (highly siliceous ZSM-5); 4,100,262 and 4,139,600, all incorporated herein by reference. Zeolite ZSM-11, and the conventional preparation thereof, is described in U.S. Pat. No. 3,709,979, which is also incorporated herein by reference. Zeolite ZSM-12, and the conventional preparation thereof, is described in U.S. Pat. No. 3,832,449, incorporated herein by reference. Zeolite ZSM-23, and the conventional preparation thereof, is described in U.S. Pat. No. 4,076,842, incorporated herein by reference. Zeolite ZSM-35, and the conventional preparation thereof, is described in U.S. Pat. No. 4,016,245, incorporated herein by reference. Another preparation of ZSM-35 is described in U.S. Pat. No. 4,107,195, the disclosure of which is incorporated herein by reference. ZSM-48, and the conventional preparation thereof, is taught by U.S. Pat. No. 4,375,573, incorporated herein by reference. Other examples of zeolite catalysts are described in U.S. Pat. No. 5,019,663 and U.S. Pat. No. 7,022,888, also incorporated herein by reference.

As described in U.S. Pat. No. 7,022,888, the acid catalyst may be a bifunctional pentasil zeolite catalyst including at least one metallic element from the group of Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, or a modifier from the group of Ga, In, Zn, Fe, Mo, Au, Ag, Y, Sc, Ni, P, Ta, lanthanides, and combinations thereof. The zeolite preferably has a strong acidic and dehydrogenation sites, and may be used with reactant streams containing and an oxygenated hydrocarbon at a temperature of below 500° C. The bifunctional pentasil zeolite may have ZSM-5, ZSM-8 or ZSM-11 type crystal structure consisting of a large number of 5-membered oxygen-rings, i.e., pentasil rings. The zeolite with ZSM-5 type structure is a particularly preferred catalyst. The bifunctional pentasil zeolite catalyst is preferably Ga and/or In-modified ZSM-5 type zeolites such as Ga and/or In-impregnated H-ZSM-5, Ga and/or In-exchanged H-ZSM-5, H-gallosilicate of ZSM-5 type structure and H-galloaluminosilicate of ZSM-5 type structure. The bifunctional ZSM-5 type pentasil zeolite may contain tetrahedral aluminum and/or gallium present in the zeolite framework or lattice and octahedral gallium or indium. The octahedral sites are preferably not present in the zeolite framework but are present in the zeolite channels in a close vicinity of the zeolitic protonic acid sites, which are attributed to the presence of tetrahedral aluminum and gallium in the zeolite. The tetrahedral or framework Al and/or Ga is believed to be responsible for the acid function of zeolite and octahedral or non-framework Ga and/or In is believed to be responsible for the dehydrogenation function of the zeolite.

In one embodiment, the condensation catalyst may be a H-galloaluminosilicate of ZSM-5 type bifunctional pentasil zeolite having framework (tetrahedral) Si/Al and Si/Ga mole ratio of about 10-100 and 15-150, respectively, and non-framework (octahedral) Ga of about 0.5-5.0 wt. %. When these pentasil H-galloaluminosilicate zeolites are used as a condensation catalyst, the density of strong acid sites can be controlled by the framework Al/Si mole ratio: the higher the Al/Si ratio, the higher the density of strong acid sites. The highly dispersed non-framework gallium oxide species can be obtained by the degalliation of the zeolite by its pre-treatment with $H_2$ and steam. The zeolite containing strong acid sites with high density and also highly dispersed non-framework gallium oxide species in close proximity of the zeolite acid site is preferred. The catalyst may optionally contain any binder such as alumina, silica or clay material. The catalyst can be used in the form of pellets, extrudates and particles of different shapes and sizes.

The acidic catalysts may include one or more zeolite structures comprising cage-like structures of silica-alumina. Zeolites are crystalline microporous materials with well-defined pore structure. Zeolites contain active sites, usually acid sites, which can be generated in the zeolite framework. The strength and concentration of the active sites can be tailored for particular applications. Examples of suitable zeolites for condensing secondary alcohols and alkanes may comprise aluminosilicates optionally modified with cations, such as Ga, In, Zn, Mo, and mixtures of such cations, as described, for example, in U.S. Pat. No. 3,702,886, which is incorporated herein by reference. As recognized in the art, the structure of the particular zeolite or zeolites may be altered to provide different amounts of various hydrocarbon species in the product mixture. Depending on the structure of the zeolite catalyst, the product mixture may contain various amounts of aromatic and cyclic hydrocarbons.

Alternatively, solid acid catalysts such as alumina modified with phosphates, chloride, silica, and other acidic oxides could be used in practicing the present invention. Also, either sulfated zirconia or tungstated zirconia may provide the necessary acidity. Re and Pt/Re catalysts are also useful for promoting condensation of oxygenates to $C_{5+}$ hydrocarbons and/or $C_{5+}$ mono-oxygenates. The Re is sufficiently acidic to promote acid-catalyzed condensation. Acidity may also be added to activated carbon by the addition of either sulfates or phosphates.

Base Catalysts

The base condensation reaction is performed using a base catalyst. The base catalyst includes at least Li, Na, K, Cs, B, Rb, Mg, Ca, Sr, Si, Ba, Al, Zn, Ce, La, Y, Sc, Y, Zr, Ti, hydrotalcite, zinc-aluminate, phosphate, base-treated aluminosilicate zeolite, a basic resin, basic nitride, alloys or combinations thereof. The base catalyst may also include an oxide of Ti, Zr, V, Nb, Ta, Mo, Cr, W, Mn, Re, Al, Ga, In, Co, Ni, Si, Cu, Zn, Sn, Cd, Mg, P, Fe, and combinations thereof. In one embodiment, the condensation catalyst further includes a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof. Preferred Group IA materials include Li, Na, K, Cs and Rb. Preferred Group IIA materials include Mg, Ca, Sr and Ba. Preferred Group IIB materials include Zn and Cd. Preferred Group IIIB materials include Y and La. Basic resins include resins that exhibit basic functionality, such as Amberlyst. The base catalyst may be self-supporting or adhered to any one of the supports further described below, including supports containing carbon, silica, alumina, zirconia, titania, vanadia, ceria, nitride, boron nitride, heteropolyacids, alloys and mixtures thereof.

The base catalyst may also include zeolites and other microporous supports that contain Group IA compounds, such as Li, Na, K, Cs and Rb. Preferably, the Group IA material is present in an amount greater than that required to neutralize the acidic nature of the support. These materials may be used in any combination, and also in combination with alumina or silica. A metal function may also be provided by the addition of group VIIIB metals, or Cu, Ga, In, Zn or Sn.

In one embodiment, the condensation catalyst is derived from the combination of MgO and $Al_2O_3$ to form a hydrotalcite material. Another preferred material contains ZnO and $Al_2O_3$ in the form of a zinc aluminate spinel. Yet another preferred material is a combination of ZnO, $Al_2O_3$, and CuO. Each of these materials may also contain an additional metal function provided by a Group VIIIB metal, such as Pd or Pt. In one embodiment, the base catalyst is a metal oxide containing Cu, Ni, Zn, V, Zr, or mixtures thereof. In another embodiment, the base catalyst is a zinc aluminate metal containing Pt, Pd Cu, Ni, or mixtures thereof.

Preferred loading of the primary metal is in the range of 0.10 wt % to 25 wt %, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second metal, if any, is in the range of 0.25-to-1 to 10-to-1, including ratios there between, such as 0.50, 1.00, 2.50, 5.00, and 7.50-to-1.

Acid-Base Catalysts

The acid-base condensation reaction is performed using a multi-functional catalyst having both acid and base functionality. The acid-base catalyst may include hydrotalcite, zinc-aluminate, phosphate, Li, Na, K, Cs, B, Rb, Mg, Si, Ca, Sr, Ba, Al, Ce, La, Sc, Y, Zr, Ti, Zn, Cr, and combinations thereof. In further embodiments, the acid-base catalyst may also include one or more oxides from the group of Ti, Zr, V, Nb, Ta, Mo, Cr, W, Mn, Re, Al, Ga, In, Fe, Co, Ir, Ni, Si, Cu, Zn, Sn, Cd, P, and combinations thereof. The acid-base catalyst may also include a metal functionality provided by Cu, Ag, Au, Pt, Ni, Fe, Co, Ru, Zn, Cd, Ga, In, Rh, Pd, Ir, Re, Mn, Cr, Mo, W, Sn, Os, alloys or combinations thereof. In one embodiment, the catalyst further includes Zn, Cd or phosphate. In one embodiment, the condensation catalyst is a metal oxide containing Pd, Pt, Cu or Ni, and even more preferably an aluminate or zirconium metal oxide containing Mg and Cu, Pt, Pd or Ni. The acid-base catalyst may also include a hydroxyapatite (HAP) combined with any one or more of the above metals. The acid-base catalyst may be self-supporting or adhered to any one of the supports further described below, including supports containing carbon, silica, alumina, zirconia, titania, vanadia, ceria, nitride, boron nitride, heteropolyacids, alloys and mixtures thereof.

The condensation catalyst may also include zeolites and other microporous supports that contain Group IA compounds, such as Li, NA, K, Cs and Rb. Preferably, the Group IA material is present in an amount less than that required to neutralize the acidic nature of the support. A metal function may also be provided by the addition of group VIIIB metals, or Cu, Ga, In, Zn or Sn.

In one embodiment, the condensation catalyst is derived from the combination of MgO and $Al_2O_3$ to form a hydrotalcite material. Another preferred material contains a combination of MgO and $ZrO_2$, or a combination of ZnO and $Al_2O_3$. Each of these materials may also contain an additional metal function provided by copper or a Group VIIIB metal, such as Ni, Pd, Pt, or combinations of the foregoing.

If a Group IIB, VIB, VIIB, VIIIB, IIA or IVA metal is included, the loading of the metal is in the range of 0.10 wt % to 10 wt %, with weight percentages of 0.10% and 0.05% increments between, such as 1.00%, 1.10%, 1.15%, 2.00%, 2.50%, 5.00% and 7.50%, etc. If a second metal is included, the preferred atomic ratio of the second metal is in the range of 0.25-to-1 to 5-to-1, including ratios there between, such as 0.50, 1.00, 2.50 and 5.00-to-1.

Condensation Reactions

The specific $C_{4+}$ compounds produced will depend on various factors, including, without limitation, the type of oxygenates in the reactant stream, condensation temperature, condensation pressure, the reactivity of the catalyst, and the flow rate of the reactant stream as it affects the space velocity, GHSV and WHSV. Preferably, the reactant stream is contacted with the condensation catalyst at a WHSV that is appropriate to produce the desired hydrocarbon products. The WHSV is preferably at least about 0.1 grams of oxygenate in the reactant stream per hour, more preferably the WHSV is between about 0.1 to 40.0 g/g hr, including a WHSV of about 1, 2, 3, 4, 5, 6, 7, 8, 9, 10, 11, 12, 13, 14, 15, 20, 25, 30, 35 g/g hr, and increments between.

In general, the condensation reaction should be carried out at a temperature at which the thermodynamics of the proposed reaction are favorable. For condensed phase liquid reactions, the pressure within the reactor must be sufficient to maintain at least a portion of the reactants in the condensed liquid phase at the reactor inlet. For vapor phase reactions, the reaction should be carried out at a temperature where the vapor pressure of the oxygenates is at least about 0.1 atm (and preferably a good deal higher), and the thermodynamics of the reaction are favorable. The condensation temperature will vary depending upon the specific oxygenate used, but is generally in the range of from about 80° C. to 500° C. for reactions taking place in the vapor phase, and more preferably from about 125° C. to 450° C. For liquid phase reactions, the condensation temperature may be from about 80° C. to 500° C., and the condensation pressure from about 0 psig to 1200 psig. Preferably, the condensation temperature is between about 125° C. and 300° C., or between about 125° C. and 250° C., or between about 250° C. and 425° C. The reaction pressure is preferably at least about 0.1 atm, or between about 0 and 1200 psig, or between about 0 and 1000 psig, or between about 0 and 700 psig.

Varying the factors above, as well as others, will generally result in a modification to the specific composition and yields of the $C_{4+}$ compounds. For example, varying the temperature and/or pressure of the reactor system, or the particular catalyst formulations, may result in the production of $C_{4+}$ alcohols and/or ketones instead of $C_{4+}$ hydrocarbons. The $C_{4+}$ hydrocarbon product may also contain a variety of olefins, and alkanes of various sizes (typically branched alkanes). Depending upon the condensation catalyst used, the hydrocarbon product may also include aromatic and cyclic hydrocarbon compounds. The $C_{4+}$ hydrocarbon product may also contain undesirably high levels of olefins, which may lead to coking or deposits in combustion engines, or other undesirable hydrocarbon products. In such event, the hydrocarbon molecules produced may be optionally hydrogenated to reduce the ketones to alcohols and hydrocarbons, while the alcohols and unsaturated hydrocarbon may be reduced to alkanes, thereby forming a more desirable hydrocarbon product having low levels of olefins, aromatics or alcohols.

The finishing step will generally be a hydrogenation reaction that removes the remaining carbonyl group or hydroxyl group. In such event, any one of the hydrogenation catalysts described above may be used. Such catalysts may include any one or more of the following metals, Cu, Ni, Fe, Co, Ru, Pd, Rh, Pt, Ir, Os, alloys or combinations thereof, alone or with promoters such as Au, Ag, Cr, Zn, Mn, Sn, Cu, Bi, and alloys thereof, may be used in various loadings ranging from about 0.01 to about 20 wt % on a support as described above.

In general, the finishing step is carried out at finishing temperatures of between about 80° C. to 250° C., and finishing pressures in the range of about 100 psig to 2000 psig. The finishing step may be conducted in the vapor phase or liquid phase, and may use in situ generated $H_2$, external $H_2$, recycled $H_2$, or combinations thereof, as necessary.

Other factors, such as the concentration of water or undesired oxygenates, may also effect the composition and yields of the $C_{4+}$ compounds, as well as the activity and stability of the condensation catalyst. In such event, the process may include a dewatering step that removes a portion of the water prior to condensation, or a separation unit for removal of the undesired oxygenates. For instance, a separator unit, such as a phase separator, extractor, purifier or distillation column, may be installed prior to the condensation step so as to remove a portion of the water from the reactant stream containing the oxygenates. A separation unit may also be installed to remove specific oxygenates to allow for the production of a desired product stream containing hydrocarbons within a particular carbon range, or for use as end products or in other systems or processes.

$C_{4+}$ Compounds

The practice of the present invention results in the production of $C_{4+}$ alkanes, $C_{4+}$ alkenes, $C_{5+}$ cycloalkanes, $C_{5+}$ cycloalkenes, aryls, fused aryls, $C_{4+}$ alcohols, $C_{4+}$ ketones, and mixtures thereof. The $C_{4+}$ alkanes and $C_{4+}$ alkenes have from 4 to 30 carbon atoms ($C_{4-30}$ alkanes and $C_{4-30}$ alkenes) and may be branched or straight chained alkanes or alkenes. The $C_{4+}$ alkanes and $C_{4+}$ alkenes may also include fractions of $C_{4-9}$, $C_{7-14}$, $C_{12-24}$ alkanes and alkenes, respectively, with the $C_{4-9}$ fraction directed to gasoline, the $C_{7-14}$ fraction directed to jet fuels, and the $C_{12-24}$ fraction directed to diesel fuel and other industrial applications. Examples of various $C_{4+}$ alkanes and $C_{4+}$ alkenes include, without limitation, butane, butane, pentane, pentene, 2-methylbutane, hexane, hexane, 2-methylpentane, 3-methylpentane, 2,2-dimethylbutane, 2,3-dimethylbutane, heptane, heptene, octane, octene, 2,2,4,-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecane, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The $C_{5+}$ cycloalkanes and $C_{5+}$ cycloalkenes have from 5 to 30 carbon atoms and may be unsubstituted, mono-substituted or multi-substituted. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{1+}$ alkylene, a straight chain $C_{2+}$ alkylene, a phenyl or a combination thereof. In one embodiment, at least one of the substituted groups include a branched $C_{3-12}$ alkyl, a straight chain $C_{1-12}$ alkyl, a branched $C_{3-12}$ alkylene, a straight chain $C_{1-12}$ alkylene, a straight chain $C_{2-12}$ alkylene, a phenyl or a combination thereof. In yet another embodiment, at least one of the substituted groups include a branched $C_{3-4}$ alkyl, a straight chain $C_{1-4}$ alkyl, a branched $C_{3-4}$ alkylene, straight chain $C_{1-4}$ alkylene, straight chain $C_{2-4}$ alkylene, a phenyl or a combination thereof. Examples of desirable $C_{5+}$ cycloalkanes and $C_{5+}$ cycloalkenes include, without limitation, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, and isomers thereof.

Aryls will generally consist of an aromatic hydrocarbon in either an unsubstituted (phenyl), mono-substituted or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. In one embodiment, at least one of the substituted groups include a branched $C_{3-12}$ alkyl, a straight chain $C_{1-12}$ alkyl, a branched $C_{3-12}$ alkylene, a straight chain $C_{2-12}$ alkylene, a phenyl or a combination thereof. In yet another embodiment, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various aryls include, without limitation, benzene, toluene, xylene (dimethylbenzene), ethyl benzene, para xylene, meta xylene, ortho xylene, $C_9$ aromatics.

Fused aryls will generally consist of bicyclic and polycyclic aromatic hydrocarbons, in either an unsubstituted, mono-substituted or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. In another embodiment, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various fused aryls include, without limitation, naphthalene, anthracene, tetrahydronaphthalene, and decahydronaphthalene, indane, indene, and isomers thereof.

The $C_{4+}$ alcohols may also be cyclic, branched or straight chained, and have from 4 to 30 carbon atoms. In general, the $C_{4+}$ alcohols may be a compound according to the formula $R^1$—OH, wherein $R^1$ is a member selected from the group consisting of a branched $C_{4+}$ alkyl, straight chain $C_{4+}$ alkyl, a branched $C_{4+}$ alkylene, a straight chain $C_{4+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl and combinations thereof. Examples of desirable $C_{4+}$ alcohols include, without limitation, butanol, pentanol, hexanol, heptanol, octanol, nonanol, decanol, undecanol, dodecanol, tridecanol, tetradecanol, pentadecanol, hexadecanol, heptyldecanol, octyldecanol, nonyldecanol, eicosanol, uneicosanol, doeicosanol, trieicosanol, tetraeicosanol, and isomers thereof.

The $C_{4+}$ ketones may also be cyclic, branched or straight chained, and have from 4 to 30 carbon atoms. In general, the $C_{4+}$ ketone may be a compound according to the formula

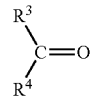

wherein $R^3$ and $R^4$ are independently a member selected from the group consisting of a branched $C_{3+}$ alkyl, a straight chain $C_{1+}$ alkyl, a branched $C_{3+}$ alkylene, a straight chain $C_{2+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl and a combination thereof. Examples of desirable $C_{4+}$ ketones include, without limitation, butanone, pentanone, hexanone, heptanone, octanone, nonanone, decanone, undecanone, dodecanone, tridecanone, tetradecanone, pentadecanone, hexadecanone, heptyldecanone, octyldecanone, nonyldecanone, eicosanone, uneicosanone, doeicosanone, trieicosanone, tetraeicosanone, and isomers thereof.

The lighter fractions of the above, primarily $C_4$-$C_9$, may be separated for gasoline use. Moderate fractions, such as $C_7$-$C_{14}$, may be separated for jet fuel, while heavier fractions, i.e., $C_{12}$-$C_{24}$, may be separated for diesel use. The heaviest fractions may be used as lubricants or cracked to produce additional gasoline and/or diesel fractions. The $C_{4+}$ compounds may also find use as industrial chemicals, whether as an intermediate or an end product. For example, the aryls toluene, xylene, ethyl benzene, para xylene, meta xylene, ortho xylene may find use a chemical intermediates for the product of plastics and other products. Meanwhile, the $C_9$ aromatics and fused aryls, such as naphthalene, anthracene, tetrahydronaphthalene, and decahydronaphthalene, may find use as solvents in industrial processes.

Catalyst Supports

In various embodiments above, the catalyst systems include a support suitable for suspending the catalyst in the feedstock solution. The support should be one that provides a stable platform for the chosen catalyst and the reaction conditions. The support may take any form which is stable at the chosen reaction conditions to function at the desired levels, and specifically stable in aqueous feedstock solutions. Such supports include, without limitation, carbon, silica, silica-alumina, alumina, zirconia, titania, ceria, vanadia, nitride, boron nitride, heteropolyacids, hydroxyapatite, zinc oxide, chromia, and mixtures thereof. Nanoporous supports such as zeolites, carbon nanotubes, or carbon fullerene may also be used.

One particularly preferred catalyst support is carbon, especially carbon supports having relatively high surface areas (greater than 100 square meters per gram). Such carbons include activated carbon (granulated, powdered, or pelletized), activated carbon cloth, felts, or fibers, carbon nanotubes or nanohoms, carbon fullerene, high surface area carbon honeycombs, carbon foams (reticulated carbon foams), and carbon blocks. The carbon may be produced via either chemical or steam activation of peat, wood, lignite, coal, coconut shells, olive pits, and oil based carbon. Another preferred support is granulated activated carbon produced from coconuts. In one embodiment, the APR and deoxygenation catalyst system consists of Pt on carbon, with the Pt being further alloyed or admixed with Ni, Ru, Cu, Fe, Rh, Re, alloys and combinations thereof.

Another preferred catalyst support is zirconia. The zirconia may be produced via precipitation of zirconium hydroxide from zirconium salts, through sol-gel processing, or any other method. The zirconia is preferably present in a crystalline form achieved through calcination of the precursor material at temperatures exceeding 400° C. and may include both tetragonal and monoclinic crystalline phases. A modifying agent may be added to improve the textural or catalytic properties of the zirconia. Such modifying agents include, without limitation, sulfate, tungstenate, phosphate, titania, silica, and oxides of Group IIIB metals, especially Ce, La, or Y. In one embodiment, the APR and deoxygenation catalyst consists of Pt on a primarily tetragonal phase silica modified zirconia, with the Pt being further alloyed or admixed with Ni, Ru, Cu, Fe, Rh, Re, alloys and combinations thereof.

Yet another preferred catalyst support is titania. The titania may be produced via precipitation from titanium salts, through sol-gel processing, or any other method. The titania is preferably present in a crystalline form and may include both anatase and rutile crystalline phases. A modifying agent may be added to improve the textural or catalytic properties of the titania. Such modifying agents include, without limitation, sulfate, silica, and oxides of Group IIIB metals, especially Ce, La, or Y. In one embodiment, the APR and oxygenate forming catalyst system consists of Ru on a primarily rutile phase titania, with the Ru being further alloyed or admixed with Ge, Bi, B, Ni, Sn, Cu, Fe, Re, Rh, Pt, alloys and combinations thereof.

Another preferred catalyst support is silica. The silica may be optionally combined with alumina to form a silica-alumina material. In one embodiment, the APR catalyst system is Pt on silica-alumina or silica, with the Pt being further alloyed or admixed with Ni, Ru, Cu, Fe, Rh, Re, alloys and combinations thereof. In another embodiment, the APR catalyst system is Ni on silica-alumina or silica, with the nickel being further alloyed or admixed with Sn, Ge, Bi, Bu, Cu, Re, Ru, Fe, alloys and combinations thereof.

The support may also be treated or modified to enhance its properties. For example, the support may be treated, as by surface-modification, to modify surface moieties, such as hydrogen and hydroxyl. Surface hydrogen and hydroxyl groups can cause local pH variations that affect catalytic efficiency. The support may also be modified, for example, by treating it with sulfates, phosphates, tungstenates, silanes, lanthanides, alkali compounds or alkali earth compounds. For carbon supports, the carbon may be pretreated with steam, oxygen (from air), inorganic acids or hydrogen peroxide to provide more surface oxygen sites. The preferred pretreatment would be to use either oxygen or hydrogen peroxide. The pretreated carbon may also be modified by the addition of oxides of Group IVB and Group VB. It is preferred to use oxides of Ti, V, Zr and mixtures thereof.

The catalyst systems, whether alone or mixed together, may be prepared using conventional methods known to those in the art. Such methods include incipient wetting, evaporative impregnation, chemical vapor deposition, wash-coating, magnetron sputtering techniques, and the like. The method chosen to fabricate the catalyst is not particularly critical to the function of the invention, with the proviso that different catalysts will yield different results, depending upon considerations such as overall surface area, porosity, etc.

Supplemental Materials

Supplemental materials and compositions ("supplements") may be added to the feedstock solution at various stages of the process in order to enhance the reaction or to drive it to the production of the desired reaction products. Supplements may include, without limitation, acids, salts and additional hydrogen or feedstock. Such supplements may be added directly to the feedstock stream prior to or contiguous with contacting the relevant catalyst, or directly to the reaction bed for the appropriate reactions.

In one embodiment, the supplement may include an additional feedstock solution for providing additional oxygenated hydrocarbons for oxygenate formation. The feedstock may include any one or more oxygenated hydrocarbons listed above, including any one or more sugar alcohols, glucose, polyols, glycerol or saccharides. For instance, the supplemental material may include glycerol. In this embodiment, crude glycerol is used to initiate the reaction and to produce hydrogen so as to avoid polluting the deoxygenation catalyst with contaminants from the crude glycerol. Purified glycerol is then added to the feedstock solution prior to or at the same time the original feedstock solution is placed in contact with the deoxygenation catalyst to increase the oxygenated hydrocarbons available for processing. It is anticipated that the opposite may be employed with the crude glycerol serving as the supplement depending on the characteristics of the APR catalyst and deoxygenation catalyst.

In another embodiment, the supplement may include additional oxygenates for the condensation reaction. The oxygenates may include any one or more oxygenates listed above. For instance, the supplemental material may include a propyl alcohol. In this embodiment, the propyl alcohol may be produced in a parallel system from a glycerol feedstock and then combined with oxygenates produced by the processing of a sorbitol feedstock in order to provide a reactant stream most effective to produce a product containing a combination of $C_{6-12}$ hydrocarbons.

In yet another embodiment, the supplemental material may include recycled oxygenates and/or oxygenated hydrocarbons not fully reacted during the production process. The oxygenates and oxygenated hydrocarbons may include any one or more of oxygenates and oxygenated hydrocarbons listed above.

In still yet another embodiment, the supplemental material may include acids and salts added to the process. The addition of acidic compounds may provide increased selectivity to the desired oxygenates and, ultimately, $C_{4+}$ compounds. Water-soluble acids may include, without limitation, nitrate, phosphate, sulfate, chloride salts, and mixtures thereof. If an optional acidic modifier is used, it is preferred that it be present in an amount sufficient to lower the pH of the aqueous feed stream to a value between about pH 1.0 and about pH 4.0. Lowering the pH of a feed stream during oxygenate formation in this manner may increase the proportion of diols, polyols, ketones or alcohols for further condensation.

Reactor System

The reactions described herein may be carried out in any reactor of suitable design, including continuous-flow, batch, semi-batch or multi-system reactors, without limitation as to design, size, geometry, flow rates, etc. The reactor system may also use a fluidized catalytic bed system, a swing bed system, fixed bed system, a moving bed system, or a combination of the above. Preferably, the present invention is practiced utilizing a continuous-flow system at steady-state equilibrium.

In a continuous flow system, the reactor system includes at least a reforming bed adapted to receive an aqueous feedstock solution to produce hydrogen, a deoxygenation bed adapted to produce oxygenates from the hydrogen and a portion of the feedstock solution, and a condensation bed to produce $C_{4+}$ compounds from the oxygenates. The reforming bed is configured to contact the aqueous feedstock solution in a vapor phase or liquid phase with the APR catalyst to provide hydrogen in a reactant stream. The deoxygenation bed is configured to receive the reactant stream for contact with the deoxygenation catalyst and production of the desired oxygenates. The condensation bed is configured to receive the reactant stream for contact with the condensation catalyst and production of the desired $C_{4+}$ compounds. For systems not involving an APR hydrogen production step, the reforming bed may be removed. For systems not involving a hydrogen or oxygenate production step, the reforming and deoxygenation beds may be removed. Because the APR catalyst, deoxygenation catalyst and condensation catalyst may also be atomically identical, the catalysts may exist as the same bed. For systems with a hydrogenation or hydrogenolysis step, an additional reaction bed may be included prior to the deoxygenation and/or reforming bed. For systems with a finishing step, an additional reaction bed for conducting the finishing process may be included after the condensation bed.

In systems producing both hydrogen and oxygenates, the condensation bed may be positioned within the same reactor vessel along with the reforming bed or in a second reactor vessel in communication with a first reactor vessel having the reforming bed. The condensation bed may be within the same reactor vessel along with the reforming or deoxygenation bed or in a separate reactor vessel in communication with the reactor vessel having the deoxygenation bed. Each reactor vessel preferably includes an outlet adapted to remove the product stream from the reactor vessel. In systems including a hydrogenation step or hydrogenolysis step, the hydrogenation or hydrogenolysis reaction bed may be within the same reactor vessel along with the reforming or deoxygenation bed or in a separate reactor vessel in communication with the reactor vessel having the reforming bed and/or deoxygenation bed. For systems with a finishing step, the finishing reaction bed may be within the same reactor vessel along with the condensation bed or in a separate reactor vessel in communication with the reactor vessel having the condensation bed.

The reactor system may also include additional outlets to allow for the removal of portions of the reactant stream to further advance or direct the reaction to the desired reaction products, and to allow for the collection and recycling of reaction byproducts for use in other portions of the system. The reactor system may also include additional inlets to allow for the introduction of supplemental materials to further advance or direct the reaction to the desired reaction products, and to allow for the recycling of reaction byproducts for use in the reforming process. For example, the system may be designed such that excess hydrogen is produced over the APR catalyst, with a portion of the excess hydrogen removed and reintroduced downstream in the process to supplement the reaction of the oxygenates over the condensation catalyst or the finishing of the condensation product to arrive at the desired $C_{4+}$ compounds. Alternatively, the system may be designed such that excess hydrogen is produced over the APR catalyst, with a portion of the excess hydrogen removed and used in other upstream processes, such as feedstock pretreatment processes and hydrogenation or hydrogenolysis reactions.

The reactor system may also include elements which allow for the separation of the reactant stream into different components which may find use in different reaction schemes or to simply promote the desired reactions. For instance, a separator unit, such as a phase separator, extractor, purifier or distillation column, may be installed prior to the condensation step to remove water from the reactant stream for purposes of advancing the condensation reaction to favor the production of hydrocarbons. A separation unit may also be installed to remove specific oxygenates to allow for the production of a desired product stream containing hydrocarbons within a particular carbon range, or for use as end products or in other systems or processes.

In one embodiment, the reaction system is configured such that the flow direction of the aqueous feedstock solution is established to ensure maximal interaction with the in-situ generated $H_2$. The reactor may be designed so that the reactant stream flows horizontally, vertical or diagonally to the gravitational plane so as to maximize the efficiency of the system. In systems where the reactant stream flows vertically or diagonally to the gravitational plan, the stream may flow either against gravity (up-flow system), with gravity (down-flow system), or a combination of both. In one preferred embodiment, the APR and/or deoxygenation reactor vessel is designed as an up-flow system while the condensation reactor vessel is designed as a down-flow system. In this embodiment, the feedstock solution first contacts a reforming bed containing the APR catalyst to produce in-situ generated $H_2$. Due to the configuration of the reactor, the APR $H_2$ is then able to, under certain conditions, percolate through a second reaction bed containing the deoxygenation catalyst at a rate greater than or equal to the feedstock solution to maximize the interaction of the feedstock solution with the $H_2$ and deoxygenation catalyst. The resulting reactant stream is then feed into the condensation reactor in a down-flow configuration for processing.

If the APR catalyst and deoxygenation catalyst are within a single chamber, the APR catalyst and deoxygenation catalyst may be placed in a stacked configuration to allow the feedstock solution to first contact the APR catalyst and then the deoxygenation catalyst, or a series of deoxygenation catalysts depending on the desired reaction products. The reaction beds for the APR catalyst and deoxygenation catalyst, or catalysts, may also be placed side-by-side dependent upon the particular flow mechanism employed. In either case, the feedstock solution may be introduced into the reaction vessel through one or more inlets, and then directed across the catalysts for processing. In another embodiment, the feedstock solution is directed across the APR catalyst to produce APR $H_2$, and then both the APR $H_2$ and the remaining feedstock solution are directed across the deoxygenation catalyst, or catalysts, to produce the desired oxygenates. In a parallel configuration, the feedstock solution may be separated to direct a first portion of the feedstock solution to the reforming bed where APR $H_2$ is produced, and a second portion to a deoxygenation bed where the desired oxygenates are produced using the in situ generated APR $H_2$. Alternatively, the reactor may be configured to accommodate the use of two separate feedstock solutions, with the first feedstock solution directed to the APR reactor vessel and the second feedstock solution directed to the deoxygenation reactor vessel. In a sequential configuration, the reactor may be designed so that the feedstock solution flows through the APR reactor vessel and into the deoxygenation reactor vessel. In embodiments employing a combined APR/deoxygenation catalyst, the generation of APR $H_2$ and oxygenates occurs simultaneously. In either of these systems, because the APR $H_2$ is produced in-situ, the pressure is provided by a pumping mechanism that also drives the feedstock solution through the reactor chambers.

FIG. 6 is a process diagram illustrating one potential reactor system useful in practicing the invention. A feed stream of oxygenated hydrocarbons 1 (with or without water) is mixed with a stream of recycled water and recycled oxygenates at 2 to provide an aqueous feedstock solution 3. The feedstock solution 3 is then hydrogenated in a pretreatment step 4 to provide a feedstock solution 5 that is more readily converted to the desired oxygenates. The $H_2$ for the hydrogenation step may derive from an external source 22 or hydrogen recycled from the system as illustrated in steps 13-21 below. The feedstock solution 5 is reacted in a reactor vessel 8 that contains an APR catalyst and a deoxygenation catalyst to produce product stream 7 containing water, $H_2$, carbon dioxide, hydrocarbons and oxygenates. Water in product stream 7 is then removed at 8 to provide a product stream 10 containing oxygenates, hydrogen, carbon dioxide and hydrocarbons. Water from dewatering step 8 is then recycled at 9 and 15 for mixing with the stream of oxygenated hydrocarbons at 2. Product stream 10 is then passed through reactor vessel 11, which includes a condensation catalyst to produce product stream 12 containing $C_{4+}$ compounds, water, $H_2$ and carbon dioxide. Product stream 12 is then passed through a three-phase separator 13 to separate the non-condensable gases 16 (i.e., hydrogen, carbon dioxide, methane, ethane, and propane) from the hydrocarbon product stream 14 containing $C_{4+}$ compounds and water 15. Water 15 from the separator can be either recycled or exported from the system. The non-condensable gas stream 16 can be passed through a separation unit 17 to provide a purified $H_2$ stream 19 and a raffinate stream 18 containing carbon dioxide, methane, ethane, propane, and some hydrogen. The purified $H_2$ 19 may then be either exported from the system at 20 or passed through a recycle compressor 21 to provide recycled hydrogen stream 23.

In another preferred reactor system, illustrated in FIG. 7, a first reactor system is provided for converting the desired feedstock solution to $C_{4+}$ compounds. The feedstock solution is stored in tank 1 and then passed through feed line 2 into charge pump 3. Charge pump 3 increases the pressure of the feedstock solution to the desired reaction pressure, e.g., 600 psi, and then discharges the solution through line 4 into an electric preheater 5 that heats the feed to the desired inlet temperature. The heated solution 6 is then passed into the process side of a reactor having essentially a tube-within-tube configuration (tube 7 within tube 8). Depending on the pressure of the reactor and the temperatures at which the several stages are operated, the reactant stream flowing through the reactor tube 7 will generally be maintained substantially in the liquid phase throughout, but may vaporize due to the heat of the condensation of the distal portion 7b such that most of the product exiting the outlet end of the reactor through line 15 is in vapor form.

The stages and stage regions of the reactor tube 7 include an APR/deoxygenation catalyst (combined) and a condensation catalyst, each packed in successive catalytic beds (i.e., one on top of another). In this example, reactor tube 7 contains an APR/deoxygenation catalyst in the proximal portion 7a of reactor tube 7 and a condensation catalyst at the distal portion 7b. The catalyst system is supported at the bottom with small mesh stainless steel spheres setting on a stainless steel frit. Stainless steel spheres are also place on top of the catalyst bed. To facilitate separation of spent catalyst for recycling or regeneration, the catalyst beds are separated by means of a porous material, such as glass wool. The reactor may also be physically separated in separate tubes with conduits connecting the tubes to permit continuous flow. Such an arrangement may permit better thermal management, allowing optimization of temperature according to the requirements of the reactions in the several reactor stages.

The APR reaction is typically endothermic, while the condensation reaction is typically highly exothermic. Preferably, the reactor system permits the heat generated in the condensation reaction to be used to heat the APR and deoxygenation reactions. An advantage of conducting both of these reactions together is that heat is immediately transferred from the exothermic condensation reaction to the endothermic reforming/deoxygenation reactions.

The process tube 7 is preferably formed from a heat-conducting material configured to transfer heat from the distal portion 7b to the proximal portion 7a. In addition, the process tube may be heated with hot oil or hot air flowing through an annular space between process tube 7 and outer tube 8. The hot air may be generated by heating ambient air from a blower 10 with an electrical heater 12 and sent to the reactor through line 13. Hot oil may also be used and generated by a heater and pump (not shown) and sent to the reactor through line 13 as well. The flow configuration for this system is such that the hot air (or oil) in tube 8 flows countercurrent to the process fluid in tube 7. Accordingly, the reactor tube 7 is preferably warmer at the bottom than at the top.

Alternatively, the process tube 7 may be separated into two separate tubes or regions to facilitate the optimization of reaction conditions separately for the APR and deoxygenation reactions, and for the condensation reaction. For example, the separation of spent catalyst for regeneration may be simplified in this manner. In a two-region second stage in a vertical reactor, heat generated by condensation in the lower region may be permitted to move by convection to the upper region for use in the reformation reaction. The second region may also be configured to provide a continuous or step-wise gradient of mixed reformation and condensation catalysts, with more reformation catalyst at the upper end and more condensation catalyst at the lower end.

The effluent 15 from reactor tube 7 includes gaseous products (such as hydrogen, CO and $CO_2$) as well as aqueous and organic liquid products. The effluent is cooled to ambient temperature using a water cooled tube in a tube condenser 16. Effluent 17 from the condenser 16 is then directed to a three-phase separator to separate the product phases: the non-condensable gas 18 (upper phase), a lower density organic-liquid phase 19 (middle phase) and a higher-density aqueous-liquid phase 20 (lower phase). The system pressure is maintained by controlling the flow of non-condensable gas through line 21. The liquid level is maintained by controlling the flow of the aqueous-phase components through line 23. The organic-liquid phase is then skimmed off the top of the aqueous phase through line 22.

The aqueous phase 20 is withdrawn through line 23. If the aqueous phase 20 contains significant levels of residual oxygenates (i.e., products of incomplete reformation), the aqueous phase 20 may be conducted through line 23 back to feed source 6 where it is used for feedstock directed back into the reactor. In this way, the carbon content and energy value of the intermediate processes are recovered.

The middle phase 19 contains $C_{5+}$ compounds. Typically, this phase contains hydrocarbons and mono-oxygenates ranging primarily from $C_4$ to $C_{30}$. Lighter fractions, primarily $C_4$-$C_9$, may be separated for gasoline use. The moderate fraction, i.e., $C_{12}$-$C_{24}$, may be separated for use as jet fuel. Heavier fractions, i.e., $C_{12}$-$C_{24}$, may be separated for diesel use. The heaviest fractions may be used as lubricants or cracked to produce additional gasoline and/or diesel fractions. Each of the above may also be used for industrial chemical applications.

The vapor phase 18 contains hydrogen and other APR reaction products, such as carbon monoxide, carbon dioxide, methane, ethane, propane, butane, pentane, and/or hexane gas. Part of this gas is purged from the system to prevent the build-up of light hydrocarbons and $CO_2$ in the system through line 22. The gases may also be used as a fuel source for purposes of providing heat to the reactor system. In terms of scaled-up production, after start-up, the reactor systems could be process controlled, and the reactions would proceed at steady-state equilibrium.

The following examples are included solely to provide a more complete disclosure of the subject invention. Thus, the following examples serve to illuminate the nature of the invention, but do not limit the scope of the invention disclosed and claimed herein in any fashion.

EXAMPLES

Exemplary Reactor Systems

Example 1

FIG. 8 shows a process diagram illustrating one reactor system useful in practicing the present invention. A feedstock tank 1 acts as a reservoir for holding the feedstock solutions. The feedstock solution is delivered from the feedstock tank 1 to feed pump 3 through feed line 2, where it is then passed through discharge line 4 to preheater 5. The preheater 5 may be a heat exchanger heated by an electrical resistance heater, or any other heat exchanger known in the art. The preheated feed is then passed through line 6 and, in some cases, combined with hydrogen 7 before entering reactor 9 through line 8. One illustration of a potential reactor 9 is set forth in FIG. 11 and more fully described in Example 4 below.

The temperature of the walls of reactor 9 is maintained by block heaters, 10a, 10b, 10c, and 10d, in this case, electrical resistance heaters. Upon exiting the reactor 9, reaction products enter the reactor outlet line 11 and are cooled to near ambient temperature in reactor product cooler 12, resulting in a potential three phase product stream. From reactor product cooler 12, the reaction products proceed through line 13 to pressure regulating valve 14, which is used to control the pressure at the reactor outlet if required.

After valve 14, the products enter a phase separator 16 through line 15 where it segregates into three separate phases: (1) non-condensible gas components 17 containing predominately hydrogen, carbon dioxide, methane, ethane, and propane; (2) an organic liquid fraction 18 containing both hydrocarbons and $C_{3-30}$ alcohols, ketones and carboxylic acids; and (3) an aqueous layer 19 containing mostly water and water soluble oxygenated compounds, such as ethanol, isopropanol, acetone, propanol and acetic acid. The non-condensable gas fraction 17 may be routed through the gas product line 20 to pressure reducing valve 21. The pressure of separator 16 is maintained by pressure reducing valve 21. In an alternate mode of operation, the separator 16 may be maintained at a pressure nearly the same as the reactor outlet by opening or eliminating valve 14. In the alternate mode of operation, the reactor outlet pressure is then controlled by action of pressure reducing valve 21. Gas flow rate and composition are measured upon exiting the system through line 22.

The organic liquid fraction 18 exits the separator through line 23 before entering organic draw-off valve 24. The level of organic phase within the separator is controlled by adjustment of valve 24. The flow rate and composition of the organic fraction are determined after the organic fraction exit the system through line 25. The aqueous liquid fraction 19 exits the separator through line 26 before entering separator bottoms draw-off valve 27. The level of aqueous phase within the separator is controlled by adjustment of valve 27.

The flow rate and composition of the aqueous fraction may be determined after the aqueous fraction exits the system through line 28. In an alternate mode of operation, both the organic liquid fraction 18 and the aqueous liquid fraction 19 exit the system through the bottom draw-off valve 27 of the separator and line 28 before being separated in a decanter for measurement of the individual phase compositions and flow rates.

In all cases, the alternate modes of operation do not affect the catalytic processes being investigated. The alternate modes of operation may be employed as deemed prudent to achieve optimal control of the process, depending on the relative flow rates of the gaseous phase 17, organic liquid phase 18, and aqueous phase 19.

Prior to initiating a flow of feed to the reactors, unless otherwise noted, catalysts were reduced in a stream of flowing hydrogen at 400° C., regardless of whether a reduction was completed prior to loading the catalyst into the reactors.

Example 2

FIG. 9 shows a process diagram illustrating another reactor system useful for practicing the present invention. This reactor configuration contains two separate reactors with the capability of operating both reactors in series or operating only the first reactor. In addition, this configuration allows the catalyst in the second reactor to be taken off line and regenerated in situ. After regeneration, the second reactor may be returned to service without impacting the first reactor operation.

The reactor is similar to the reactor of Example 1, except that the reaction products from reactor product cooler 12 could be routed into the second reactor through line 14 or routed to bypass the second reactor by passing into line 44. When utilizing the second reactor, flow would proceed from line 14 to pressure regulating valve 15. Pressure regulating valve 15 may be used to control the pressure at the outlet of the first reactor. From pressure regulating valve 15 the flow proceeds to the second reactor inlet isolation valve 17 and into line 18. From line 18 the flow continues to line 19 and into the second reactor preheater 20. In the illustrated embodiment, preheater 20 is a heat exchanger heated by an electrical resistance heater.

The preheated feed is then passed through line 19 into the second reactor 22, which is more fully described in Example 4. The temperature of the wall of reactor 22 is maintained by block heaters, 23a, 23b, 23c, and 23d, in this case, electrical resistance heaters. Upon exiting the reactor, the reaction products enter the second reactor outlet line 24 and are then cooled in second reactor product cooler 25. From second reactor product cooler 26 the process flow may be routed through lines 26 and 27 to second reactor outlet isolation valve 28, into lines 29 followed by 30 and then into the product separator 31.

When operation of the second reactor is desired, valve 17 and valve 28 are open while the second reactor bypass valve 45 is closed to prevent the flow from bypassing the second reactor. When operation of only the first reactor is desired, or when the second reactor is being regenerated, valve 17 and valve 28 are closed while valve 45 is open. When the second reactor is bypassed, the first reactor product flows directly from line 13 into line 44, through bypass valve 45, into line 46 and on to line 30. In either case, whether the second reactor is in operation or bypassed, the flow would proceed from line 30 into the product separator.

In phase separator 31, reaction products are separated into a gaseous fraction 32, an organic fraction 33, and an aqueous fraction 34 as described above in Example 1. The gaseous fraction 32 is routed through the gas product line 35 to pressure reducing valve 36. The pressure of separator 31 is maintained by pressure reducing valve 36. When the second reactor 22 is in service, the pressure at the second reactor 22 outlet is controlled by action of pressure reducing valve 36. When the second reactor 22 is bypassed, the pressure at the outlet of the first reactor 9 is controlled by action of pressure reducing valve 36.

Gas flow rate and composition are measured upon exiting the system through line 37. The organic liquid fraction 33 exits the separator through line 38 before entering organic draw-off valve 39. The level of organic phase within the separator is controlled by adjustment of valve 39. The flow rate and composition of the organic fraction are determined after the organic fraction exits the system through line 40. The aqueous liquid fraction 34 exits the separator through line 41 before entering separator bottoms draw-off valve 42. The level of aqueous phase within the separator is controlled by adjustment of valve 42. The flow rate and composition of the aqueous fraction are determined after the aqueous fraction exits the system through line 43. In an alternate mode of operation, both the organic liquid fraction 33 and the aqueous liquid fraction 34 exit the system through the separator bottoms draw-off valve 42 and line 43 before being separated in a decanter for measurement of the individual phase compositions and flow rates. In all cases, the alternate modes of operation do not affect the catalytic processes being investigated. The alternate modes of operation are employed as deemed prudent to achieve optimal control of the process, depending on the relative flow rates of the gaseous phase 35, organic liquid phase 33, and aqueous phase 34.

Example 3

FIG. 10 shows a process diagram illustrating a dual feed pump reactor system useful for practicing the present invention. A dual feed pump system is used when the desired mix of feed components would not exist in a single liquid phase. For example, when a mix of 50% by weight 2-pentanol and 50% by weight water is the desired feed, two feed pumps are used, one to deliver 2-pentanol and the other to deliver water. A similar system may also be used to mix feedstock derived from two separate sources, such as a virgin feedstock and an oxygenated hydrocarbon feedstock derived from an effluent stream of the reactor system itself.

First feedstock tank 1 acts as a reservoir for a first feedstock solution, while second feedstock tank 40 acts as a reservoir for a second feedstock solution. A first feed is delivered from first feedstock tank 1 to first feed pump 3 through first feed line 2. The first feed is then passed through the first feed pump discharge line 4 to combined feed line 44. The second feed is delivered from the second feedstock tank 40 to second feed pump 42 through second feed line 41. The second feed is then passed through second feed pump discharge line 43 to combined feed line 44. From combined feed line 44 the combined feed passes into preheater 5. All other elements are as set forth in Example 1, except that the aqueous phase 19 may be recycled to feedstock tank 40 for further processing or used in other processes.

Example 4

FIG. 11 shows a schematic illustration of one type of reactor which may be employed in reactor systems as described in Examples 1, 2 and 3. Reactor tube 1 is composed of 316 stainless steel with either an inside diameter of 8.5 mms or an inside diameter of 21.2 mm, depending on the experiment. Inlet line 2 is provided to allow feedstock or intermediate product, such as oxygenates, to enter the reactor. Outlet line 3 is provided to remove product from the reactor. Inlet frit 4, composed of stainless steel, acts to secure the beds of preheat media and catalyst in place. Preheat media 5, consisting of stainless steel beads, acts as a zone to allow transfer of heat from the reactor walls so that the feed is at the desired temperature upon entering the catalyst 7. A stainless steel screen may be placed between preheat media 5 and catalyst 7 to prevent the materials from mixing. Catalyst 7 may be supported in position by a second stainless steel frit 8.

A thermowell 9 may be installed in some cases to allow measurement of the temperatures within catalyst 7 and preheating zone 5. Control of temperature at the reactor inlet is accomplished by the use of an external preheater prior to the feed entering the reactor through line 2, and may be further adjusted by control of the heat transfer that occurs in the preheat media. In some cases, the preheat media is not required to achieve the desired temperature profile. Control of the reactor wall temperature is achieved by the use of external heaters in contact with the outer wall of the reactor. Independently controlled heating zones may be used to control the temperature of the reactor wall as desired.

Example 5

Analysis Techniques

Product streams from the examples described below were analyzed as follows. The organic liquid phase was collected and analyzed using either gas chromatograph with mass spectrometry detection or flame ionization detection. Component separation was achieved using a column with a bonded 100% dimethyl polysiloxane stationary phase. Relative concentrations of individual components were estimated via peak integration and dividing by the sum of the peak areas for an entire chromatogram. Compounds were identified by comparison to standard retention times and/or comparison of mass spectra to a compiled mass spectral database. Gas phase compositions were determined by gas chromatography with a thermal conductivity detector and flame ionization or mass spectrometry detectors for other gas phase components. The aqueous fraction was analyzed by gas chromatography with and without a derivatization of the organic components of the fraction using a flame ionization detector. Product yields are represented by the feed carbon present in each product fraction. The weight hourly space velocity (WHSV) was defined as the weight of feed introduced into the system per weight of catalyst per hour, and based on the weight of the oxygenated hydrocarbon feed only, excluding water present in the feed.

Production of Oxygenates

Example 6

Hydrogenation Catalyst

A hydrogenation catalyst was prepared by adding an aqueous solution of dissolved ruthenium nitrosyl nitrate to a carbon catalyst support (UU Carbon, Calgon, with particle sizes restricted to those that were maintained on a 120 mesh screen after passing through an 60 mesh screen) to a target loading of 2.5% ruthenium. Water was added in excess of the pore volume and evaporated off under vacuum until the catalyst was free flowing. The catalyst was then dried overnight at 100° C. in a vacuum oven.

Example 7

APR/Deoxygenation Catalyst

A combined APR and deoxygenation catalyst was prepared by dissolving hexachloroplatinic acid and perrhenic acid in water and then adding the mixture to a monoclinic zirconia catalyst support (N or Pro Saint-Gobain, Product code SZ31164, with particle sizes restricted to those that were maintained on a 60 mesh screen after passing through an 18 mesh screen) using an incipient wetness technique to target a platinum loading of 1.8% and a rhenium loading of 6.3% on the catalyst after subsequent decomposition of the metal precursors. The preparation was dried overnight in a vacuum oven and subsequently calcined in a stream of flowing air at 400° C.

Example 8

Conversion of Sucrose to Oxygenates

The catalyst systems referenced in Examples 6 and 7 were investigated for the conversion of sucrose to an intermediate product containing oxygenates using the reactor system described in Example 1. The study was conducted using a 21.2 mm internal diameter stainless steel tube reactor shown in Example 4, with an analysis completed as described in Example 5.

31 grams of hydrogenation catalyst from Example 6 and 76 grams of APR catalyst from Example 7 were loaded into the reactor, with the hydrogenation catalyst on top of the APR catalyst, separated by a stainless steel screen. External hydrogen was combined with the feed prior to the feed entering the reactor. Heaters external to the reactor, shown in FIG. 8 as 10a, 10b, 10c, 10d, were maintained at the following reactor wall temperatures; 10a—125° C., 10b—200° C., 10c—265° C., 10d—265° C., resulting in reactor bed temperatures of approximately ~110-150° C. for hydrogenation, and 150-265° C. for the APR/Deoxygenation catalyst. The ranges indicate the approximate reactor wall temperatures at the inlet and outlet of each catalyst bed, respectively. Results from the experiment across 39 hours of operation are shown in Table 1. The WHSV is based on the weight of the APR/Deoxygenation catalyst. Total mono-oxygenates includes alcohols, ketones, tetrahydrofurans and cyclic mono-oxygenates. Cyclic mono-oxygenates includes compounds in which the ring does not include oxygen, such as cyclopentanone and cyclohexanone. The fraction of feed carbon contained within unknown components in the aqueous phase was determined as the difference of carbon accounted for by known, measured components and the total organic carbon.

TABLE 1

Conversion of Sucrose to Oxygenates Across a Hydrogenation and APR catalyst

| Hours on Stream | | 5 | 16 | 27 | 39 |
|---|---|---|---|---|---|
| WHSV | $wt_{feed}/(wt_{catalyst}\ hr)$ | 1.8 | 1.8 | 1.7 | 1.5 |
| Added Hydrogen | $mol_{H2}/mol_{feed}$ | 3.4 | 3.4 | 3.6 | 4.0 |
| Organic Phase Yield | % of feed carbon | 27 | 25 | 20 | 22 |
| Breakdown of Reactor Outlet Composition | | | | | |
| Carbon Dioxide | % of feed carbon | 19.4 | 21.2 | 18.1 | 17.7 |
| Paraffins | % of feed carbon | 14.1 | 13.5 | 9.2 | 10.8 |
| Mono-oxygenates | % of feed carbon | 31.5 | 30.6 | 27.5 | 30.8 |
| Alcohols | % of feed carbon | 11.1 | 11.8 | 11.2 | 11.6 |
| Ketones | % of feed carbon | 8.2 | 7.0 | 7.1 | 9.0 |

TABLE 1-continued

Conversion of Sucrose to Oxygenates Across a Hydrogenation and APR catalyst

| Hours on Stream | | 5 | 16 | 27 | 39 |
|---|---|---|---|---|---|
| Tetrahydrofurans | % of feed carbon | 10.6 | 10.7 | 8.1 | 8.6 |
| Cyclic Mono-oxygenates | % of feed carbon | 1.6 | 1.1 | 1.1 | 1.5 |
| Unknown Aqueous Species | % of feed carbon | 21.2 | 27.8 | 28.3 | 32.0 |

Example 9

APR/Deoxygenation Catalyst

A catalyst was prepared as described in Example 7, except that the catalyst support was a tetragonal zirconia (N or Pro Saint-Gobain, Product code SZ61152) with particle sizes restricted to those that were maintained on a 60 mesh screen after passing through an 18 mesh screen.

Example 10

APR/Deoxygenation Catalyst

Hexachloroplatinic acid and perrhenic acid dissolved in water were added to a monoclinic zirconia catalyst support (N or Pro Saint-Gobain, Product code SZ61164, with particle sizes restricted to those that were maintained on a 60 mesh screen after passing through an 18 mesh screen) using an incipient wetness technique to target a platinum loading of 1.9% and a rhenium loading of 1.8% on the catalyst after subsequent decomposition of the metal precursors. The preparation was dried overnight in a vacuum oven and subsequently calcined in a stream of flowing air at 400° C.

Example 11

APR/Deoxygenation Catalyst

A catalyst was prepared as described in Example 7 except that the support was a hydrogen peroxide functionalized activated carbon. The support was first prepared by adding activated carbon (Calgon UU 60×120 mesh carbon) slowly to a 30% hydrogen peroxide solution, with the mixture then left overnight. The aqueous phase was decanted and the carbon was washed three times with deionized water, and then dried under vacuum at 100° C. A solution of hexachloroplatinic acid and perrhenic acid in water was then added to the support using an incipient wetness technique to target a platinum loading of 1.8% and a rhenium loading of 6.3% after subsequent decomposition of the metal precursors. The preparation was dried overnight in a vacuum oven at 100° C.

Example 12

Conversion of Sorbitol and Glycerol

The catalyst systems referenced in Example 9, Example 10, and Example 11, were investigated for the conversion of sorbitol or glycerol to an intermediate product containing oxygenates using the reactor configuration described in Example 1, with an analysis completed as described in Example 5. The study was conducted using the 8.5 mm internal diameter stainless steel tube reactor shown in Example 4. In all cases, the reactor pressure was maintained at 625 psig. Reactor inlet and outlet temperatures, shown in Table 2 were controlled using heaters external to the reactor as shown in FIG. 8 as 10a, 10b, 10c, 10d. Results of these experiments are shown in Table 2.

Table 2 shows the impact of catalyst composition, feedstock composition, and operating conditions on the conversion performance. FIG. 12 shows the carbon number distribution of the mono-oxygenates produced in Experiment D and Experiment E. The primary difference between these two experiments was the reaction temperature. For Experiment D, mono-oxygenates containing three or fewer carbon atoms predominated while for Experiment E, a significant fraction of the mono-oxygenates contained four or more carbon atoms, indicating that condensation reactions were occurring within the same reaction zone as the hydrogen generation and deoxygenation reactions. The WHSV is based on the weight of the APR/Deoxygenation catalyst. The net hydrogen produced is the hydrogen present at the reactor outlet as $H_2$, which does not include hydrogen produced and consumed in situ. Total mono-oxygenates include alcohols, ketones, tetrahydrofurans and cyclic mono-oxygenates. Cyclic mono-oxygenates include compounds in which the ring does not include oxygen, such as cyclopentanone and cyclohexanone. The fraction of feed carbon contained within unknown components in the aqueous phase was determined as the difference of carbon accounted for by known, measured components and the total organic carbon.

TABLE 2

Conversion of Polyols to Oxygenates Across a APR/Deoxygenation Catalyst

| | | Experiment | | | | |
|---|---|---|---|---|---|---|
| | | A | B | C | D | E |
| | | Feed | | | | |
| Catalyst Composition | Example No. | 50% Sorbitol 11 | 50% Sorbitol 9 | 65% Sorbitol 10 | 50% Glycerol 10 | 50% Glycerol 10 |
| WHSV | $wt_{feed}/(wt_{catalyst}$ hr) | 2.1 | 1.8 | 1.7 | 1.5 | 1.5 |
| Catalyst Inlet Temp. | ° C. | 241 | 240 | 240 | 260 | 310 |
| Catalyst Outlet Temperature | ° C. | 240 | 241 | 321 | 260 | 350 |
| Net Hydrogen Produced | $mol_{H2}/mol_{feed}$ | 0.6 | 0.9 | 0.7 | 1.2 | 0.7 |
| Organic Phase Yield | % of feed carbon | 17 | 24 | 38 | 0 | 38 |

TABLE 2-continued

Conversion of Polyols to Oxygenates Across a APR/Deoxygenation Catalyst

| Catalyst Composition | Example No. | Experiment | | | | |
|---|---|---|---|---|---|---|
| | | A | B | C | D | E |
| | | Feed | | | | |
| | | 50% Sorbitol 11 | 50% Sorbitol 9 | 65% Sorbitol 10 | 50% Glycerol 10 | 50% Glycerol 10 |
| Breakdown of Reactor Outlet Composition | | | | | | |
| Carbon Dioxide | % of feed carbon | 32.4 | 34.0 | 23.5 | 31.3 | 16.0 |
| Paraffins | % of feed carbon | 37.4 | 25.3 | 7.8 | 6.6 | 7.4 |
| Total Mono-oxygenates | % of feed carbon | 33.9 | 32.9 | 40.0 | 45.9 | 41.0 |
| Alcohols | % of feed carbon | 6.3 | 8.5 | 2.6 | 40.6 | 4.6 |
| Ketones | % of feed carbon | 23.5 | 16.9 | 15.2 | 5.2 | 24.1 |
| Tetrahydrofurans | % of feed carbon | 4.1 | 7.2 | 10.7 | 0.1 | 2.7 |
| Cyclic Monooxygenates | % of feed carbon | 0.0 | 0.4 | 11.6 | 0.0 | 9.7 |
| Unknown Aqueous Species | % of feed carbon | 1.2 | 7.8 | 15.8 | 30.4 | 10.7 |

Condensation of Oxygenates Using Basic Catalysts

Example 13

A zinc aluminate catalyst support was prepared by mixing zinc oxide powder and alumina powder (Dispal 18N4-80, Sasol North America, Houston, Tex.) to a target ratio of 1.0 moles of ZnO to 1 mole of $Al_2O_3$. Dilute nitric acid was then added at a level of 1 wt % $HNO_3$ to alumina. The dough consistency of the mixture was adjusted with water addition to form a workable dough, which was then extruded using a laboratory scale extruder. The extrudates were dried overnight under vacuum at 100° C., then further dried at 200° C. for one hour under flowing air, and then subsequently calcined at 750° C. for 4 hours under flowing air. The resulting material was then ground and sieved. Material that was maintained on a 60 mesh screen after passing through an 18 mesh screen was recovered.

Example 14

Hexachloroplatinic acid was added to the calcined material of Example 13 using an incipient wetness impregnation technique to achieve a target platinum loading of 1.0 wt %. The catalyst was dried overnight under vacuum at 100° C. and calcined at 400° C. under flowing air.

Example 15

Palladium nitrate was added to the calcined material of Example 13 using an incipient wetness impregnation technique to achieve a target palladium loading of 0.5 wt %. The catalyst was dried overnight under vacuum at 100° C. and calcined at 400° C. under flowing air.

Example 16

A copper zinc aluminate catalyst was prepared by mixing zinc oxide, copper (I) oxide, and alumina powder (Dispal 18N4-80) at a target ratio of 0.11 moles of CuO and 0.9 moles of ZnO to one mole of $Al_2O_3$. Dilute nitric acid was then added at a level of 1 wt % $HNO_3$ to alumina. The dough consistency of the mixture was adjusted with water addition to form a workable dough, which was then extruded using a laboratory scale extruder. The extrudates were dried overnight under vacuum at 100° C., then further dried at 200° C. for one hour under flowing air, and then subsequently calcined at 750° C. for 4 hours under flowing air. The resulting material was then ground and sieved. Material that was maintained on a 60 mesh screen after passing through an 18 mesh screen was recovered.

Example 17

A cesium modified silica-alumina catalyst was prepared by adding cesium carbonate dissolved in water to Siralox silica-alumina catalyst support (Sasol North America, Houston, Tex.). The target loading of cesium was 25 wt % based on final catalyst weight. This material was dried for 24 hours under vacuum at 100° C. and calcined at 500° C. for 6 hours under flowing air. After calcining, platinum was added using an incipient wetness impregnation technique to achieve a final platinum loading of 1 wt %. After impregnation, the catalyst was dried and then calcined at 500° C. for 6 hours under flowing air.

Example 18

A cerium modified silica was prepared by adding cerium nitrate solution to a silica gel (Davisil grade 636, WR Grace Company) to a final loading of 25 wt % $CeO_2$. The resulting material was then dried at 120° C. for six hours and further calcined at 550° C. for six hours under flowing air. Palladium nitrate was added to the calcined material using an incipient wetness impregnation technique to achieve a target palladium loading of 0.5 wt %. This material was then dried at 120° C. for six hours and further calcined at 550° C. for six hours under flowing air.

Example 19

The catalyst systems referenced in Examples 14-18 were investigated for the vapor-phase condensation of various oxygenates. The studies were conducted using 8.5 mm and 21.2 mm internal diameter size stainless steel tube reactors as described in Example 4 and in the reactor systems illustrated by FIGS. 8 and 10. Between 15 and 18 milliliters of catalyst was loaded into the smaller reactor, with between 50 and 70 milliliters of catalyst loaded into the larger reactor. In all cases the catalyst was reduced at 400° C. under flowing hydrogen prior to use.

The organic liquid phase was collected and analyzed as described in Example 5. Table 3 shows organic product yields and composition as a function of operating conditions, feedstock composition, and the added metal component for the catalysts described in Examples 14-18 above. Greater than 100% reported organic phase yields stem from experimental uncertainty in the measurement of process stream flow rates or composition. Non-condensed components are those components that do not require the formation of new carbon-carbon bonds to be produced from the given feed. For simplicity, all compounds containing five or fewer carbon atoms are considered to be non-condensed components. Total condensation products are those compounds containing six or more carbon atoms, which require the formation of new carbon-carbon bonds to be formed from the given feedstocks.

Experiments F and G demonstrate that product selectivity can be affected by the choice of hydrogenation function, e.g. Pt or Pd. Paraffins were produced to a larger extent over the catalyst containing 1% platinum compared to the catalyst containing 0.5% palladium. The later favored the production of mono-oxygenates, primarily ketones. Experiments H and I further reinforce this concept. Experiment H shows that condensed mono-oxygenate components can be obtained at high yield with isopropyl alcohol as a feed, accounting for >97% of the organic product and containing >90% of the overall carbon at the reactor outlet. By increasing the reaction temperature and using copper to drive the hydrogenation reactions, the selectivity can be shifted to obtain a significant yield of olefins (Experiment I). Experiments J, K and L show that a number of other heterogeneous catalysts can be used to promote the condensation of oxygenates followed by hydrogenation of the initial condensation products. Experiments K and L show that as the temperature is decreased from 300° C. to 250° C., the rate of condensation drops so that the conversion to condensed products drops from 81 wt % to 18 wt % in the resulting organic phase.

TABLE 3

Vapor Phase Condensation of Oxygenates Over Basic Catalysts

| | | Catalyst | | | | | | |
|---|---|---|---|---|---|---|---|---|
| | | 1% Pt/ ZnO/Al2O3 | 0.5% Pd/ ZnO/Al2O3 | 0.5% Pd/ ZnO/Al2O3 | CuO/ZnO/Al2O3 | 1% Pt/Cs Impregnated Siralox Silica-Alumina | 0.5% Pd/ Ce Modified Silica | 0.5% Pd/ Ce Modified Silica |
| | | | | | Experiment | | | |
| | | F | G | H | I | J | K | L |
| Feed | | 49.5% 2-Pentanone, 50.5% 2-Pentanol | 49.5% 2-Pentanone, 50.5% 2-Pentanol | 100% Isopropyl Alcohol | 100% Isopropyl Alcohol | 49.5% 2-Pentanone, 50.5% 2-Pentanol | 100% Isopropyl Alcohol | 100% Isopropyl Alcohol |
| WHSV | $wt_{feed}/(wt_{catalyst}$ hr) | 1 | 1.5 | 1.5 | 2 | 1.1 | 1.9 | 1.9 |
| Added Hydrogen | $mol_{H2}/mol_{feed}$ | 1 | 1 | 0 | 0 | 1 | 0 | 0 |
| Temperature | ° C. | 375 | 375 | 300 | 375 | 325 | 300 | 250 |
| Pressure | Psig | 600 | 600 | 600 | 625 | 600 | 600 | 600 |
| Organic Phase Yield | % of feed carbon | 75 | 99 | 95 | 55 | 107 | 74 | 98 |
| Organic Phase Composition Breakdown | | | | | | | | |
| C5− Hydrocarbons | wt % | 9.6 | 7.3 | 0.0 | 2.4 | 1.6 | 0.0 | 0.0 |
| C5− Oxygenates | wt % | 6.2 | 20.9 | 1.9 | 14.6 | 75.8 | 18.5 | 81.8 |
| Total Non-Condensed Components | wt % | 15.8 | 28.2 | 1.9 | 16.9 | 77.4 | 18.5 | 81.8 |
| C6+ Paraffins | wt % | 49.5 | 18.9 | 0.3 | 1.0 | 0.0 | 20.1 | 0.2 |
| C6+ Olefins | wt % | 4.6 | 0.0 | 0.0 | 15.9 | 0.0 | 0.0 | 0.0 |
| Other C6+ Hydrocarbons | wt % | 0.0 | 0.0 | 0.0 | 1.1 | 0.0 | 0.0 | 0.0 |
| C6+ Monooxygenates | wt % | 30.2 | 51.8 | 97.3 | 64.5 | 22.6 | 61.0 | 18.0 |
| Total Cond. Products | wt % | 84.2 | 70.7 | 97.6 | 82.5 | 22.6 | 81.1 | 18.2 |

Condensation of Oxygenates Using Acid-Base Catalysts

Example 20

A hydrotalcite catalyst was prepared from a commercially available hydrotalcite support (ESM-350, ASM Catalysts, Baton Rouge, La.) by grinding the material and passing through graduated screens to achieve particles sizes larger than 60 mesh and less than 18 mesh. The material was then calcined in a quartz tube reactor at 450° C. for 6 hours under flowing nitrogen.

Example 21

Platinum was added to the hydrotalcite catalyst of Example 20 using an incipient wetness impregnation technique to achieve a final target platinum loading of 1 wt %. The platinum containing precursor was hexachloroplatinic acid, $H_2PtCl_6$. The impregnated material was dried overnight under vacuum at 100° C. and subsequently calcined at 400° C. for 2 hours under flowing air.

Example 22

Platinum and tin were added to the hydrotalcite catalyst of Example 20 using an incipient wetness impregnation technique to achieve a final target loading of 1 wt % Pt and 0.2 wt % Sn. The platinum containing precursor was hexachloroplatinic acid, $H_2PtCl_6$ while tin was derived from tin chloride, $SnCl_2*2H_2O$. The impregnated material was dried overnight under vacuum at 100° C. and subsequently calcined at 450° C. for 8 hours under flowing nitrogen.

Example 23

A 5% magnesium oxide catalyst supported on granular zirconia was prepared using an incipient wetness impregnation technique to achieve a final target loading of 5 wt % Mg. Magnesium was added as magnesium nitrate and dried overnight under vacuum at 100° C. and subsequently calcined at 450° C. for 8 hours under flowing air. An aqueous palladium nitrate solution was added to the calcined material to achieve a target palladium loading of 0.5 wt % using an incipient wetness impregnation technique. The catalyst was dried a second time and calcined at 400° C. for six hours under flowing air.

Example 24

A zinc aluminate catalyst support was prepared by mixing zinc oxide powder and alumina powder (Dispal 18N4-80, Sasol North America, Houston, Tex.) to a target ratio of 0.85 moles of ZnO to 1 mole of $Al_2O_3$. Dilute nitric acid was added at a level of 1 wt % $HNO_3$ to total solids. The dough consistency was adjusted with water addition to form a workable dough suitable for extrusion and the mixture was extruded using a laboratory scale extruder. The extrudates were dried overnight under vacuum at 100° C. and subsequently calcined at 750° C. for 8 hours under flowing air. The material was then sized to 18 by 60 mesh. An aqueous palladium nitrate solution was added to the calcined material to achieve a target palladium loading of 0.5 wt % using an incipient wetness impregnation technique. This catalyst was then dried a second time and calcined at 400° C. for six hours under flowing air.

Example 25

The catalyst systems referenced in Examples 21-24 were used to conduct vapor-phase condensation reactions with various oxygenates. The studies were conducted using 8.5 mm and 21.2 mm internal diameter size stainless steel tube reactors as described in Example 4 and reactor systems as illustrated in Examples 1 and 3. Between 15 and 18 milliliters of catalyst was loaded into the smaller reactor, with between 50 and 70 milliliters of catalyst loaded into the larger reactor. In all cases the catalyst was reduced at 400° C. under flowing hydrogen prior to use.

The organic liquid phase was collected and analyzed as described in Example 5. Table 4 shows the organic product yields and composition as a function of operating conditions, feedstock composition, and the added metal component for the hydrotalcite catalysts described in Examples 21 and 22 above. The data from the experiments show that a primarily hydrocarbon product can be formed from acetone and isopropyl alcohol in the absence of an added metal hydrogenation component. In Experiment M, the organic phase product contained primarily nine carbon methyl substituted cyclohexenes, categorized as other $C_6+$ hydrocarbons in Table 4. The addition of platinum (Experiment N) to this catalyst favored the formation of condensed mono-oxygenate products, mainly ketones and alcohols, and the formation of some paraffins as a result of deoxygenation of the ketones and alcohols. The selectivity was further shifted in favor of condensed mono-oxygenates by attenuating the platinum with tin and operating at a higher pressure (Experiment O). Experiments P, Q, R and S illustrate the impact of reaction temperature for the condensation of a mixed feed containing pentanol and pentanone. As the reaction temperature was raised from 300° C. to 375° C., a gradual change in product composition became apparent, with the selectivity to condensed mono-oxygenates decreasing and the selectivity to condensed paraffins increasing as the temperature was raised.

Table 5 shows the impact of feedstock components and reaction temperature on organic product yields and composition for the catalysts of Examples 23 and 24. Experiments T and U compare the condensation of 2-pentanone and 2-methyltetrahydrofuran. Overall, the condensation of 2-pentanone is faster than 2-methyltetrahydrofuran. Nonetheless, around 30% of the tetrahydrofuran was converted to condensation products under these conditions. Experiments 10 and 11 show the impact of reaction temperature when using a pure isopropyl alcohol feed. At 300° C. (Experiment V), mono-oxygenated condensation products predominate, while at 400° C. (Experiment W) a significant portion of the products consisted of hydrocarbons. Compared to other experiments listed in Tables 4 and 5, Experiment W is notable in that the organic product contained a higher level of olefins. The addition of valeric acid to the feed (Experiment X) suppressed overall condensation rates and shifted the selectivity away from paraffins and towards other hydrocarbons, primarily substituted aryl compounds.

Greater than 100% reported organic phase yields stem from experimental uncertainty in the measurement of process stream flow rates or composition. Non-condensed components are those components that do not require the formation of new carbon-carbon bonds to be produced from the given feed. For simplicity, all compounds containing five or fewer carbon atoms are considered to be non-condensed components. Total condensation products are those compounds containing six or more carbon atoms, which require the formation of new carbon-carbon bonds to be formed from the given feedstocks.

TABLE 4

Vapor Phase Condensation of Oxygenates Over Hydrotalcite Catalysts

| | | Metal Function | | | | | | |
|---|---|---|---|---|---|---|---|---|
| | | None | 1% Pt | 1% Pt, 0.2% Sn | 1% Pt, 0.2% Sn | 1% Pt, 0.2% Sn | 1% Pt, 0.2% Sn | 1% Pt, 0.2% Sn |
| | | | | | Experiment | | | |
| | | M | N | O | P | Q | R | S |
| Feed | | 50% Isopropyl Alcohol, 50% Acetone | 50% Isopropyl Alcohol, 50% Acetone | 50% Isopropyl Alcohol, 50% Acetone | 49.5% 2-Pentanone, 50.5% 2-Pentanol | 49.5% 2-Pentanone, 50.5% 2-Pentanol | 49.5% 2-Pentanone, 50.5% 2-Pentanol | 49.5% 2-Pentanone, 50.5% 2-Pentanol |
| WHSV | $wt_{feed}/Wt_{catalyst}$ hr | 1.0 | 0.9 | 0.7 | 0.7 | 0.7 | 0.7 | 0.7 |
| Added Hydrogen | $mol_{H2}/mol_{feed}$ | 0.5 | 0 | 0 | 1 | 1 | 1 | 1 |
| Temperature | °C. | 350 | 350 | 350 | 300 | 325 | 350 | 375 |
| Pressure | Psig | 100 | 100 | 600 | 600 | 600 | 600 | 600 |
| Organic Phase Yield | % of feed carbon | 61 | 95 | 91 | 108 | 104 | 108 | 85 |
| Organic Phase Composition Breakdown | | | | | | | | |
| C5- Hydrocarbons | wt % | 2.8 | 3.6 | 1.0 | 4.6 | 7.1 | 9.4 | 20.0 |
| C5- Oxygenates | wt % | 11.9 | 16.0 | 5.8 | 41.9 | 21.4 | 13.7 | 8.8 |
| Total Non-Condensed Components | wt % | 14.7 | 19.6 | 6.8 | 46.5 | 28.5 | 23.1 | 28.8 |
| C6+ Paraffins | wt % | 0.0 | 13.1 | 7.6 | 2.2 | 11.3 | 28.6 | 53.0 |
| C6+ Olefins | wt % | 5.1 | 1.2 | 1.0 | 0.0 | 0.2 | 0.0 | 0.0 |
| Other C6+ Hydrocarbons | wt % | 72.8 | 0.0 | 0.0 | 0.0 | 0.0 | 0.0 | 0.0 |
| C6+ Monooxygenates | wt % | 5.7 | 54.3 | 80.4 | 51.4 | 60.1 | 47.8 | 18.2 |
| Total Condensation Products | wt % | 83.5 | 68.6 | 89.0 | 53.6 | 71.6 | 76.5 | 71.2 |

TABLE 5

Vapor Phase Condensation of Oxygenates Over Magnesium Impregnated Zirconia and Zinc Aluminate Catalysts

| | | Catalyst | | | | |
|---|---|---|---|---|---|---|
| | | 0.5% Pd/5% Mg Zirconia | 0.5% Pd/5% Mg Zirconia | 0.5% Pd/Zinc Aluminate (0.85:1 ZnO:Al$_2$O$_3$) | 0.5% Pd/Zinc Aluminate (0.85:1 ZnO:Al$_2$O$_3$) | 0.5% Pd/Zinc Aluminate (0.85:1 ZnO:Al$_2$O$_3$) |
| | | | | Experiment | | |
| | | T | U | V | W | X |
| Feed | | 100% 2-pentanone | 100% 2-methyltetrahydrofuran | 100% Isopropyl alcohol | 100% Isopropyl alcohol | 90% Isopropyl alcohol, 10% Valeric Acid |
| WHSV | $wt_{feed}/(wt_{catalyst}$ hr) | 2 | 2 | 1 | 1 | 1 |
| Added Hydrogen | $mol_{H2}/mol_{feed}$ | 1 | 1 | 0 | 0 | 0 |
| Temperature | °C. | 400 | 400 | 300 | 400 | 400 |
| Pressure | psig | 600 | 625 | 600 | 600 | 600 |
| Organic Phase Yield | % of feed carbon | 85 | 76 | 104 | 58 | 53 |
| Organic Phase Composition Breakdown | | | | | | |
| C5- Hydrocarbons | wt % | 7.4 | 4.0 | 0.4 | 2.8 | 2.0 |
| C5- Oxygenates | wt % | 21.4 | 66.5 | 5.2 | 6.9 | 17.3 |
| Total Non-Condensed Components | wt % | 28.8 | 70.6 | 5.6 | 9.7 | 19.3 |
| C6+ Paraffins | wt % | 22.1 | 10.9 | 3.4 | 17.1 | 5.6 |
| C6+ Olefins | wt % | 0.0 | 2.8 | 0.0 | 23.8 | 13.6 |

TABLE 5-continued

Vapor Phase Condensation of Oxygenates Over Magnesium Impregnated Zirconia and Zinc Aluminate Catalysts

|  |  | Catalyst | | | | |
| --- | --- | --- | --- | --- | --- | --- |
|  |  | 0.5% Pd/5% Mg Zirconia | 0.5% Pd/5% Mg Zirconia | 0.5% Pd/Zinc Aluminate (0.85:1 ZnO:Al$_2$O$_3$) | 0.5% Pd/ Zinc Aluminate (0.85:1 ZnO:Al$_2$O$_3$) | 0.5% Pd/ Zinc Aluminate (0.85:1 ZnO:Al$_2$O$_3$) |
|  |  | | | Experiment | | |
|  |  | T | U | V | W | X |
| Other C6+ Hydrocarbons | wt % | 1.3 | 0.3 | 0.0 | 8.1 | 19.8 |
| C6+ Monooxygenates | wt % | 46.5 | 14.7 | 90.8 | 41.2 | 38.6 |
| Total Cond. Products | wt % | 69.9 | 28.8 | 94.2 | 90.1 | 77.7 |

Base Condensation of Oxygenates Followed by Deoxygenation

Example 26

A zinc aluminate catalyst support was prepared similar to that in Example 13 except that the amount of zinc oxide was reduced to target a ratio of 0.85 moles of ZnO to 1 mole of Al$_2$O$_3$.

Example 27

Hexachloroplatinic acid was added to the calcined material of Example 26 using an incipient wetness impregnation technique to achieve a target platinum loading of 1.0 wt %. The catalyst was dried overnight under vacuum at 100° C. and calcined at 400° C. under flowing air.

Example 28

The catalyst systems referenced in Examples 27 and 15 were investigated for the vapor-phase condensation of various oxygenates and subsequent conversion to hydrocarbons. The studies were conducted using 21.2 mm internal diameter size stainless steel tube reactors as described in Example 4, and reactor systems as illustrated by Examples 2 and 3. Approximately 100 milliliters of each catalyst was loaded into two separate reactors. The two reactors were arranged so that the effluent of the first reactor flowed into the second reactor. The first reactor contained the catalyst of Example 15 and the second reactor contained the catalyst of Example 27. The catalyst was reduced at 400° C. under flowing hydrogen prior to use. In all cases, hydrogen was combined with the feed prior to entering the reactor.

Products were separated and analyzed as described in Example 5. Table 6 shows organic product yields and composition as a function of operating conditions and feedstock composition obtained from the consecutive reactions. Non-condensed components are those components that do not require the formation of new carbon-carbon bonds to be produced from the given feed. For simplicity, all compounds containing five or fewer carbon atoms are considered to be non-condensed components. Total condensation products are those compounds containing six or more carbon atoms, which require the formation of new carbon-carbon bonds to be formed from the given feedstocks.

Experiments AA, BB, CC, and DD demonstrate that various oxygenates can be employed in the consecutive condensation and deoxygenation reactions to yield a product containing primarily $C_{6+}$ alkanes. The products contain a larger fraction of alkanes and low levels of oxygenated compounds compared to the results shown in Table 3. This demonstrates that the use of catalysts with different functionalities (i.e. a basic+hydrogenation catalyst in a first reactor followed by acid+basic+hydrogenation catalyst in the second reactor) can be more effective for the production of hydrocarbons from oxygenated compounds than the use of a catalyst that contains only basic and hydrogenation functionality. In Experiment EE, the organic product produced in Experiments AA through DD was recycled through the reaction system. After this treatment, the final product contained primarily alkanes with only traces of oxygen containing components. The hydrocarbons thus produced would be valuable for use as liquid fuels such as gasoline, diesel, and jet fuel.

TABLE 6

Vapor Phase Condensation and Deoxygenation of Oxygenates

|  |  | Experiment | | | | |
| --- | --- | --- | --- | --- | --- | --- |
|  |  | AA | BB | CC | DD | EE |
|  |  | Feed | | | | |
|  |  | 100% Isopropyl Alcohol | 50% Isopropyl Alcohol + 50% 2-Pentanone | 100% 2-Pentanone + | 50% Acetone + 50% 2-Pentanone | Organic Phase From AA-DD |
| WHSV | wt$_{feed}$/(wt$_{catalyst}$ hr) | 1.9 | 2.2 | 2.1 | 2.0 | 2.0 |
| Added Hydrogen | mol$_{H2}$/mol$_{feed}$ | 1.5 | 1.7 | 2 | 2 | >2 |

TABLE 6-continued

Vapor Phase Condensation and Deoxygenation of Oxygenates

| | | Experiment | | | | |
|---|---|---|---|---|---|---|
| | | AA | BB | CC | DD | EE |
| | | | | Feed | | |
| | | 100% Isopropyl Alcohol | 50% Isopropyl Alcohol + 50% 2-Pentanone | 100% 2-Pentanone + | 50% Acetone + 50% 2-Pentanone | Organic Phase From AA-DD |
| Reactor 1 Temperature | ° C. | 300 | 300 | 300 | 300 | 325 |
| Reactor 2 Temperature | ° C. | 350 | 375 | 375 | 375 | 375 |
| Pressure | psig | 625 | 625 | 625 | 625 | 625 |
| Organic Phase Yield | % of feed carbon | 81 | 76 | 80 | 93 | 87 |
| | | Product Composition Breakdown | | | | |
| C5− Hydrocarbons | % of feed carbon | 8 | 11 | 15 | 33 | 15 |
| C5− Oxygenates | % of feed carbon | 3 | 2 | 2 | 4 | 0 |
| Total Non-Condensed Components | % of feed carbon | 11 | 13 | 18 | 37 | 15 |
| C6+ Alkanes | % of feed carbon | 71 | 71 | 65 | 56 | 74 |
| C6+ Alkenes | % of feed carbon | 0 | 0 | 0 | 0 | 0 |
| Other $C_{6+}$ Hydrocarbons | % of feed carbon | 0 | 0 | 0 | 0 | 0 |
| $C_{6+}$ Monooxygenates | % of feed carbon | 6 | 5 | 3 | 2 | 0 |
| Total Products (Condensation) | % of feed carbon | 77 | 76 | 68 | 58 | 74 |

Product Fractionation

Example 29

The material of Experiment EE of Example 28 was collected and subjected to a distillation step. The distillation was conducted at atmospheric pressure using a simple, single stage laboratory batch distillation apparatus. 2.950 liters of liquid product was added to a heated round bottomed flask which acted at the reboiler at the beginning of the experiment. The overhead product was condensed and segregated into separate samples based on the temperature of the vapor phase in equilibrium with the boiling liquid, with an analysis of the fractions completed as described in Example 5. The carbon number distribution of the product fractions is shown in Table 7. All fractions contained primarily alkanes.

The fractions recovered with a boiling point less than 150° C. contain alkanes mainly in the $C_{5-10}$ range and would be suitable as a gasoline blending component. The higher boiling point range materials could be potentially useful for incorporation into distillate fuels, kerosene and diesel.

Example 30

The distilled product boiling in the range of 150° C. to 250° C. was analyzed for suitability as a Jet Fuel by a commercial testing service (Intertek Testing Services, Illinois) according to ASTM testing method D1655. The sample passed all required specifications with the exception of the flash point and density specifications. It is probable that the flash point specification could be met through adoption of improved product distillation, while the low density may be attributed to the high levels of alkanes in the sample.

TABLE 7

Results from Distillation of the Product of Example 30

| | | Boiling Range | | | | |
|---|---|---|---|---|---|---|
| | ° C. | Starting Material | Less than 100 | 100 to 150 | 150 to 250 | Greater than 250 |
| Volume Recovered | milliliters | 2950 | 750 | 750 | 1300 | 180 |
| Total Alkanes | wt % | 99.8 | 100.0 | 100.0 | 99.4 | 91.4 |
| Carbon Number | | Breakdown by Species Carbon Number | | | | |
| $C_{4-}$ | wt % | 0.2 | 0.4 | | | |
| $C_{5-9}$ | wt % | 52.6 | 96.0 | 78.1 | 13.7 | |
| $C_{10-14}$ | wt % | 41.3 | 3.6 | 21.9 | 78.3 | 29.9 |
| $C_{15+}$ | wt % | 5.7 | | | 7.4 | 61.5 |

Production of C5+ Compounds from Glycerol Using a Single Catalytic System

Example 31

A bimetallic catalyst system containing platinum and rhenium (5 wt % platinum with a molar ratio of Pt:Re of 1:2.5) supported on activated carbon (Calgon UU 60×120 mesh carbon) was prepared using incipient wetness techniques. Activated carbon was added slowly to a 30% hydrogen peroxide solution. After addition of the carbon was completed, the mixture was left overnight. The aqueous phase was decanted and the carbon was washed three times with of deionized water, and then dried under vacuum at 100° C. An aqueous solution, with a volume equal to incipient wetness volume for the carbon to be impregnated, 10.4 mL, and containing dihydrogen hexachloroplatinate (IV) hexahydrate (Alfa Aesar, 39.85% Pt) and perrhemic acid solution (Alfa Aesar, 76.41% $HReO_4$) was applied drop wise, while stirring, to hydrogen peroxide functionalized carbon. The wetted carbon was dried at 100° C. under vacuum.

Example 32

104.4 grams of the 1:2.5 Pt/Re catalyst were loaded into a 63.5 cm long reactor tube as described in Example 4 and Example 1, except that the temperature profile was controlled by heat exchange with a hot air stream provided by a blower and heater as illustrated in FIG. 7. The catalyst was reduced with flowing hydrogen at 350° C. for two hours before liquid feed was introduced to the catalyst bed. A 50 wt % glycerol (Colgate Palmolive USP Grade) containing about 20 ppm sulfate in water solution was fed downflow across the reactor after being preheated to 182° C. at a weight hourly space velocity of 0.97 grams of glycerol per gram of catalyst per hour. Hot air was fed upflow through the annular space at 409° C. The axial temperature profile within the center of the catalyst bed was measured using a sliding thermocouple as shown in Example 4, and is illustrated in FIG. 13. The separator pressure was maintained at 600 psig. The effluent from the reactor was cooled down with a water cooled condenser and separated in a three-phase separator. The gas-phase products were analyzed with a gas chromatograph that allowed the analysis of hydrogen, carbon dioxide, methane, ethane, propane, butane, pentane, and hexane. An organic phase was collected, weighed, and sent to Southwest Research Institute (San Antonio, Tex.) for gasoline analysis. The aqueous-phase was collected and weighed, and then analyzed using both a GCMS as well as GC-FID. In this system, there was complete conversion of the glycerol. Table 8 below shows the yields of hydrogen as well as the yields of carbon containing product compounds.

TABLE 8

Yields for the Conversion of Glycerol from Example 32

| Products | |
|---|---|
| moles of H2/mole of glycerol feed | 1.03 |
| | % Carbon/Carbon in Feed |
| CO2 | 31.79 |
| Methane | 7.35 |
| Ethane | 7.28 |
| Propane | 5.25 |
| Butane | 0.56 |
| Pentane | 1.40 |
| Hexane | 2.05 |
| C7-C13 Normal | 0.87 |
| C4-C13 Iso | 2.87 |
| C6-C12 Aromatic | 3.87 |
| C8-C11 Naphthalene/Napthenes | 1.89 |
| C5-C10 Olefins | 5.67 |
| C4-C6 Oxygenated Compounds in Organic Phase | 1.86 |
| Ethanol in Aqueous Phase | 0.39 |
| Acetic Acid in Aqueous Phase | 1.33 |
| Acetone in Aqueous Phase | 13.19 |

TABLE 8-continued

Yields for the Conversion of Glycerol from Example 32

| Products | |
|---|---|
| Propanoic Acid in Aqueous Phase | 4.69 |
| Propylene Glycol in Aqueous Phase | 2.79 |
| 1-Propanol in Aqueous Phase | 1.71 |
| Isopropyl Alcohol in Aqueous Phase | 1.28 |
| C4/C5/C6 in Aqueous Phase | 2.20 |

Production of C5+ Compounds from Sugar Alcohols

Example 33

Experiments were conducted with aqueous solutions of oxygenated hydrocarbons (e.g., 50 wt. % glycerol/water mixture or 50 wt % sorbitol/water mixture) introduced in to the reactor system of Example 1. The feedstock was further modified by the addition of $K_2SO_4$ at various concentrations (1, 20, or 50 ppm).

Example 34

A total of 10.61 grams of the 1:2.5 Pt/Re catalyst were loaded into the 8.5 mm stainless steel reactor tube described in Example 4. The catalyst was reduced with flowing hydrogen at 350° C. for two hours before liquid feed was introduced to the catalyst bed. A 50 wt % glycerol solution containing about 1 ppm sulfate in water solution was fed downflow across the reactor at a WHSV of 1.24 grams of glycerol per gram of catalyst per hour. Subsequent tests were performed with 20 ppm and 50 ppm sulfate added as $K_2SO_4$. The block heaters were controlled at 260° C. and the separator pressure was maintained at 600 psig.

An organic phase was collected from the separated, weighed, and analyzed with a GC-MS as described in Example 5. Table 9 below shows the yields of hydrogen as well as the yields of carbon containing product compounds with the different amounts of sulfate added to the system. In this system, there was complete conversion of the glycerol. The table shows that a liquid organic phase was generated with the addition of sulfate greater than 20 ppm.

TABLE 9

Yields of Hydrogen and Carbon Containing Products from Example 34

| $K_2SO_4$ loading Sulfate | 1 | 20 | 50 |
|---|---|---|---|
| Block 1 Temperature (° C.) (FIG. 8, 10a) | 260 | 260 | 260 |
| Block 2 Temperature (° C.) (FIG. 8, 10b) | 260 | 260 | 260 |
| Block 3 Temperature (° C.) (FIG. 8, 10c) | 260 | 260 | 260 |
| Block 4 Temperature (° C.) (FIG. 8, 10d) | 260 | 260 | 260 |
| H2 produced/mole of glycerol feed | 1.67 | 1.26 | 0.72 |
| | % Carbon/Carbon in Feed | | |
| $CO_2$ | 48.9% | 44.4% | 27.4% |
| $CH_4$ | 14.5% | 12.7% | 6.1% |
| $C_2H_6$ | 18.9% | 16.0% | 6.0% |
| $C_3H_8$ | 9.4% | 7.4% | 4.8% |
| $C_4H_{10}$ | 0.6% | 0.7% | 0.2% |
| $C_5H_{12}$ | 1.0% | 1.0% | 0.3% |
| $C_6H_{14}$ | 1.1% | 0.7% | 0.1% |
| $C_6^+$ Hydrocarbons in Organic Phase | 0.0% | 0.4% | 5.4% |
| $C_2$-$C_6$ Oxygenates in Organic Phase | 0.0% | 1.7% | 7.9% |
| $C_2$-$C_6$ Oxygenates in Aqueous Phase | 6.9% | 13.3% | 42.6% |

Example 35

A total of 10.61 grams of the 1:2.5 Pt/Re catalyst were loaded into the 8.5 mm stainless steel reactor tube described in Example 4 and the reactor system illustrated in Example 1. The catalyst was reduced with flowing hydrogen at 350° C. for two hours before liquid feed was introduced to the catalyst bed. A 50 wt % glycerol solution containing either 1 ppm or 20 ppm sulfate in water was fed downflow across the reactor at a WHSV of 1.24 grams of glycerol per gram of catalyst per hour. The block heaters were controlled such that the first 10.1 cm of the reactor was held at 260° C., the second 10.1 cm of the reactor was at approximate 306° C., the next 10.1 cm of the reactor was at approximately 355° C., and the last 10.1 cm of the reactor at 400° C. The separator pressure was maintained at 600 psig.

The effluent from the reactor was cooled down with a water cooled condenser, separated in a three-phase separator, and then analyzed as described in Example 5. In this system, there was complete conversion of the glycerol. Table 10 below shows the yields of hydrogen as well as the yields of carbon containing product compounds.

TABLE 10

Yields of Hydrogen and Carbon Containing Products from Example 35

| | | |
|---|---|---|
| $K_2SO_4$ loading Sulfate | 1 | 20 |
| Block 1 Temperature (° C.) | 260 | 260 |
| Block 2 Temperature (° C.) | 307 | 305 |
| Block 3 Temperature (° C.) | 354 | 356 |
| Block 4 Temperature (° C.) | 400 | 400 |
| H2 produced/mole of glycerol feed | 1.01 | 0.83 |
| | % Carbon/Carbon in Feed | |
| $CO_2$ | 42.8% | 41.7% |
| $CH_4$ | 15.7% | 16.1% |
| $C_2H_6$ | 15.8% | 11.9% |
| $C_3H_8$ | 19.9% | 18.2% |
| $C_4H_{10}$ | 1.8% | 3.0% |
| $C_5H_{12}$ | 2.3% | 3.4% |
| $C_6H_{14}$ | 1.0% | 1.7% |
| $C_6^+$ Hydrocarbons in Organic Phase | 0.0% | 1.1% |
| $C_2$-$C_6$ Oxygenates in Organic Phase | 0.0% | 0.7% |
| $C_2$-$C_6$ Oxygenates in Aqueous Phase | 0.2% | 0.1% |

Example 36

A bimetallic catalyst system containing platinum and rhenium (5 wt % platinum with a molar ratio of Pt:Re of 1:5) supported on activated carbon (Calgon UU 60×120 mesh carbon) was prepared using an incipient wetness technique. Activated carbon was added slowly to a 30% hydrogen peroxide solution. After addition of the carbon was completed, the mixture was left overnight. The aqueous phase was decanted and the carbon was washed three times with deionized water, and then dried under vacuum at 100° C. An aqueous solution, with a volume equal to the incipient wetness volume for the carbon to be impregnated and containing dihydrogen hexachloroplatinate (IV) hexahydrate (Alfa Aesar, 39.85% Pt) and perrhemic acid solution (Alfa Aesar, 76.41% $HReO_4$) was applied drop wise, while stirring, to hydrogen peroxide functionalized carbon. The wetted carbon was then dried at 100° C. under vacuum.

Example 37

11.97 grams of the 1:5 Pt/Re catalyst described in Example 36 were loaded into the 8.5 mm diameter stainless steel tube as described in Example 4 and the reactor system illustrated in Example 1. The catalyst was reduced with flowing hydrogen at 350° C. for two hours before liquid feed was introduced to the catalyst bed. A 57.2 wt % sorbitol solution containing 0 ppm sulfate in water solution was fed downflow across the reactor at a WHSV of 1.20 grams of sorbitol per gram of catalyst per hour. The block heaters were controlled such that the first 10.1 cm of the reactor was held at 260° C., the second 10.1 cm of the reactor was at 260° C., the next 10.1 cm of the reactor was at 360° C., and the last 10.1 cm of the reactor at 41° C. The separator pressure was maintained at 600 psig. The effluent from the reactor was cooled down with a water cooled condenser and separated in a three-phase separator. The product fractions were analyzed as described in Example 5. In addition, the organic phase was collected, separated, and weighed, with a sample sent to Southwest Research Institute (San Antonia, Tex.) for gasoline analysis. In this system, there was complete conversion of the glycerol. Table 11 below shows the yields of hydrogen as well as the yields of carbon containing product compounds.

TABLE 11

Yields of Hydrogen and Carbon Containing Products from Example 37

| | |
|---|---|
| Block 1 Temperature (° C.) (FIG. 8, 10a) | 260 |
| Block 2 Temperature (° C.) (FIG. 8, 10b) | 260 |
| Block 3 Temperature (° C.) (FIG. 8, 10c) | 360 |
| Block 4 Temperature (° C.) (FIG. 8, 10d) | 410 |
| Products | |
| moles of H2/mole of Sorbitol feed | 1.36 |
| | % Carbon/Carbon in Feed |
| CO2 | 44.37 |
| Methane | 9.24 |
| Ethane | 8.25 |
| Propane | 11.74 |
| Butane | 6.53 |
| Pentane | 5.66 |
| Hexane | 3.79 |
| C7-C13 Normal | 0.08 |
| C4-C13 Isoparaffin | 0.99 |
| C6-C12 Aromatic | 2.45 |
| C8-C11 Naphthalene/Napthenes | 0.93 |
| C5-C10 Olefins | 0.45 |
| C4-C6 Oxygenated Compounds in Organic Phase | 1.68 |
| Oxygenates in Aqueous Phase | 3.83 |

Conversion of Oxygenates to C5+ Compounds Using Acidic Catalysts

Example 38

An aqueous 1.0 molar lanthanum nitrate solution was prepared and added to H-mordenite extrudates (BASF 712A-5-2641-1) for a target of 3 weight % La on the catalyst after the subsequent decomposition of the metal precursor. The La solution was mixed briefly with the catalyst and then soaked at 80° C. for 6 hours. The excess liquid was then removed and the catalyst rinsed with deionized water. The catalyst was then dried in a vacuum oven and calcined in air at 55° C. Following this, the catalyst was ground and sieved to restrict the particles sizes to those that were maintained on a 60 mesh screen after passing through an 18 mesh screen.

Example 39

Deionized water was added to H-mordenite extrudates (BASF 712A-5-2641-1, with particle sizes restricted to those that were maintained on a 60 mesh screen after passing through an 18 mesh screen) until extra water covered the support. An aqueous 0.36 molar nickel nitrate solution was then added to the wet support to target 1 weight % Ni after decomposition of the metal precursor. The catalyst was mixed briefly and left to soak for 48 hours. The catalyst was then dried in a vacuum oven and calcined in air at 400° C.

Example 40

An aqueous 1.0 molar europium chloride solution was prepared and added to H-Mordenite (BASF 712A-5-2641-1, with particle sizes restricted to those that were maintained on a 60 mesh screen after passing through an 18 mesh screen) for a target of 3 weight % Eu on the catalyst after the subsequent decomposition of the metal precursors. The Eu solution was mixed briefly with the catalyst and then soaked at 80° C. for 6 hours. The excess liquid was then removed and the catalyst rinsed with deionized water. The catalyst was then dried in a vacuum oven and calcined in air at 550° C. Following this the catalyst was ground and sieved to restrict the particles sizes to those that were maintained on a 60 mesh screen after passing through an 18 mesh screen.

Example 41

H-Beta zeolite extrudates (1.6 mm diameter extrudates) were ground and sieved to restrict the particle sizes to those that were maintained on a 60 mesh screen after passing through an 18 mesh screen. An aqueous gallium nitrate solution was added by incipient wetness to target 1.2 weight % Ga on the catalyst after decomposition of the metal precursor. The catalyst was then dried in a vacuum oven and calcined in air at 400° C.

Example 42

Phosphoric acid was diluted with deionized water and added by incipient wetness to a Davicat $SiO_2/Al_2O_3$ support (Grace-Davis, with particle sizes restricted to those that were maintained on a 60 mesh screen after passing through an 18 mesh screen) to target 5 weight % phosphorous on the catalyst. The catalyst was then dried in a vacuum oven overnight and subsequently calcined in a stream of flowing air at 500° C.

Example 43

An aqueous nickel nitrate solution was added to an alumina bound ZSM-5 zeolite preparation ($SiO_2:Al_2O_3$ 30:1, with particle sizes restricted to those that were maintained on a 60 mesh screen after passing through an 18 mesh screen) using an incipient wetness technique to target a nickel loading of 1.0 weight %. The preparation was dried overnight in a vacuum oven and subsequently calcined in a stream of flowing air at 400° C.

Example 44

An aqueous gallium nitrate solution was added to an alumina bound ZSM-5 zeolite preparation ($SiO_2:Al_2O_3$ 80:1, with particle sizes restricted to those that were maintained on a 60 mesh screen after passing through an 18 mesh screen) using an incipient wetness technique to target a gallium loading of 1.2 weight %. The preparation was dried overnight in a vacuum oven and subsequently calcined in a stream of flowing air at 400° C.

Example 45

Catalyst systems produced using the methods of Examples 38 to 44 were investigated for the vapor-phase condensation of various oxygenates at a temperature from 325° C. to 375° C. and a total pressure between 200 psig and 625 psig, and with WHSVs ranging from 1.9 to 42.8. In these investigations, two different size reactors were used; 15 and 18 milliliters of catalyst were loaded into a 8.5 mm internal diameter stainless steel tube reactor or between 50 and 70 milliliters of catalyst were loaded into a 21.2 mm stainless steel tube reactor (Example 4). The reaction process flow was as described in Example 1 or Example 3 depending on the feedstock, with an analysis completed as described in Example 5.

Operating conditions and results from these experiments are shown in Table 12. Where feed compositions add up to less than 100%, the balance was water. As these results show, a variety of oxygenates, including alcohols and ketones, both 3 carbon and 5 carbon, are substrates which may be converted to $C_{5+}$ hydrocarbons across a broad range of conditions. Zeolites are particularly useful in these conversions, as shown by experiments FF, GG, HH, II, JJ, LL, and MM. Experiments FF, GG, HH, II, and JJ show that the main products of alcohol conversion across mordenite and beta zeolites were olefinic condensation products. The phosphorous impregnated silica alumina catalyst, experiment KK, demonstrated a similar product selectivity profile. In contrast, the ZSM-5 based catalysts, Experiments LL and MM, produced significant fractions of aromatic and paraffinic components.

TABLE 12

Vapor Phase Condensation of Oxygenates Over Acid Catalysts

| | | Catalyst | | | | | | |
|---|---|---|---|---|---|---|---|---|
| | | La/ mordenite | Ni/ mordenite | Eu/ mordenite | Eu/ mordenite | Ga/Beta | 5% Phosphorous/Silica-Alumina | Ni/30:1 SiO2:Al2O3 ZSM-5 | Ga/80:1 SiO2:Al2O3 ZSM-5 |
| | | | | | Experiment | | | | |
| | | FF | GG | HH | II | JJ | KK | LL | MM |
| Feed | | 50% 2-pentanol | 50% isopropyl alcohol | 59% 2-pentanol | 50% isopropyl alcohol | 50% isopropyl alcohol | 90% isopropyl alcohol | 50% isopropyl alcohol | 89.6% Acetone |
| WHSV | $wt_{feed}/(wt_{catalyst}\,hr)$ | 1.9 | 2.1 | 2.2 | 1.9 | 3.1 | 2.7 | 42.8 | 2.1 |
| Reactor Temperature | ° C. | 325 | 350 | 325 | 375 | 375 | 375 | 375 | 375 |
| Pressure | psig | 625 | 625 | 600 | 600 | 600 | 600 | 200 | 625 |

TABLE 12-continued

Vapor Phase Condensation of Oxygenates Over Acid Catalysts

| | | Catalyst | | | | | | | |
|---|---|---|---|---|---|---|---|---|---|
| | | La/ mordenite | Ni/ mordenite | Eu/ mordenite | Eu/ mordenite | Ga/Beta Experiment | 5% Phosphorous/Silica-Alumina | Ni/30:1 SiO2:Al2O3 ZSM-5 | Ga/80:1 SiO2:Al2O3 ZSM-5 |
| | | FF | GG | HH | II | JJ | KK | LL | MM |
| | | Reactor Outlet Yield Distribution | | | | | | | |
| $C_{4-}$ Alkanes | wt % of feed carbon | 2.9 | 0.7 | 3.9 | 3.6 | 1.2 | 1.6 | 9.6 | 7.0 |
| $C_{4-}$ Olefins | wt % of feed carbon | 19.5 | 47.7 | 11.3 | 32.9 | 32.5 | 73.5 | 10.8 | 0.5 |
| Total $C_{4-}$ Hydrocarbons | wt % of feed carbon | 22.3 | 48.4 | 15.3 | 36.5 | 33.7 | 75.1 | 20.5 | 7.5 |
| $C_{5+}$ Paraffins | wt % of feed carbon | 6.6 | 0.8 | 16.9 | 3.1 | 4.3 | 1.9 | 29.6 | 8.5 |
| $C_{5+}$ Olefins | wt % of feed carbon | 56.2 | 46.9 | 43.1 | 56.6 | 52.0 | 18.4 | 21.7 | 0.1 |
| Naphthenes | wt % of feed carbon | 0.0 | 2.5 | 1.5 | 5.6 | 3.2 | 3.4 | 2.7 | 1.0 |
| Aromatics | wt % of feed carbon | 0.0 | 0.0 | 1.4 | 0.0 | 2.0 | 0.0 | 18.0 | 79.1 |
| Other $C_{5+}$ Hydrocabons | wt % of feed carbon | 0.8 | 0.1 | 5.7 | 1.5 | 0.2 | 0.0 | 7.1 | 0.0 |
| Total $C_{5+}$ Hydrocarbons | wt % of feed carbon | 63.6 | 50.3 | 68.6 | 66.7 | 61.8 | 23.7 | 79.2 | 88.6 |

Production of C5+ Compounds from Oxygenated Hydrocarbons

Example 46

A catalyst preparation technique identical to that of Example 44 was followed with the exception that the alumina bound ZSM-5 material had a $SiO_2:Al_2O_3$ ratio of 30:1.

Example 47

A catalyst produced using the method of Example 46 was investigated for the vapor-phase condensation of a mixture of oxygenates at 375° C. and 200 psig. In this investigation, 11.3 grams of catalyst were loaded into a 8.5 mm internal diameter stainless steel tube reactor as described in Example 4. The reaction process flow was as described in Example 3. The oxygenate mix included, by weight, 25% 2-pentanone, 20% 3-pentanone, 20% 2-pentanol, 10% isopropyl alcohol, 10% valeric acid, 5% 2-methyl tetrahydrofuran. This mixture was added using one pump in the Example 3 reactor system while the second pump added water so that the total combined feed contained 60 weight % water and 40 weight % of mixed oxygenates.

The process was monitored for a period of 128 hours, with samples periodically removed from the system to analyze the process performance. Each analysis was completed as described in Example 5. FIG. 15 shows the fraction of feed carbon that exited the reactor system as $C_{5+}$ compounds as a function of time. FIG. 16 shows the fraction of feed carbon that exited the reactor system as an aromatic hydrocarbon as a function of time. FIG. 14 shows the fraction of feed carbon that exited the reactor system as oxygenates as a function of time.

As FIGS. 14, 15 and 16 show, the catalyst system is able to operate for extended periods of time with an oxygenate mix that contains a mixture of oxygenates, including alcohols, ketones, an acid, and a tetrahydrofuran. Over time the production of $C_{5+}$ compounds remains relatively stable, while the amount of aromatic hydrocarbons present in the product drops and the breakthrough of oxygenated compounds increases (FIG. 14). It is believed that the catalyst deactivation is primarily due to the accumulation of carbonaceous deposits limiting the accessibility of the reactants to the active sites.

Example 48

An aqueous solution of hexachloroplatinic acid and perrhenic acid was added to a carbon catalyst support (OLC-AW, Calgon, with particle sizes restricted to those that were maintained on a 50 mesh screen after passing through an 120 mesh screen) using an incipient wetness technique to target a platinum loading of 1.8% and a rhenium loading of 6.3% on the catalyst after subsequent decomposition of the metal precursors. The preparation was dried overnight in a vacuum oven and subsequently reduced in a stream of flowing hydrogen at 400° C. After being reduced the catalyst was stored in a nitrogen atmosphere until ready for use.

Example 49

A catalyst preparation technique identical to that of Example 44 was followed with the exception that the alumina bound ZSM-5 material had a $SiO_2:Al_2O_3$ ratio of 150:1.

Example 50

Hexachloroplatinic acid and perrhenic acid dissolved in water were added to a monoclinic zirconia catalyst support (N or Pro Saint Gobain, product code SZ31164, with particle sizes restricted to those that were maintained on a 60 mesh screen after passing through an 18 mesh screen) using an incipient wetness technique to target a platinum loading of 1.8% and a rhenium loading of 6.3% on the catalyst after subsequent decomposition of the metal precursors. The preparation was dried overnight in a vacuum oven and subsequently calcined in a stream of flowing air at 400° C.

Example 51

The same procedure used for preparing the catalyst of Example 50 was followed with the exception that the target rhenium loading was 1.8%.

Example 52

An 80:1 $SiO_2:Al_2O_3$ ratio ZSM-5 zeolite (Zeolyst International, CBV 8014) was mixed with a 1:1 molar ratio of ZnO and $Al_2O_3$ powders so that the ZnO and $Al_2O_3$ (Dispal 18N4-80, Sasol North America, Houston, Tex.) combined comprised 30 weight % of the total solids. Dilute nitric acid was added at a level of 2 weight % $HNO_3$ to the combined ZnO and $Al_2O_3$. The dough consistency was adjusted with water addition to form a workable dough suitable for extrusion and the mixture was extruded using a laboratory scale extruder. The extrudates were dried overnight under vacuum at 100° C. and subsequently calcined at 600° C. under flowing air.

Example 53

An aqueous solution of gallium nitrate was added to the material of Example 52, with particle sizes restricted to those that were maintained on a 60 mesh screen after passing through an 18 mesh screen, using an incipient wetness technique to target a gallium loading of 1.2 weight %. The preparation was dried overnight in a vacuum oven and subsequently calcined in a stream of flowing hydrogen at 400° C.

Example 54

An aqueous solution of nickel nitrate was added to the material of Example 52, with particle sizes restricted to those that were maintained on a 60 mesh screen after passing through an 18 mesh screen, using an incipient wetness technique to target a nickel loading of 1.0 weight %. The preparation was dried overnight in a vacuum oven and subsequently calcined in a stream of flowing hydrogen at 400° C.

Example 55

The catalyst systems referenced in Examples 6, 46, 48, 49, 51, 53, and 54 were investigated for the conversion of glycerol, sorbitol, sucrose, and xylose to hydrocarbons using the reactor configuration described in Example 2. The studies were conducted using two 21.2 mm internal diameter stainless steel tube reactors shown in Example 4, with an analysis completed as described in Example 5. Tungstated zirconia (N or Pro-Saint Gobain, product code SZ61143, with particle sizes restricted to those that were maintained on a 60 mesh screen after passing through an 18 mesh screen) was placed on top of the condensation catalyst installed in the second reactor to provide for a zone for vaporization of the first reactor effluent prior to entering the condensation catalyst.

Table 13 shows the results of these investigations. For Experiment NN (38% Sucrose+7% Xylose), a stream of hydrogen with a targeted flow rate equal to 3 times the moles of sucrose plus 1.5 times the moles of xylose was combined with the feed prior to entering the reactor. The other experiments were conducted without externally supplied hydrogen. Heaters external to the reactor, shown in FIG. 9 as 10$a$, 10$b$, 10$c$, 10$d$, 23$a$, 23$b$, 23$c$, and 23$d$, were used to maintain the reactor wall temperatures, as indicated in Table 13. The hydrocarbon products of these studies, disclosed in Table 13, were grouped into a $C_{4-}$ fraction, which are predominately present in the gas phase at ambient temperature and pressure, and a $C_{5+}$ fraction, which are generally suitable for incorporation into liquid fuels. The results show that a variety of sugars and polyhydric alcohols may be readily converted to $C_{5+}$ hydrocarbons by the processes described here. The products contained mainly paraffin and aromatic constituents. The breakdown of paraffins and aromatics within this sample is shown in FIG. 17.

TABLE 13

| Conversion of Sugars and Polyhydric Alcohols to C5+ Hydrocarbons | | | | |
|---|---|---|---|---|
| Experiment | NN | OO | PP | QQ |
| Catalyst Descriptions | | | | |
| Hydrogenation | Example 6 | None | None | None |
| APR/Deoxygenation | Example 48 | Example 51 | Example 51 | Example 50 |
| Condensation | Example 49 | Example 53 | Example 46 | Example 54 |
| Catalyst Loadings | | | | |
| Hydrogenation grams | 10 | — | — | — |
| APR/Deoxygenation grams | 40 | 52 | 60 | 60 |
| Tungstated Zirconia grams | 71 | 60 | ~60 | 58 |
| Condensation grams | 62 | 60 | 60 | 60 |
| Heater Block Temperature Ranges, Inlet of Catalayst Bed-Outlet of Catalyst Bed | | | | |
| Hydrogenation ° C. | 100-150 | — | — | — |
| APR/Deoxygenation ° C. | 245-265 | 250-270 | 335-365 | 275-285 |
| Tungstated Zirconia ° C. | 250-375 | 370-370 | 395-375 | 395-375 |
| Condensation ° C. | 375-375 | 385-385 | 375-375 | 375-375 |
| Pressures | | | | |
| First Reactor Outlet psig | 625 | 625 | 625 | 625 |
| 2nd Reactor Outlet psig | 625 | 350 | 250 | 350 |
| Feed | 38% Sucrose + 7% Xylose | 50% Glycerol | 50% Glycerol | 50% Sorbitol |

TABLE 13-continued

Conversion of Sugars and Polyhydric Alcohols to C5+ Hydrocarbons

| Experiment | | NN | OO | PP | QQ |
|---|---|---|---|---|---|
| Hydrogen production | mol/mol feed | −2.85 | 0.73 | 0.57 | 0.50 |
| WHSV | $wt_{feed}/(wt_{catalyst} hr)$ | 1.6 | 1.9 | 2.0 | 2.0 |
| Reactor Outlet Yield Distribution | | | | | |
| $C_{4-}$ Alkanes | wt % of feed carbon | 21.2 | 26.9 | 8.1 | 13.0 |
| $C_{4-}$ Olefins | wt % of feed carbon | 1.1 | 1.4 | 1.3 | 5.2 |
| Total $C_{4-}$ Hydrocarbons | wt % of feed carbon | 22.3 | 28.3 | 9.4 | 18.1 |
| $C_{5+}$ Paraffins | wt % of feed carbon | 20.0 | 7.9 | 9.5 | 11.3 |
| $C_{5+}$ Olefins | wt % of feed carbon | 0.8 | 1.9 | 1.2 | 7.8 |
| Naphthenes | wt % of feed carbon | 1.9 | 1.4 | 1.6 | 1.2 |
| Aromatics | wt % of feed carbon | 25.0 | 17.8 | 48.4 | 22.3 |
| Other $C_{5+}$ Hydrocabons | wt % of feed carbon | 0.0 | 1.1 | 0.2 | 3.4 |
| Total $C_{5+}$ Hydrocarbons | wt % of feed carbon | 47.7 | 30.1 | 61.0 | 46.1 |

Example 56

The process described in Example 55 and exemplified by Experiment QQ in Table 13 was operated for a period of more than 400 hours. After an initial period of time in operation, the conversion to aromatic components and the yield of hydrocarbons dropped, shown in FIGS. 18 and 19 as Cycle 1. In FIG. 18, the heating value of $C_{5+}$ hydrocarbons present at the outlet of the second reactor, as a percentage of the heating value of the feed, is shown. In FIG. 19, the carbon present as aromatic hydrocarbons at the outlet of the second reactor is shown as a percentage of the carbon present in the feed. After approximately 120 hours on stream, the second reactor was bypassed while the first reactor continued operating. An oxidative regeneration of the catalyst in the second reactor was then performed. During the regeneration, a flow of nitrogen and air was initiated so that the target oxygen concentration at the second reactor inlet was 1 mol %. The second reactor block temperatures were then raised to 500° C. and the flow of nitrogen and oxygen continued until carbon dioxide was no longer detected at the second reactor outlet. The oxygen concentration was then raised to a target level of 5 mol %. This flow was continued until carbon dioxide was no longer detected at the second reactor outlet. At this time the oxygen flow was discontinued while the nitrogen flow continued. The second reactor block temperatures were then reduced to 400° C. while the composition of the gas flowing through the catalyst bed was changed to hydrogen. The second reactor block temperatures were then adjusted to those shown for Experiment QQ in Table 13. The second reactor was then placed back on line, targeting the conditions shown for Experiment QQ in Table 13. The second reactor was then subjected to multiple cycles of operation and regeneration, with the results for the period of time in operation shown in FIGS. 18 and 19. As these results show, the regeneration of the condensation catalyst resulted in a restoration of activity, consistent with the theory that deposition of carbonaceous materials were the main cause of a drop in catalyst performance over time. Furthermore, the results show that the condensation catalyst may be regenerated multiple times without a significant loss of performance.

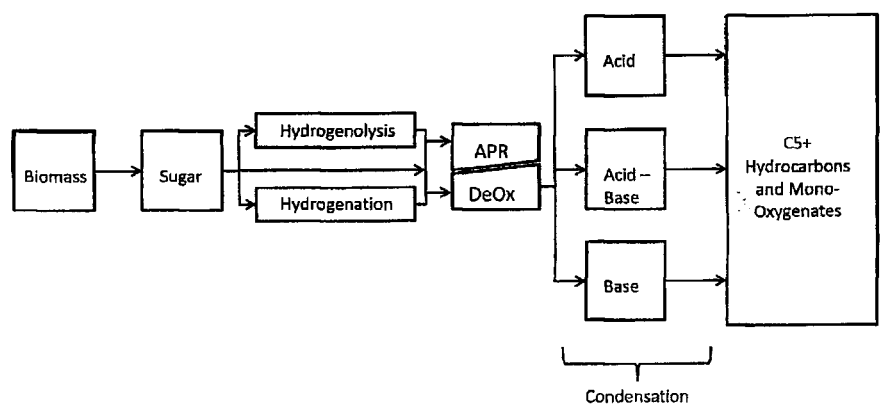

We claim:

1. A method of making a $C_{4+}$ compound comprising:
providing water and a water soluble oxygenated hydrocarbon comprising a $C_{1+}O_{1+}$ hydrocarbon in an aqueous liquid phase and/or a vapor phase,
providing $H_2$,
catalytically reacting in the liquid and/or vapor phase the oxygenated hydrocarbon with the $H_2$ in the presence of a deoxygenation catalyst at a deoxygenation temperature and deoxygenation pressure to produce an oxygenate comprising a $C_{1+}O_{1-3}$ hydrocarbon in a reaction stream, and
catalytically reacting in the liquid and/or vapor phase the oxygenate in the presence of a base catalyst at a condensation temperature and condensation pressure to produce the $C_{4+}$ compound,
wherein the $C_{4+}$ compound comprises a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and a mixture thereof.

2. The method of claim 1, wherein the water soluble oxygenated hydrocarbon is derivable from biomass.

3. The method of claim 2, wherein the $H_2$ comprises in situ generated $H_2$, external $H_2$, recycled $H_2$, or a combination thereof.

4. The method of claim 2, wherein the $H_2$ comprises in situ generated $H_2$ generated by catalytically reacting in a liquid phase and/or vapor phase a portion of the water and oxygenated hydrocarbon in the presence of an aqueous phase reforming catalyst at a reforming temperature and reforming pressure to produce in situ generated $H_2$.

5. The method of claim 4, wherein the aqueous phase reforming catalyst comprises a support and a member selected from the group consisting of Fe, Ru, Os, Ir, Co, Rh, Pt, Pd, Ni, an alloy thereof, and a combination thereof.

6. The method of claim 5, wherein the aqueous phase reforming catalyst further comprises a member selected from the group consisting of Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, an alloy thereof, and a combination thereof.

7. The method of claim 5, wherein the support comprises a member selected from the group consisting of a nitride, carbon, silica, alumina, zirconia, titania, vanadia, ceria, boron nitride, heteropolyacid, kieselguhr, hydroxyapatite, zinc oxide, chromia, zeolites, and mixtures of any of the foregoing.

8. The method of claim 4, wherein at least two of the aqueous phase reforming catalyst, deoxygenation catalyst, and condensation catalyst are atomically identical.

9. The method of claim 4, wherein the aqueous phase reforming catalyst and deoxygenation catalyst comprise Pt alloyed or admixed with a member selected from the group consisting of Ni, Ru, Cu, Fe, Rh, Re, Au, Ag, alloys thereof, and a combination thereof.

10. The method of claim 4, wherein the aqueous phase reforming catalyst and deoxygenation catalyst comprise Ru alloyed or admixed with a member selected from the group consisting of Ge, Bi, B, Ni, Sn, Cu, Fe, Rh, Pt, Au, Ag, alloys thereof, and a combination thereof.

11. The method of claim 4, wherein the aqueous phase reforming catalyst comprises Ni alloyed or admixed with a member selected from the group consisting of Sn, Ge, Bi, B, Cu, Re, Ru, Fe, Au, Ag, alloys thereof, and a combination thereof.

12. The method of claim 4, wherein the reforming temperature is in the range of about 100° C. to about 450° C., and wherein the reforming pressure is a pressure where the water and the oxygenated hydrocarbon are gaseous.

13. The method of claim 4, wherein the reforming temperature is in the range of about 100° C. to about 300° C., and wherein the reforming pressure is a pressure where the water and the oxygenated hydrocarbon are gaseous.

14. The method of claim 4, wherein the reforming temperature is in the range of about 80° C. to 400° C., and wherein the reforming pressure is a pressure where the water and the oxygenated hydrocarbon are liquid.

15. The method of claim 2, wherein the deoxygenation temperature is in the range of about 200° C. to 280° C., and wherein the deoxygenation pressure is a pressure where the water and the oxygenated hydrocarbon are gaseous.

16. The method of claim 4, wherein the reforming temperature and deoxygenation temperature is in the range of about 100° C. to 450° C., and wherein the reforming pressure and deoxygenation pressure is in the range of about 72 psig to 1300 psig.

17. The method of claim 4, wherein the reforming temperature and deoxygenation temperature is in the range of about 120° C. to 300° C., and wherein the reforming pressure and deoxygenation pressure is in the range of about 72 psig to 1200 psig.

18. The method of claim 4, wherein the reforming temperature and deoxygenation temperature is in the range of about 200° C. to 280° C., and wherein the reforming pressure and deoxygenation pressure is in the range of about 200 psig to 725 psig.

19. The method of claim 4, wherein the molar ratio of the total oxygen atoms in the oxygenated hydrocarbons to the total hydrogen atoms in the supplemental $H_2$ is less than 1:1.

20. The method of claim 2, wherein the oxygenated hydrocarbon comprises a member selected from the group consisting of polysaccharides, disaccharides, monosaccharides, cellulose derivatives, lignin derivatives, hemicellulose, sugars, sugar alcohols and a mixture thereof.

21. The method of claim 20, wherein the oxygenated hydrocarbon comprises a $C_{1-12}O_{1-11}$ hydrocarbon.

22. The method of claim 21, wherein the oxygenated hydrocarbon comprises a $C_{1-12}O_{1-6}$ hydrocarbon.

23. The method of claim 21, wherein the $C_{1-12}O_{1-11}$ hydrocarbon comprises a member selected from the group consisting of a sugar alcohol, sugar, monosaccharide, disaccharide, alditol, cellulosic derivative, lignocellulosic derivative, glucose, fructose, sucrose, maltose, lactose, mannose, xylose, arabitol, erythritol, glycerol, isomalt, lactitol, malitol, mannitol, sorbitol, xylitol, and a mixture thereof.

24. The method of claim 2, wherein the oxygenated hydrocarbon further comprises recycled $C_{1+}O_{1+}$ hydrocarbon.

25. The method of claim 2, wherein the oxygenate comprises a member selected from the group consisting of an alcohol, ketone, aldehyde, furan, diol, triol, hydroxy carboxylic acid, carboxylic acid, and a mixture thereof.

26. The method of claim 2, wherein the oxygenate comprises a member selected from the group consisting of methanol, ethanol, n-propyl alcohol, isopropyl alcohol, butyl alcohol, pentanol, hexanol, cyclopentanol, cyclohexanol, 2-methylcyclopentanol, hydroxyketones, cyclic ketones, acetone, propanone, butanone, pentanone, hexanone, 2-methyl-cyclopentanone, ethylene glycol, 1,3-propanediol, propylene glycol, butanediol, pentanediol, hexanediol, methylglyoxal, butanedione, pentanedione, diketohexane, hydroxyaldehydes, acetaldehyde, propionaldehyde, butyraldehyde, pentanal, hexanal, formic acid, acetic acid, propionic acid, butanoic acid, pentanoic acid, hexanoic acid, lactic acid, glycerol, furan, tetrahydrofuran, dihydrofuran, 2-furan methanol, 2-methyl-tetrahydrofuran, 2,5-dimethyl-tetrahydrofuran, 2-ethyl-tetrahydrofuran, 2-methyl furan, 2,5-dimethyl furan, 2-ethyl furan, hydroxylmethylfurfural, 3-hydroxytetrahydrofuran, tetrahydro-3-furanol, 5-hydroxymethyl-2 (5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, and hydroxymethyltetrahydrofurfural, isomers thereof, and combinations thereof.

27. The method of claim 2, wherein the oxygenate further comprises recycled $C_{1+}O_{1-3}$ hydrocarbon.

28. The method of claim 2, wherein the $C_{4+}$ alkane comprises a branched or straight chain $C_{4-30}$ alkane.

29. The method of claim 2, wherein the $C_{4+}$ alkane comprises a branched or straight chain alkane selected from the group consisting of $C_{4-9}$, $C_{7-14}$, $C_{12-24}$, and a mixture thereof.

30. The method of claim 2, wherein the $C_{4+}$ alkene comprises a branched or straight chain $C_{4-30}$ alkene.

31. The method of claim 2, wherein the $C_{4+}$ alkene comprises a branched or straight chain alkene selected from the group consisting of $C_{4-9}$, $C_{7-14}$, $C_{12-24}$ and a mixture thereof.

32. The method of claim 2, wherein the $C_{5+}$ cycloalkane comprises a mono-substituted or multi-substituted $C_{5+}$ cycloalkane, and wherein at least one substituted group is a member selected from the group consisting of a branched $C_{3+}$ alkyl, a straight chain $C_{1+}$ alkyl, a branched $C_{3+}$ alkylene, a straight chain $C_{1+}$ alkylene, a phenyl, and a combination thereof.

33. The method of claim 32, wherein the mono-substituted or multi-substituted $C_{5+}$ cycloalkane is substituted with a member selected from the group consisting of a branched $C_{3-12}$ alkyl, a straight chain $C_{1-12}$ alkyl, a branched $C_{3-12}$ alkylene, a straight chain $C_{1-12}$ alkylene, a phenyl, and a combination thereof.

34. The method of claim 32, wherein the substituted group is a member selected from the group consisting of a branched $C_{3-4}$ alkyl, a straight chain $C_{1-4}$ alkyl, a branched $C_{3-4}$ alkylene, straight chain $C_{1-4}$ alkylene, a phenyl, and a combination thereof.

35. The method of claim 2, wherein the $C_{5+}$ cycloalkene comprises a mono-substituted or multi-substituted $C_{5+}$ cycloalkene, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof.

36. The method of claim 35, wherein the mono-substituted or multi-substituted $C_{5+}$ cycloalkene is substituted with a member selected from the group consisting of a branched $C_{3-12}$ alkyl, a straight chain $C_{1-12}$ alkyl, a branched $C_{3-12}$ alkylene, a straight chain $C_{2-12}$ alkylene, a phenyl, and a combination thereof.

37. The method of claim 35, wherein the substituted group is a member selected from the group consisting of a branched $C_{3-4}$ alkyl, a straight chain $C_{1-4}$ alkyl, a branched $C_{3-4}$ alkylene, straight chain $C_{2-4}$ alkylene, a phenyl, and a combination thereof.

38. The method of claim 2, wherein the aryl comprises an unsubstituted aryl.

39. The method of claim 2, wherein the aryl comprises a mono-substituted or multi-substituted aryl, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof.

40. The method of claim 39, wherein the substituted group is a member selected from the group consisting of a branched $C_{3-12}$ alkyl, a straight chain $C_{1-12}$ alkyl, a branched $C_{3-12}$ alkylene, a straight chain $C_{2-12}$ alkylene, a phenyl, and a combination thereof.

41. The method of claim 39, wherein the substituted group is a member selected from the group consisting of a branched $C_{3-4}$ alkyl, a straight chain $C_{1-4}$ alkyl, a branched $C_{3-4}$ alkylene, a straight chain $C_{2-4}$ alkylene, a phenyl, and a combination thereof.

42. The method of claim 2, wherein the fused aryl comprises an unsubstituted fused aryl.

43. The method of claim 2, wherein the fused aryl comprises a mono-substituted or multi-substituted fused aryl, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof.

44. The method of claim 43, wherein the substituted group is a member selected from the group consisting of a branched $C_{3-4}$ alkyl, a straight chain $C_{1-4}$ alkyl, a branched $C_{3-4}$ alkylene, a straight chain $C_{2-4}$ alkylene, a phenyl, and a combination thereof.

45. The method of claim 2, wherein the $C_{4+}$ alcohol comprises a compound according to the formula $R^1$—OH, wherein $R^1$ is a member selected from the group consisting of a branched $C_{4+}$ alkyl, straight chain $C_{4+}$ alkyl, a branched $C_{4+}$ alkylene, a straight chain $C_{4+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl, and a combination thereof.

46. The method of claim 2, wherein the $C_{4+}$ ketone comprises a compound according to the formula

wherein $R^3$ and $R^4$ are independently a member selected from the group consisting of a branched $C_{3+}$ alkyl, a straight chain $C_{1+}$ alkyl, a branched $C_{3+}$ alkylene, a straight chain $C_{2+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl, and a combination thereof.

47. The method of claim 2, wherein the base catalyst comprises a member selected from the group consisting of hydrotalcite, zinc-aluminate, phosphate, Li, Na, K, Cs, B, Rb, Mg, Ca, Sr, Si, Ba, Al, Ce, La, Sc, Y, Zr, Ti, Zn, an alloy thereof, and a combination thereof.

48. The method of claim 47, wherein the base catalyst further comprises an oxide selected from the group consisting of Ti, Zr, V, Nb, Ta, Mo, Cr, W, Mn, Re, Al, Ga, In, Fe, Co, Mg, Ni, Si, Cu, Zn, Sn, Cd, P, and a combination thereof.

49. The method of claim 47, wherein the base catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy thereof, and a combination thereof.

50. The method of claim 2, wherein the base catalyst comprises a metal oxide of a member selected from the group consisting of Cu, Ni, Zn, V, Zr, and a combination thereof.

51. The method of claim 2, wherein the base catalyst comprises zinc aluminate and a metal selected from the group consisting of Pd, Pt, Ni, Cu, and a combination thereof.

52. The method of claim 2, wherein the deoxygenation catalyst comprises a support and a member selected from the group consisting of Re, Cu, Fe, Ru, Ir, Co, Rh, Pt, Pd, Ni, W, Os, Mo, Ag, Au, an alloy thereof, and a combination thereof.

53. The method of claim 52, wherein the deoxygenation catalyst further comprises a member selected from the group consisting of Mn, Cr, Mo, W, V, Nb, Ta, Ti, Zr, Y, La, Sc, Zn, Cd, Ag, Au, Sn, Ge, P, Al, Ga, In, Tl, and a combination thereof.

54. The method of claim 52, wherein the support comprises a member selected from group consisting of a nitride, carbon, silica, alumina, zirconia, titania, vanadia, ceria, boron nitride, heteropolyacid, kieselguhr, hydroxyapatite, zinc oxide, chromia, and mixtures thereof.

55. The method of claim 52, wherein the support is a hydrogen peroxide treated carbon.

56. The method of claim 54, wherein the support is modified by treating the support with a modifier selected from the group consisting of silanes, alkali compounds, alkali earth compounds, and lanthanides.

57. The method of claim 52, wherein the support comprises a member selected from the group consisting of carbon nanotubes, carbon fullerenes, and zeolites.

58. The method of claim 2, wherein the deoxygenation catalyst and the condensation catalyst are atomically identical.

59. The method of claim 2, wherein the deoxygenation temperature is in the range of about 100° C. to 600° C., and wherein the deoxygenation pressure is at least 0.1 atmosphere.

60. The method of claim 2, wherein the deoxygenation temperature is in the range of about 80° C. to about 300° C., and wherein the deoxygenation pressure is a pressure where the water and the oxygenated hydrocarbon are liquid.

61. The method of claim 2, wherein the deoxygenation temperature is in the range of about 200° C. to about 280° C., and wherein the deoxygenation pressure is a pressure where the water and the oxygenated hydrocarbon are liquid.

62. The method of claim 2, wherein the deoxygenation temperature is in the range of about 100° C. to 600° C., and wherein the deoxygenation pressure is a pressure where the water and the oxygenated hydrocarbon are gaseous.

63. The method of claim 2, wherein the condensation temperature is in the range of about 80° C. to 500° C., and wherein the condensation pressure is in the range of about 0 psig to 1200 psig.

64. The method of claim 2, wherein the condensation temperature is in the range of about 125° C. to 450° C., and wherein the condensation pressure is at least 0.1 atm.

65. The method of claim 2, wherein the condensation temperature is in the range of about 125° C. to 250° C., and wherein the condensation pressure is in the range of about 0 psig to 700 psig.

66. The method of claim 2, wherein the condensation temperature is in the range of about 250° C. to 425° C.

67. The method of claim 2, wherein the reaction stream further comprises water, and further comprising dewatering the reaction stream prior to reacting the oxygenate in the presence of the condensation catalyst.

68. The method of claim 2, wherein the step of catalytically reacting the oxygenated hydrocarbon with $H_2$ in the presence of the deoxygenation catalyst is conducted in the presence of an insignificantly effective amount of external $H_2$.

69. The method of claim 2, further comprising catalytically reacting in the liquid and/or vapor phase a sugar, sugar alcohol or polyhydric alcohol with $H_2$ in the presence of a hydrogenolysis catalyst at a hydrogenolysis temperature and hydrogenolysis pressure to produce the oxygenated hydrocarbon.

70. The method of claim 69, wherein the hydrogenolysis temperature is at least 110° C. and the hydrogenolysis pressure is in the range of about 10 psig to 2400 psig.

71. The method of claim 70, wherein the hydrogenolysis temperature is in the range of about 110° C. to 300° C.

72. The method of claim 69, wherein the hydrogenolysis catalyst comprises a member selected from the group consisting of phosphate, Cr, Mo, W, Re, Mn, Cu, Cd, Fe, Ru, Os, Ir, Co, Rh, Pt, Pd, Ni, alloys thereof, and a combination thereof.

73. The method of claim 72, wherein the hydrogenolysis catalyst further comprises a member selected from the group consisting of Au, Ag, Zn, Sn, Bi, B, Cr, Mn, O, alloys thereof, and a combination thereof.

74. The method of claim 72, wherein the hydrogenolysis catalyst further comprises an alkaline earth metal oxide.

75. The method of claim 72, wherein the hydrogenolysis catalyst further comprises a support, and wherein the support comprises a member selected from the group consisting of a nitride, carbon, silica, alumina, zirconia, titania, vanadia, ceria, boron nitride, heteropolyacid, kieselguhr, hydroxyapatite, zinc oxide, chromia, zeolites, and mixtures of any of the foregoing.

76. The method of claim 69, wherein the $H_2$ comprises in situ generated $H_2$, external $H_2$, recycled $H_2$, or a combination thereof.

77. The method of claim 2, further comprising catalytically reacting in the liquid and/or vapor phase a sugar, furfural, carboxylic acid, ketone, or furan with $H_2$ in the presence of a hydrogenation catalyst at a hydrogenation temperature and hydrogenation pressure to produce the oxygenated hydrocarbon.

78. The method of claim 77, wherein the hydrogenation temperature is in the range of about 80° C. to 250° C., and wherein the hydrogenation pressure is in the range of about 100 psig to 2000 psig.

79. The method of claim 77, wherein the hydrogenation catalyst comprises a support and a member selected from the group consisting of Fe, Ru, Os, Ir, Co, Rh, Pt, Pd, Ni, Re, Cu, alloys thereof, and a combination thereof.

80. The method of claim 79, wherein the hydrogenation catalyst further comprises a member selected from the group consisting of Ag, Au, Cr, Zn, Mn, Sn, Bi, Mo, W, B, P, alloys thereof, and a combination thereof.

81. The method of claim 79, wherein the support comprises a member selected from the group consisting of a nitride, carbon, silica, alumina, zirconia, titania, vanadia, ceria, boron nitride, heteropolyacid, kieselguhr, hydroxyapatite, zinc oxide, chromia, zeolites, and mixtures of any of the foregoing.

82. The method of claim 77, wherein the $H_2$ comprises in situ generated $H_2$, external $H_2$, recycled $H_2$, or a combination thereof.

83. The method of claim 2, further comprising catalytically reacting the $C_{4+}$ compound in the liquid phase and/or vapor phase in the presence of a finishing catalyst at a finishing temperature and a finishing pressure, wherein the finishing catalyst comprises a support and a member selected from the group consisting of Cu, Ni, Fe, Co, Ru, Pd, Rh, Pt, Ir, Os, an alloy thereof, and a combination thereof.

84. The method of claim 83, wherein the finishing catalyst further comprises a modifier selected from the group consisting of Au, Ag, Cr, Zn, Mn, Sn, Cu, Cr, Bi, alloys thereof, and a combination thereof.

85. The method of claim 83, wherein the support comprising a member selected from the group consisting of a nitride, carbon, silica, alumina, zirconia, titania, vanadia, ceria, boron nitride, heteropolyacid, kieselguhr, hydroxyapatite, zinc oxide, chromia, zeolites, and mixtures of any of the foregoing.

86. The method of claim 2, performed in a reactor system comprising one or more reactor vessels, wherein the reactor system is adapted to be configured as continuous flow, batch, semi-batch, multi-system or a combination thereof.

87. The method of claim 86, wherein the reactor system further comprises one or more of a fluidized catalytic bed, a swing bed, fixed bed, moving bed or a combination thereof, wherein each bed is adapted to be housed within a reactor vessel.

88. The method of claim 87, performed in the continuous flow reactor system at steady-state equilibrium.

89. The method of claim 86, further comprising:
a reforming bed adapted to contain the aqueous phase reforming catalyst,
a deoxygenation bed adapted to contain the deoxygenation catalyst, and
a condensation bed adapted to contain the condensation catalyst.

90. The method of claim 89, wherein the reforming bed and deoxygenation bed are oriented in a stacked, side-by-side or parallel configuration, and wherein the reforming and deoxygenation beds are housed within a single reactor vessel.

91. The method of claim 89, wherein the reforming bed is housed within a reforming reactor vessel, and wherein the deoxygenation bed is housed within a deoxygenation reactor vessel.

92. The method of claim 89, wherein the condensation bed is housed within a condensation reactor vessel.

93. The method of claim 89, wherein the condensation bed is housed within a condensation reactor vessel.

94. The method of claim 90, wherein the single reactor vessel is further adapted to house the condensation bed.

95. The method of claim 88, wherein the continuous flow reactor system is oriented to provide horizontal, vertical or diagonal flow.

96. The method of claim 92, wherein the deoxygenation bed is housed within a deoxygenation reactor vessel providing up-flow, and wherein the condensation bed is housed within a condensation reactor vessel providing down-flow.

97. The method of claim 93, wherein the deoxygenation bed is housed within a deoxygenation reactor vessel providing up-flow, and wherein the condensation bed is housed within a condensation reactor vessel providing down-flow.

98. The method of claim 2, wherein each catalytic reaction occurs at steady-state equilibrium.

99. A method of making a $C_{4+}$ compound comprising:
providing water and a water soluble oxygenated hydrocarbon comprising a $C_{1+}O_{1+}$ hydrocarbon in an aqueous liquid phase and/or a vapor phase,
catalytically reacting a portion of the water and oxygenated hydrocarbon in the liquid phase and/or vapor phase in the presence of an aqueous phase reforming catalyst at a reforming temperature and a reforming pressure to produce in situ generated $H_2$,
catalytically reacting in the liquid and/or vapor phase the oxygenated hydrocarbon with the in situ generated $H_2$ in the presence of a deoxygenation catalyst at a deoxygenation temperature and deoxygenation pressure to produce an oxygenate comprising a $C_{1+}O_{1+}$ hydrocarbon in a reaction stream, and
catalytically reacting in the liquid and/or vapor phase the oxygenate in the presence of a base catalyst at a condensation temperature and condensation pressure to produce the $C_{4+}$ compound,
wherein the $C_{4+}$ compound comprises a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and a mixture thereof.

100. The method of claim 99, further comprising providing supplemental $H_2$, and catalytically reacting a portion of the oxygenated hydrocarbon with supplemental $H_2$ in the presence of the deoxygenation catalyst to produce the oxygenate.

101. The method of claim 100, further comprising catalytically reacting in the liquid and/or vapor phase sugar, furfural, carboxylic acid, ketone, or furan with in situ generated $H_2$ and/or supplemental $H_2$ in the presence of a hydrogenation catalyst at a hydrogenation temperature and hydrogenation pressure to produce the oxygenated hydrocarbon.

102. The method of claim 100, further comprising catalytically reacting in the liquid and/or vapor phase a sugar, sugar alcohol or polyhydric alcohol with in situ generated $H_2$ and/or supplemental $H_2$ in the presence of a hydrogenolysis catalyst at a hydrogenolysis temperature and hydrogenolysis pressure to produce the oxygenated hydrocarbon.

103. The method of claim 99, wherein the water soluble oxygenated hydrocarbon comprises a member selected from the group consisting of polysaccharides, disaccharides, monosaccharides, cellulose derivatives, lignin derivatives, hemicellulose, sugars, sugar alcohols and a mixture thereof, and wherein the oxygenated hydrocarbon optionally further comprises recycled $C_{1+}O_{1+}$ hydrocarbon.

104. The method of claim 99, wherein the oxygenate comprises a member selected from the group consisting of an alcohol, ketone, aldehyde, furan, diol, triol, hydroxy carboxylic acid, carboxylic acid, methanol, ethanol, n-propyl alcohol, isopropyl alcohol, butyl alcohol, pentanol, hexanol, cyclopentanol, cyclohexanol, 2-methylcyclopentanol, hydroxyketones, cyclic ketones, acetone, propanone, butanone, pentanone, hexanone, 2-methyl-cyclopentanone, ethylene glycol, 1,3-propanediol, propylene glycol, butanediol, pentanediol, hexanediol, methylglyoxal, butanedione, pentanedione, diketohexane, hydroxyaldehydes, acetaldehyde, propionaldehyde, butyraldehyde, pentanal, hexanal, formic acid, acetic acid, propionic acid, butanoic acid, pentanoic acid, hexanoic acid, lactic acid, glycerol, furan, tetrahydrofuran, dihydrofuran, 2-furan methanol, 2-methyl-tetrahydrofuran, 2,5-dimethyl-tetrahydrofuran, 2-ethyl-tetrahydrofuran, 2-methyl furan, 2,5-dimethyl furan, 2-ethyl furan, hydroxylmethylfurfural, 3-hydroxytetrahydrofuran, tetrahydro-3-furanol, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, and hydroxymethyltetrahydrofurfural, isomers of any of the foregoing, and combinations of any of the foregoing, and wherein the oxygenate optionally further comprises recycled $C_{1+}O_{1-3}$ hydrocarbon.

105. The method of claim 99, wherein the $C_{4+}$ compound comprises a member selected from a branched or straight chain $C_{4-30}$ alkane; a branched or straight chain alkane selected from the group consisting of $C_{4-9}$, $C_{7-14}$, $O_{12-24}$, and a mixture thereof; a branched or straight chain $C_{4-30}$ alkene; a branched or straight chain alkene selected from the group consisting of $C_{4-9}$, $C_{7-14}$, $C_{12-24}$, and a mixture thereof; a mono-substituted or multi-substituted $C_{5+}$ cycloalkane, and wherein at least one substituted group is a member selected from the group consisting of a branched $C_{3+}$ alkyl, a straight chain $C_{1+}$ alkyl, a branched $C_{3+}$ alkylene, a straight chain $C_{1+}$ alkylene, a phenyl, and a combination thereof; a mono-substituted or multi-substituted $C_{5+}$ cycloalkene, and wherein at least one substituted group is a member selected from the group consisting of a branched $C_{3+}$ alkyl, a straight chain $C_{1+}$ alkyl, a branched $C_{1+}$ alkylene, a straight chain $C_{2+}$ alkylene, a phenyl, and a combination thereof; an unsubstituted aryl; a mono-substituted or multi-substituted aryl, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof; an unsubstituted fused aryl; a mono-substituted or multi-substituted fused aryl, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof; a compound according to the formula $R^1$—OH, and a compound according to the formula

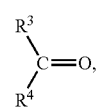

wherein $R^1$ is a member selected from the group consisting of a branched $C_{4+}$ alkyl, straight chain $C_{4+}$ alkyl, a branched $C_{4+}$ alkylene, a straight chain $C_{4+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl, and a combination thereof, and wherein $R^3$ and $R^4$ are independently a member selected from the group consisting of a branched $C_{3+}$ alkyl, a straight chain $C_{1+}$ alkyl, a branched $C_{3+}$ alkylene, a straight chain $C_{2+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl, and a combination thereof.

106. The method of claim 99, wherein the base catalyst comprises a member selected from the group consisting of hydrotalcite, zinc-aluminate, phosphate, Li, Na, K, Cs, B, Rb, Mg, Ca, Sr, Si, Ba, Al, Ce, La, Sc, Y, Zr, Ti, Zn, an alloy of any of the foregoing, and a combination of any of the foregoing; a metal oxide of a member selected from the group consisting of Cu, Ni, Zn, V, Zr, and a combination of any of the foregoing metal oxides; and zinc-aluminate and a metal selected from the group consisting of Pd, Pt, Ni, Cu, and a combination of any of the foregoing metals.

107. The method of claim 99, wherein the deoxygenation catalyst comprises a support and a member selected from the group consisting of Re, Cu, Fe, Ru, Ir, Co, Rh, Pt, Pd, Ni, W, Os, Mo, Ag, Au, an alloy thereof, and a combination thereof.

108. The method of claim 99, wherein the aqueous phase reforming catalyst comprises a support and a member selected from the group consisting of Fe, Ru, Os, Ir, Co, Rh, Pt, Pd, Ni, an alloy thereof, and a combination thereof.

109. The method of claim 99, wherein at least two of the deoxygenation catalyst, aqueous phase reforming catalyst, and condensation catalyst are atomically identical.

110. The method of claim 99, wherein the aqueous phase reforming catalyst and deoxygenation catalyst comprise Pt alloyed or admixed with a member selected from the group consisting of Ni, Ru, Cu, Fe, Rh, Re, Au, Ag, alloys thereof, and a combination thereof.

111. The method of claim 99, wherein the aqueous phase reforming catalyst and deoxygenation catalyst comprise Ru alloyed or admixed with a member selected from the group consisting of Ge, Bi, B, Ni, Sn, Cu, Fe, Rh, Pt, Au, Ag, alloys thereof, and a combination thereof.

112. The method of claim 99, wherein the aqueous phase reforming catalyst comprises Ni alloyed or admixed with a member selected from the group consisting of Sn, Ge, Bi, B, Cu, Re, Ru, Fe, Au, Ag alloys thereof, and a combination thereof.

113. The method of claim 101, wherein the hydrogenation catalyst comprises a support and a member selected from the group consisting of Fe, Ru, Os, Ir, Co, Rh, Pt, Pd, Ni, Re, Cu, alloys thereof, and a combination thereof.

114. The method of claim 102, wherein the hydrogenolysis catalyst comprises a member selected from the group consisting of phosphate, Cr, Mo, W, Re, Mn, Cu, Cd, Fe, Ru, Os, Ir, Co, Rh, Pt, Pd, Ni, alloys thereof, and a combination thereof.

115. The method of claim 99, wherein the reforming temperature is in the range of about 100° C. to about 450° C., and wherein the reforming pressure is a pressure where the water and the oxygenated hydrocarbon are gaseous.

116. The method of claim 99, wherein the reforming temperature is in the range of about 80° C. to 400° C., and wherein the reforming pressure is a pressure where the water and the oxygenated hydrocarbon are liquid.

117. The method of claim 99, wherein the deoxygenation temperature is in the range of about 100° C. to 600° C., and wherein the deoxygenation pressure is at least 0.1 atmosphere.

118. The method of claim 99, wherein the reforming temperature and deoxygenation temperature is in the range of about 100° C. to 450° C., and wherein the reforming pressure and deoxygenation pressure is in the range of about 72 psig to 1300 psig.

119. The method of claim 99, wherein the condensation temperature is in the range of about 80° C. to 500° C., and wherein the condensation pressure is at least 0.1 atm.

120. The method of claim 99, wherein the reaction stream further comprises water, and wherein the method further comprises dewatering the reaction stream prior to reacting the oxygenate in the presence of the condensation catalyst.

121. The method of claim 99, wherein the step of catalytically reacting the oxygenated hydrocarbon with in situ generated $H_2$ in the presence of the deoxygenation catalyst is conducted in the presence of an insignificantly effective amount of external $H_2$.

122. The method of claim 100, wherein the molar ratio of the total oxygen atoms in the oxygenated hydrocarbons to the total hydrogen atoms in the supplemental $H_2$ is less than 1:1.

123. The method of claim 99, further comprising catalytically reacting the $C_{4+}$ compound in the liquid phase and/or vapor phase in the presence of a finishing catalyst at a finishing temperature and a finishing pressure, wherein the finishing catalyst comprises a support and a member selected from the group consisting of Cu, Ni, Fe, Co, Ru, Pd, Rh, Pt, Ir, Os, an alloy thereof, and a combination thereof.

124. The method of claim 123, wherein the finishing catalyst further comprises a modifier selected from the group consisting of Au, Ag, Cr, Zn, Mn, Sn, Cu, Cr, Bi, alloys thereof, and a combination thereof.

125. The method of claim 123, wherein the support comprises a member selected from the group consisting of a nitride, carbon, silica, alumina, zirconia, titania, vanadia, ceria, boron nitride, heteropolyacid, kieselguhr, hydroxyapatite, zinc oxide, chromia, zeolites, and mixtures of any of the foregoing and optionally wherein the support is modified by treating the support with a modifier selected from the group consisting of silanes, alkali compounds, alkali earth compounds, and lanthanides.

126. The method of claim 99, performed in a reactor system comprising one or more reactor vessels, wherein the reactor system is adapted to be configured as continuous flow, batch, semi-batch, multi-system or a combination thereof.

127. The method of claim 126, wherein the reactor system further comprises one or more of a fluidized catalytic bed, a swing bed, fixed bed, moving bed or a combination thereof, wherein each bed is adapted to be housed within a reactor vessel.

128. The method of claim 127, performed in the continuous flow reactor system at steady-state equilibrium.

129. The method of claim 128, wherein the continuous flow reactor system is oriented to provide horizontal, vertical or diagonal flow.

130. The method of claim 99, wherein each catalytic reaction occurs at steady-state equilibrium.

131. The method of claim 102, wherein the hydrogenolysis temperature is in the range of about 110° C. to 300° C.

132. The method of claim 102, wherein the supplemental $H_2$ comprises external $H_2$, recycled $H_2$ or a combination thereof.

133. The method of claim 101, wherein the hydrogenation temperature is in the range of about 80° C. to 250° C., and wherein the hydrogenation pressure is in the range of about 100 psig to 2000 psig.

134. The method of claim 101, wherein the supplemental $H_2$ comprises external $H_2$, recycled $H_2$ or a combination thereof.

135. A method of making a $C_{4+}$ compound comprising:
providing an aqueous solution comprising water and a member selected from the group consisting of a sugar, furfural, carboxylic acid, ketone, furan, and a combination thereof;
catalytically reacting in a liquid and/or vapor phase the sugar, furfural, carboxylic acid, ketone, furan, or combination thereof, with $H_2$ in the presence of a hydrogenation catalyst at a hydrogenation temperature and hydrogenation pressure to produce an oxygenated hydrocarbon comprising a $C_{1+}O_{1-3}$ hydrocarbon,
catalytically reacting a portion of the water and oxygenated hydrocarbon in the liquid phase and/or vapor phase in the presence of an aqueous phase reforming catalyst at a reforming temperature and a reforming pressure to produce in situ generated $H_2$,
catalytically reacting in the liquid and/or vapor phase the oxygenated hydrocarbon with the in situ generated $H_2$ in the presence of a deoxygenation catalyst at a deoxygenation temperature and deoxygenation pressure to produce an oxygenate comprising a $C_{1+}O_{1-3}$ hydrocarbon, and
catalytically reacting in the liquid and/or vapor phase the oxygenate in the presence of a base catalyst at a condensation temperature and condensation pressure to produce the $C_{4+}$ compound,
wherein the $C_{4+}$ compound comprises a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and a mixture thereof.

136. The method of claim 135, further comprising providing supplemental $H_2$ comprising external $H_2$, recycled $H_2$ or a combination thereof, and reacting the supplemental $H_2$ with the sugar, furfural, carboxylic acid, ketone, furan, or combination thereof and/or with the $C_{1+}O_{1+}$ oxygenated hydrocarbon.

137. The method of claim 135, wherein:
the oxygenated hydrocarbon comprises a member selected from the group consisting of polysaccharides, disaccharides, monosaccharides, cellulose derivatives, lignin derivatives, hemicellulose, sugars, sugar alcohols and a mixture thereof, and wherein the oxygenated hydrocarbon optionally further comprises recycled $C_{1+}O_{1+}$ hydrocarbon;
the oxygenate comprises a member selected from the group consisting of an alcohol, ketone, aldehyde, furan, diol, triol, hydroxy carboxylic acid, carboxylic acid, a mixture of any of the foregoing, methanol, ethanol, n-propyl alcohol, isopropyl alcohol, butyl alcohol, pentanol, hexanol, cyclopentanol, cyclohexanol, 2-methyl-cyclopentanol, hydroxyketones, cyclic ketones, acetone, propanone, butanone, pentanone, hexanone, 2-methyl-cyclopentanone, ethylene glycol, 1,3-propanediol, propylene glycol, butanediol, pentanediol, hexanediol, methylglyoxal, butanedione, pentanedione, diketohexane, hydroxyaldehydes, acetaldehyde, propionaldehyde, butyraldehyde, pentanal, hexanal, formic acid, acetic acid, propionic acid, butanoic acid, pentanoic acid, hexanoic acid, lactic acid, glycerol, furan, tetrahydrofuran, dihydrofuran, 2-furan methanol, 2-methyl-tetrahydrofuran, 2,5-dimethyl-tetrahydrofuran, 2-ethyl-tetrahydrofuran, 2-methyl furan, 2,5-dimethyl furan, 2-ethyl furan, hydroxylmethylfurfural, 3-hydroxytetrahydrofuran, tetrahydro-3-furanol, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, and hydroxymethyltetrahydrofurfural, isomers of any of methanol through hydroxymethyltetrahydrofurfural, and combinations of any of methanol through hydroxymethyltetrahydrofurfural, and wherein the oxygenate optionally further comprises recycled $C_{1+}O_{1-3}$ hydrocarbon;
the $C_{4+}$ compound comprises a member selected from a branched or straight chain $C_{4-30}$ alkane; a branched or straight chain alkane selected from the group consisting of $C_{4-9}$, $C_{7-14}$, $C_{12-24}$, and a mixture thereof; a branched or straight chain $C_{4-30}$ alkene; a branched or straight chain alkene selected from the group consisting of $C_{4-9}$, $C_{7-14}$, $C_{12-24}$, and a mixture thereof; a mono-substituted or multi-substituted $C_{5+}$ cycloalkane, and wherein at least one substituted group is a member selected from the group consisting of a branched $C_{3+}$ alkyl, a straight chain $C_{1+}$ alkyl, a branched $C_{1+}$ alkylene, a straight chain $C_{1+}$ alkylene, a phenyl, and a combination thereof; a mono-substituted or multi-substituted $C_{5+}$ cycloalkene, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof; an unsubstituted aryl; a mono-substituted or multi-substituted aryl, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof; an unsubstituted fused aryl; a mono-substituted or multi-substituted fused aryl, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof; a compound according to the formula $R^1$—OH, and a compound according to the formula

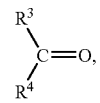

wherein $R^1$ is a member selected from the group consisting of a branched $C_{4+}$ alkyl, straight chain $C_{4+}$ alkyl, a branched $C_{4+}$ alkylene, a straight chain $C_{4+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl, and a combination thereof, and wherein $R^3$ and $R^4$ are independently a member selected from the group consisting of a branched $C_{3+}$ alkyl, a straight chain $C_{1+}$ alkyl, a branched $C_{3+}$ alkylene, a straight chain $C_{2+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl, and a combination thereof;
the hydrogenation catalyst comprises a support and a member selected from the group consisting of Fe, Ru, Os, Ir, Co, Rh, Pt, Pd, Ni, Re, Cu, alloys thereof, and a combination thereof;
the aqueous phase reforming catalyst comprises a support and a member selected from the group consisting of Fe, Ru, Os, Ir, Co, Rh, Pt, Pd, Ni, an alloy thereof, and a combination thereof;
the base catalyst comprises a member selected from the group consisting of hydrotalcite, zinc-aluminate, phosphate, Li, Na, K, Cs, B, Rb, Mg, Ca, Sr, Si, Ba, Al, Ce, La, Sc, Y, Zr, Ti, Zn, an alloy of any of the foregoing, and a combination of any of the foregoing; a metal oxide of a member selected from the group consisting of Cu, Ni, Zn, V, Zr, and a combination of any of the foregoing metal oxides; and zinc-aluminate and a metal selected from the group consisting of Pd, Pt, Ni, Cu, and a combination of any of the foregoing metals; and the deoxygenation catalyst comprises a support and a member selected from the group consisting of Re, Cu, Fe, Ru, Ir, Co, Rh, Pt, Pd, Ni, W, Os, Mo, Ag, Au, an alloy thereof, and a combination thereof.

138. The method of claim 135, wherein at least two of the hydrogenation catalyst, aqueous phase reforming catalyst, deoxygenation catalyst, and condensation catalyst are atomically identical.

139. A method of making a $C_{4+}$ compound comprising:
providing an aqueous solution comprising water and a member selected from the group consisting of a polysaccharide, disaccharide, monosaccharide, polyhydric alcohol, sugar, sugar alcohol, and a combination thereof;
catalytically reacting in a liquid and/or vapor phase the sugar, sugar alcohol, polysaccharide, disaccharide, monosaccharide, polyhydric alcohol, or combination, with $H_2$ in the presence of a hydrogenolysis catalyst at a hydrogenolysis temperature and hydrogenolysis pressure to produce an oxygenated hydrocarbon comprising a $C_{1+}O_{1+}$ hydrocarbon,
catalytically reacting a portion of the water and oxygenated hydrocarbon in the liquid phase and/or vapor phase in the presence of an aqueous phase reforming catalyst at a reforming temperature and a reforming pressure to produce in situ generated $H_2$,
catalytically reacting in the liquid and/or vapor phase the oxygenated hydrocarbon with the in situ generated $H_2$ in the presence of a deoxygenation catalyst at a deoxygenation temperature and deoxygenation pressure to produce an oxygenate comprising a $C_{1+}O_{1-3}$ hydrocarbon, and
catalytically reacting in the liquid and/or vapor phase the oxygenate in the presence of a base catalyst at a condensation temperature and condensation pressure to produce the $C_{4+}$ compound,
wherein the $C_{4+}$ compound comprises a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and a mixture thereof.

140. The method of claim 139, further comprising providing supplemental $H_2$ comprising external $H_2$, recycled $H_2$ or a combination thereof, and reacting the supplemental $H_2$ with the polysaccharide, disaccharide, monosaccharide, polyhydric alcohol, sugar, sugar alcohol, or combination thereof and/or with the $C_{1+}O_{1-3}$ oxygenated hydrocarbon.

141. The method of claim 139, wherein:
the oxygenated hydrocarbon comprises a member selected from the group consisting of polysaccharides, disaccharides, monosaccharides, cellulose derivatives, lignin derivatives, hemicellulose, sugars, sugar alcohols and a mixture thereof, and wherein the oxygenated hydrocarbon optionally further comprises recycled $C_{1+}O_{1+}$ hydrocarbon;
the oxygenate comprises a member selected from the group consisting of an alcohol, ketone, aldehyde, furan, diol, triol, hydroxy carboxylic acid, carboxylic acid, a mixture of any of the foregoing, methanol, ethanol, n-propyl alcohol, isopropyl alcohol, butyl alcohol, pentanol, hexanol, cyclopentanol, cyclohexanol, 2-methyl-cyclopentanol, hydroxyketones, cyclic ketones, acetone, propanone, butanone, pentanone, hexanone, 2-methyl-cyclopentanone, ethylene glycol, 1,3-propanediol, propylene glycol, butanediol, pentanediol, hexanediol, methylglyoxal, butanedione, pentanedione, diketohexane, hydroxyaldehydes, acetaldehyde, propionaldehyde, butyraldehyde, pentanal, hexanal, formic acid, acetic acid, propionic acid, butanoic acid, pentanoic acid, hexanoic acid, lactic acid, glycerol, furan, tetrahydrofuran, dihydrofuran, 2-furan methanol, 2-methyl-tetrahydrofuran, 2,5-dimethyl-tetrahydrofuran, 2-ethyl-tetrahydrofuran, 2-methyl furan, 2,5-dimethyl furan, 2-ethyl furan, hydroxylmethylfurfural, 3-hydroxytetrahydrofuran, tetrahydro-3-furanol, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, and hydroxymethyltetrahydrofurfural, isomers of any of methanol through hydroxymethyltetrahydrofurfural, and combinations of any of methanol through hydroxymethyltetrahydrofurfural, and wherein the oxygenate optionally further comprises recycled $C_{1+}O_{1-3}$ hydrocarbon;

the $C_{4+}$ compound comprises a member selected from a branched or straight chain $C_{4-30}$ alkane; a branched or straight chain alkane selected from the group consisting of $C_{4-9}$, $C_{7-14}$, $C_{12-24}$, and a mixture thereof; a branched or straight chain $C_{4-30}$ alkene; a branched or straight chain alkene selected from the group consisting of $C_{4-9}$, $C_{7-14}$, $C_{12-24}$, and a mixture thereof; a mono-substituted or multi-substituted $C_{5+}$ cycloalkane, and wherein at least one substituted group is a member selected from the group consisting of a branched $C_{3+}$ alkyl, a straight chain $C_{1+}$ alkyl, a branched $C_{1+}$ alkylene, a straight chain $C_{1+}$ alkylene, a phenyl, and a combination thereof; a mono-substituted or multi-substituted $C_{5+}$ cycloalkene, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof; an unsubstituted aryl; a mono-substituted or multi-substituted aryl, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof; an unsubstituted fused aryl; a mono-substituted or multi-substituted fused aryl, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof; a compound according to the formula $R^1$—OH, and a compound according to the formula

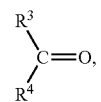

wherein $R^1$ is a member selected from the group consisting of a branched $C_{4+}$ alkyl, straight chain $C_{4+}$ alkyl, a branched $C_{4+}$ alkylene, a straight chain $C_4$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl, and a combination thereof, and wherein $R^3$ and $R^4$ are independently a member selected from the group consisting of a branched $C_{3+}$ alkyl, a straight chain $C_{1+}$ alkyl, a branched $C_{3+}$ alkylene, a straight chain $C_2$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl, and a combination thereof;

the hydrogenolysis catalyst comprises a member selected from the group consisting of phosphate, Cr, Mo, W, Re, Mn, Cu, Cd, Fe, Ru, Os, Ir, Co, Rh, Pt, Pd, Ni, alloys thereof, and a combination thereof;

the aqueous phase reforming catalyst comprises a support and a member selected from the group consisting of Fe, Ru, Os, Ir, Co, Rh, Pt, Pd, Ni, an alloy thereof, and a combination thereof;

the base catalyst comprises a member selected from the group consisting of hydrotalcite, zinc-aluminate, phosphate, Li, Na, K, Cs, B, Rb, Mg, Ca, Sr, Si, Ba, Al, Ce, La, Sc, Y, Zr, Ti, Zn, an alloy of any of the foregoing, and a combination of any of the foregoing; a metal oxide of a member selected from the group consisting of Cu, Ni, Zn, V, Zr, and a combination of any of the foregoing metal oxides; and zinc-aluminate and a metal selected from the group consisting of Pd, Pt, Ni, Cu, and a combination of any of the foregoing metals; and the deoxygenation catalyst comprises a support and a member selected from the group consisting of Re, Cu, Fe, Ru, Ir, Co, Rh, Pt, Pd, Ni, W, Os, Mo, Ag, Au, an alloy thereof, and a combination thereof.

142. The method of claim 139, wherein at least two of the hydrogenolysis catalyst, aqueous phase reforming catalyst, deoxygenation catalyst, and condensation catalyst are atomically identical.

143. A method of making a $C_{4+}$ compound comprising:
providing an oxygenate comprising a $C_{1+}O_{1-3}$ hydrocarbon derived from biomass in an aqueous liquid phase and/or a vapor phase, and
catalytically reacting in the liquid and/or vapor phase the oxygenate in the presence of a condensation catalyst at a condensation temperature and condensation pressure to produce the $C_{4+}$ compound,
wherein the $C_{4+}$ compound comprises a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and a mixture thereof.

144. The method of claim 143, wherein:
the oxygenate comprises a member selected from the group consisting of an alcohol, ketone, aldehyde, furan, diol, triol, hydroxy carboxylic acid, carboxylic acid, a mixture of any of the foregoing, methanol, ethanol, n-propyl alcohol, isopropyl alcohol, butyl alcohol, pentanol, hexanol, cyclopentanol, cyclohexanol, 2-methyl-cyclopentanol, hydroxyketones, cyclic ketones, acetone, propanone, butanone, pentanone, hexanone, 2-methyl-cyclopentanone, ethylene glycol, 1,3-propanediol, propylene glycol, butanediol, pentanediol, hexanediol, methylglyoxal, butanedione, pentanedione, diketohexane, hydroxyaldehydes, acetaldehyde, propionaldehyde, butyraldehyde, pentanal, hexanal, formic acid, acetic acid, propionic acid, butanoic acid, pentanoic acid, hexanoic acid, lactic acid, glycerol, furan, tetrahydrofuran, dihydrofuran, 2-furan methanol, 2-methyl-tetrahydrofuran, 2,5-dimethyl-tetrahydrofuran, 2-ethyl-tetrahydrofuran, 2-methyl furan, 2,5-dimethyl furan, 2-ethyl furan, hydroxylmethylfurfural, 3-hydroxytetrahydrofuran, tetrahydro-3-furanol, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, and hydroxymethyltetrahydrofurfural, isomers of any of methanol through hydroxymethyltetrahydrofurfural, and combinations of any of methanol through hydroxymethyltetrahydrofurfural, and wherein the oxygenate optionally further comprises recycled $C_{1+}O_{1-3}$ hydrocarbon;

the $C_{4+}$ compound comprises a member selected from a branched or straight chain $C_{4-30}$ alkane; a branched or straight chain alkane selected from the group consisting of $C_{4-9}$, $C_{7-14}$, $C_{12-24}$, and a mixture thereof; a branched or straight chain $C_{4-30}$ alkene; a branched or straight chain alkene selected from the group consisting of $C_{4-9}$, $C_{7-14}$, $C_{12-24}$, and a mixture thereof; a mono-substituted or multi-substituted $C_{5+}$ cycloalkane, and wherein at least one substituted group is a member selected from the group consisting of a branched $C_{3+}$ alkyl, a straight chain $C_{1+}$ alkyl, a branched $C_{1+}$ alkylene, a straight chain $C_{1+}$ alkylene, a phenyl, and a combination thereof; a mono-substituted or multi-substituted $C_{5+}$ cycloalkene, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof; an unsubstituted aryl; a mono-substituted or multi-substituted aryl, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof; an unsubstituted fused aryl; a mono-substituted or multi-substituted fused aryl, and wherein at least one substituted group is a member selected from the group consisting of a branched $C_{3+}$ alkyl, a straight chain $C_{1+}$ alkyl, a branched $C_{3+}$ alkylene, a straight chain $C_{2+}$ alkylene, a phenyl, and a combination thereof; a compound according to the formula $R^1$—OH, and a compound according to the formula

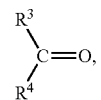

wherein $R^1$ is a member selected from the group consisting of a branched $C_{4+}$ alkyl, straight chain $C_{4+}$ alkyl, a branched $C_{4+}$ alkylene, a straight chain $C_4$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl, and a combination thereof, and wherein $R^3$ and $R^4$ are independently a member selected from the group consisting of a branched $C_{3+}$ alkyl, a straight chain $C_{1+}$ alkyl, a branched $C_{3+}$ alkylene, a straight chain $C_2$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl, and a combination thereof;

and the base catalyst comprises a member selected from the group consisting of hydrotalcite, zinc-aluminate, phosphate, Li, Na, K, Cs, B, Rb, Mg, Ca, Sr, Si Ba, Al, Ce La, Sc, Y, Zr, Ti, Zn, an alloy of any of the foregoing, and a combination of any of the foregoing; a metal oxide of a member selected from the group consisting of Cu, Ni, Zn, V, Zr, and a combination of any of the foregoeing metal oxides; and zinc-aluminate and a metal selected from the group consisting of Pd, Pt, Ni, Cu and a combination of any of the foregoing metals.

* * * * *

UNITED STATES PATENT AND TRADEMARK OFFICE
CERTIFICATE OF CORRECTION

PATENT NO. : 7,977,517 B2
APPLICATION NO. : 12/044908
DATED : July 12, 2011
INVENTOR(S) : Randy D. Cortright et al.

It is certified that error appears in the above-identified patent and that said Letters Patent is hereby corrected as shown below:

Delete the title page and substitute therefore the attached title page showing the corrected number of claims in patent.

Column 87, line 33-Column 88, line 64, delete claims 143 and 144.

Signed and Sealed this
Fifth Day of February, 2013

Teresa Stanek Rea
*Acting Director of the United States Patent and Trademark Office*

(12) United States Patent
Cortright et al.

(10) Patent No.: US 7,977,517 B2
(45) Date of Patent: *Jul. 12, 2011

(54) SYNTHESIS OF LIQUID FUELS AND CHEMICALS FROM OXYGENATED HYDROCARBONS

(75) Inventors: Randy D. Cortright, Madison, WI (US); Paul G. Blommel, Oregon, WI (US)

(73) Assignee: Virent Energy Systems, Inc., Madison, WI (US)

( * ) Notice: Subject to any disclaimer, the term of this patent is extended or adjusted under 35 U.S.C. 154(b) by 471 days.

This patent is subject to a terminal disclaimer.

(21) Appl. No.: 12/044,908

(22) Filed: Mar. 7, 2008

(65) Prior Publication Data
US 2008/0300435 A1   Dec. 4, 2008

Related U.S. Application Data

(60) Provisional application No. 60/985,475, filed on Nov. 5, 2007, provisional application No. 60/985,500, filed on Nov. 5, 2007, provisional application No. 60/905,703, filed on Mar. 8, 2007.

(51) Int. Cl.
*C07C 4/00* (2006.01)
*C07C 29/60* (2006.01)

(52) U.S. Cl. ........ 585/240; 585/242; 568/801; 568/861; 423/437.1

(58) Field of Classification Search .............. 585/241, 585/242; 568/861, 801; 44/605; 423/437.1
See application file for complete search history.

(56) References Cited

U.S. PATENT DOCUMENTS

| | | |
|---|---|---|
| 2,965,679 A | 12/1960 | Conradin et al. |
| 3,894,107 A | 7/1975 | Butter et al. |
| 4,013,734 A | 3/1977 | Kim |
| 4,223,001 A | 9/1980 | Novotny et al. |
| 4,380,679 A | 4/1983 | Arena |
| 4,380,680 A | 4/1983 | Arena |
| 4,382,150 A | 5/1983 | Arena |
| 4,401,823 A | 8/1983 | Arena |
| 4,456,779 A | 6/1984 | Owen et al. |
| 4,476,331 A | 10/1984 | Dubeck et al. |
| 4,487,980 A | 12/1984 | Arena |
| 4,496,780 A | 1/1985 | Arena |
| 4,503,274 A | 3/1985 | Arena |

(Continued)

FOREIGN PATENT DOCUMENTS
CA         1201080 A1     2/1986
(Continued)

OTHER PUBLICATIONS

Gayubo et al., "Transformation of Oxygenate Components of Biomass Pyrolsis Oil on a HZSM-5 Zeolite. II. Aldehydes, Ketones, and Acids," Ind. Eng. Chem Res. 2004, 43:2619-2626.

(Continued)

*Primary Examiner* — N. Bhat
(74) *Attorney, Agent, or Firm* — Quarles & Brady LLP

(57) ABSTRACT

Processes and reactor systems are provided for the conversion of oxygenated hydrocarbons to hydrocarbons, ketones and alcohols useful as liquid fuels, such as gasoline, jet fuel or diesel fuel, and industrial chemicals. The process involves the conversion of mono-oxygenated hydrocarbons, such as alcohols, ketones, aldehydes, furans, carboxylic acids, diols, triols, and/or other polyols, to $C_{4+}$ hydrocarbons, alcohols and/or ketones, by condensation. The oxygenated hydrocarbons may originate from any source, but are preferably derived from biomass.

142 Claims, 19 Drawing Sheets